(12) United States Patent
Valbjørn et al.

(10) Patent No.: US 10,617,764 B2
(45) Date of Patent: Apr. 14, 2020

(54) LYOPHILIZED ANTI-TISSUE FACTOR ANTIBODY-DRUG CONJUGATES

(71) Applicant: GENMAB A/S, Copenhagen V (DK)

(72) Inventors: Jesper Valbjørn, Veksø (DK); Xiaona Jing, Soborg (DK); Kelly Ann Roby, Bloomington, IN (US); Timothy Warren Paul, Bloomington, IN (US); Gregory Allan Sacha, Bargersville, IN (US); Nathan Alan Pease, Bloomington, IN (US); Bodil Willumsen, Basel (CH)

(73) Assignee: GENMAB A/S, Copenhagen V (DK)

( * ) Notice: Subject to any disclaimer, the term of this patent is extended or adjusted under 35 U.S.C. 154(b) by 665 days.

(21) Appl. No.: 15/038,235

(22) PCT Filed: Nov. 21, 2014

(86) PCT No.: PCT/EP2014/075326
§ 371 (c)(1),
(2) Date: May 20, 2016

(87) PCT Pub. No.: WO2015/075201
PCT Pub. Date: May 28, 2015

(65) Prior Publication Data
US 2016/0279258 A1 Sep. 29, 2016

Related U.S. Application Data

(60) Provisional application No. 61/907,001, filed on Nov. 21, 2013.

(51) Int. Cl.
| | | |
|---|---|---|
| *A61K 39/395* | (2006.01) | |
| *A61K 47/48* | (2006.01) | |
| *A61K 9/19* | (2006.01) | |
| *A61K 47/22* | (2006.01) | |
| *C07K 16/36* | (2006.01) | |
| *A61K 47/26* | (2006.01) | |

(52) U.S. Cl.
CPC .......... *A61K 47/48538* (2013.01); *A61K 9/19* (2013.01); *A61K 47/22* (2013.01); *C07K 16/36* (2013.01); *A61K 47/26* (2013.01); *C07K 2317/21* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 5,223,427 | A * | 6/1993 | Edgington | C07H 21/00 435/337 |
| 7,605,235 | B2 * | 10/2009 | Anderson | C07K 16/36 424/178.1 |
| 7,824,677 | B2 * | 11/2010 | Wong | A61K 39/395 424/133.1 |
| 9,068,011 | B2 | 6/2015 | Neijssen et al. | |
| 9,150,658 | B2 | 10/2015 | Verploegen et al. | |
| 9,168,314 | B2 * | 10/2015 | Satijn | C07K 16/36 |
| 9,492,565 | B2 | 11/2016 | Satijn et al. | |
| 9,657,107 | B2 | 5/2017 | Neijssen et al. | |
| 9,714,297 | B2 | 7/2017 | Verploegen et al. | |
| 2007/0196364 | A1 * | 8/2007 | Krishnamurthy | A61K 31/7012 424/133.1 |
| 2011/0300156 | A1 | 12/2011 | Verploegen et al. | |
| 2013/0101608 | A1 | 4/2013 | Satijn et al. | |
| 2013/0216548 | A1 | 8/2013 | Neijssen et al. | |
| 2015/0329642 | A1 | 11/2015 | Neijssen et al. | |
| 2016/0053020 | A1 | 2/2016 | Verploegen et al. | |
| 2016/0067349 | A1 | 3/2016 | Satijn et al. | |
| 2017/0136130 | A1 | 5/2017 | Satijn et al. | |
| 2017/0313782 | A1 | 11/2017 | Neijssen et al. | |
| 2017/0320962 | A1 | 11/2017 | Neijssen et al. | |
| 2018/0044431 | A1 | 2/2018 | Verploegen et al. | |
| 2019/0030178 | A1 | 1/2019 | Lisby et al. | |
| 2019/0169311 | A1 | 6/2019 | Verploegen et al. | |

FOREIGN PATENT DOCUMENTS

| | | | | |
|---|---|---|---|---|
| WO | WO-8911297 A1 * | 11/1989 | ........... | A61K 9/0019 |
| WO | WO-9405328 A1 * | 3/1994 | ........... | C07K 14/745 |
| WO | WO-2004007557 A2 * | 1/2004 | ........... | A61K 51/088 |
| WO | 2007/019232 A2 | 2/2007 | | |
| WO | WO-2007019232 A2 * | 2/2007 | ........... | A61K 9/0019 |
| WO | 2009/002425 A2 | 12/2008 | | |
| WO | WO-2009002425 A2 * | 12/2008 | ........... | A61K 9/0019 |
| WO | 2011/119487 A2 | 9/2011 | | |

(Continued)

OTHER PUBLICATIONS

Janeway et al., Immunobiology, 3rd edition, 1997, Garland Publishing, Inc., pp. 3:1-3:11.*
Rudikoff et al., Proc Natl Acad Sci U S A. Mar. 1982;79(6):1979-83.*
Breij E.C. et al., "An antibody-drug conjugate targeting tissue factor with broad anti-tumor efficacy in xenograft models with heterogeneous tissue factor expression," Cancer Research, vol. 73(8)(Suppl. 1):p. 1234 (2013) & 104TH Annual Meeting of the American Association for Cancer Research (AACR); Washington, DC, USA; Apr. 6-10, 2013 ISSN: 0008-5472, DOI: 10.1158/1538-7445.AM2013-1234 Retrieved from the Internet: URL:http://cancerres.aacrjournals.org/content/73/8Supplement/1234>[retrieved on Feb. 19, 2015] Abstract.

(Continued)

*Primary Examiner* — Michael Szperka
(74) *Attorney, Agent, or Firm* — Nelson Mullins Riley & Scarborough LLP; Jane E. Remillard, Esq.; Christopher L. Frank

(57) ABSTRACT

Disclosed herein are surfactant free lyophilized formulations of antibody-drug conjugates (ADCs), such as anti-tissue factor ADCs, and reconstituted formulations, processes and uses thereof. The formulations are particularly suitable for an anti-TF ADC based on an auristatin derivative or other similarly hydrophobic drug. Typically, the excipients of the formulations comprise or consist of histidine, sucrose, trehalose, mannitol and glycine.

28 Claims, 36 Drawing Sheets
Specification includes a Sequence Listing.

(56) References Cited

FOREIGN PATENT DOCUMENTS

| WO | WO-2011157741 A2 * | 12/2011 | ............. C07K 16/36 |
| WO | 2017/042352 A1 | 3/2017 | |

OTHER PUBLICATIONS

Breij, E. C., et al., "An Antibody-Drug Conjugate That Targets Tissue Factor Exhibits Potent Therapeutic Activity against a Broad Range of Solid Tumors," Cancer Research, vol. 74(4):1214-1226 (2013) XP055170885, ISSN: 0008-5472, DOI: 10.1158/0008-5472. CAN-13-2440.

Carter M. C., et al., "Instability of succinyl ester linkages in O2'-monosuccinyl cyclic AMP-protein conjugates at neutral pH," Journal of Immunological Methods, vol. 81(2): 245-257 (1985), XP023992232, ISSN: 0022-1759, DOI: 10.1016/0022-1759(85)90210-8 [retrieved on Aug. 2, 1985].

Chen T. et al., "Development of a stable lyophilized formulation for a monoclonal antibody-doxorubicin conjugate," Pharmaceutical Research, vol. 10 (10):S90 (1993) XP8175067, & AAPS (American Association of Pharmaceutical Scientists) Eighth Annual Meeting and Exposition, Orlando, Florida, USA; Nov. 14-18, 1993 ISSN: 0724-8741 Abstract.

International Preliminary Report on Patentability, PCT/EP2014/075326, dated May 24, 2016, 8 pages.

International Search Report and Written Opinion, PCT/EP2014/075326, dated Mar. 10, 2015, 13 pages.

Rowland A. J., et al.,: "Preclinical investigation of the antitumour effects of anti-CD19-idarubicin immunoconjugates," Cancer Immunotherapy, vol. 37(3):195-202 (1993) XP8175068.

Roy M L et al., "The effects of formulation and moisture on the stability of a freeze-dried monoclonal antibody-vinca conjugate: a test of the WLF glass transition theory," Developments in Biological Standardization, vol. 74:323-340 (1991), XP8175069, ISSN: 0301-5149.

Selva C. et al., "Trehalose preserves the integrity of lyophilized phycoerythrin—antihuman CD8 antibody conjugates and enhances their thermal stability in flow cytometric assays," Journal of Pharmaceutical Sciences, vol. 102 (2):649-659 (2013) XP002736578, ISSN: 1520-6017, DOI: 10.1002/jps.23398.

* cited by examiner

| | CDR1 | | CDR2 | | CDR3 | |
|---|---|---|---|---|---|---|
| QVQLVESGGGVVQPGRSLRLSCVASGFTVSSNDCMHWVRQAPGKGLEWVALWYDGVNKNYADSVKGRFTISRDKSKNTLYLQMNSLRAEDTAVYYCARRPGT------FYGLDVWGQGTTVTVSS | | | | | | VH1015-114 (1) |
| EVQLLESGGGLVQPGGSLRLSCAASGFTFSSNYAMSWVRQAPGKGLEWVSSISGSGDYIYYTDSVKGRFTISRDNSKNTLYLQMNSLRAEDTAVYYCARSPWG-------YTLDSWGQGTLVTVSS | | | | | | VH1015-011 (5) |
| EVQLLESGGGLVQPGGSLRLSCAASGFTFSSYAMSWVRQAPGKGLEWVSSASGSGDSTNYADSVKGRFTISRDNSKNTLYLQMNSLRAEDTAVYYCAKDGYFL----LWYFDLWGRGTLVTVSS | | | | | | VH1015-017 (9) |
| EVQLLESGGGLVQPGGSLRLSCAASGFTFSSYGMSWVRQAPGKGLEWVSSVSGSGGTIYYADSVKGRFTISRDNSKNTLFLQMNSLRAEDTAVYYCAKAPWT-------YYFDYWGQGTLVTVSS | | | | | | VH1015-042 (13) |
| EVQLLESGGGLVQPGGSLRLSCAASGFTFNNYAMSWVRQAPGKGLEWVSSISGSGRIYYADSVKGRFTISRDNSKNTLFLQMNSLRAEDTAVYYCAKTPWG-------YYFDYWGQGTLVTVSS | | | | | | VH1015-092 (17) |
| EVQLLESGGGLVQPGGSLRLSCAASGFTFSNYAMSWVRQAPAKGLDWVSGSGSGVTIYYADSVKGRFTISRDNSKDTLYLQMNSLRAEDTAVFFCARTPWG-------YYFDYWGQILVAVSS | | | | | | VH1015-101 (21) |
| QVQLVESGGGVVQPGRSLRLSCAASMHWVRQAPGKGLEWVAVSNDGYNDYYADSVKGRFTVSRDNSKNTLYLQMNSLRAEDTAVYYCARDGQLG-------RGYFDYWGQGTLVTVSS | | | | | | VH1015-025 (25) |
| QVQLVESGGGVVQPGRSLRLSCAASGFTFSIYAMHWVRQAPGKGLEWVAVSNDGYNKYYADSVKGRFTISRDNSKDTLYLQMNSLRAEDTAVYYCARDGQLG-------RGYFDYWGQGTLVTVSS | | | | | | VH1015-109 (29) |
| QVQLVQSGAEVRKPGSSVKVSCKASGGSFNNYAIFWVRQAPGQGFEWMGRIPIIGIAYAQKFQGRVTITADKSTSTAYMELNSLRSEDTAVYYCAGGDD------LD-AFDIWGQGTMSVSSS | | | | | | VH1015-098 (33) |
| QVQLVESGGGVVQPGRSLRLSCAGSCFTFNRAYMYWVRQAPGKGLDWVAVISNDGYNKYYADSVKGRFTISRDNSKNTLYLQMNSLRAEDTAVYYCARDHTMV-----RGAFDYWGQGTLVTVSS | | | | | | VH1015-111 (37) |

VL:

| | CDR1 | | CDR2 | | CDR3 | |
|---|---|---|---|---|---|---|
| EIVLTQSPGTLSLSPGERATLSCRASQSVSSSYLAWYQQKPGQAPRLLIYGASSRATGIPDRFSGSGSGTDFTLTISRLEPEDFAVYYCQQYGSS---LTFGGGTKVEIK | | | | | | VL1015-114 (41) |
| DIQMTQSPPSSLSASAGDRVTITCRASQGISSRLAWYQQKPEKAPKSLIYAASSLQSGVPSRFSGSGSGTDFTLTISSLQPEDFATYYCQQYNSYP--YTFGQGTKLEIK | | | | | | VL1015-011 (45) |
| EIVLTQSPGTLSLSPGERATLSCRASQSVRSSYLAWYQQKPGQAPRLLIYGASSRATGIPDRFSGSGSGTDFTLTISRLEPEDFAVYYCQQYGSSP-RTFGQGTKVEIK | | | | | | VL1015-017 (49) |
| EIVLTQSPGTLSLSPGERATLSCRASQSVGSSYLAWYQQKPGQAPRLLIYGASSRATGIPDRFSGSGSGTDFTLTISRLEPEDFAVYYCQQYGSSP-RTFGQGTKVEIK | | | | | | VL1015-042 (53) |
| DIQMTQSPSSLSASVGDRVTITCRASQGISSYLAWYQQKPEKAPKSLIYAASSLQSGVPSRFSGSGSGTDFTLTISSLQPEDFATYYCQQYNSYP--YTFGQGTKLEIK | | | | | | VL1015-092 (57) |
| DIQMTQSPSSLSASAGDRVTITCRASQGISSALAWYQQKPEKAPKSLIYAASNRATGIPARFSGSGSGTDFTLTISSLQPEDFATYYCQQYNSYPLYTFGQGTKLEIK | | | | | | VL1015-101 (61) |
| EIVLTQSPATLSLSPGERAILSCRASQSVSSLAWYQQKPGQAPRLLIYAASNRATGIPARFSGSGSGTDFTLTISSLEPEDFAVYYCQQRSNWP-LTFGGGTKVEIK | | | | | | VL1015-025 (65) |
| EIVLTQSPATLSLSPGERATLSCRASQSVSSLAWYQQKPGQAPRLLIYAASSLQSGVPSRFSGSGSGTDFTLTISSLEPEDFAVYYCQQYNSYP--YTFGGGTKVEIK | | | | | | VL1015-109 (69) |
| DIQMTQSPSSLSASVGDRVTITCRASQSVSSWLAWYQQKPEKAPKSLIYAASSLQSGVPSRFSGSGSGTDFTLTISSLQPEDFATYYCQQYNSYP--YTFGQGTKLEIK | | | | | | VL1015-098 (73) |
| EIVLTQSPATLSLSPGERATLSCRASQSVSSYLAWYQQKPGQAPRLLIYDASNRATGIPARFSGSGSGTDFTLTISSLEPEDFAVYYCQQRSNWP-LTFGGGTKVEIK | | | | | | VL1015-111 (77) |

LYOPHILIZED ANTI-TISSUE FACTOR ANTIBODY-DRUG CONJUGATES

RELATED APPLICATIONS

This application is a 35 U.S.C. 371 national stage filing of International Application No. PCT/EP2014/075326, filed Nov. 21, 2014, which claims priority to U.S. Provisional Patent Application No. 61/907,001, filed Nov. 21, 2013. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on May 20, 2016, is named GMI_150US_Sequence_Listing.txt and is 29,364 bytes in size.

FIELD OF THE INVENTION

The present invention relates to a lyophilized formulation suitable in particular for antibody drug conjugates (ADCs), to reconstituted formulations thereof, and to methods of preparing and using such lyophilized and reconstituted formulations in e.g. cancer therapy.

BACKGROUND OF THE INVENTION

ADCs are highly potent and specific agents for the treatment of cancer and other conditions, where the antibody portion specifically binds to its antigen on a target cell, so that the drug can exert its cytotoxic or other therapeutic effect on the target cell, optionally after internalization. Several ADCs have been described, among them ADCs based on anti-tissue factor (anti-TF) antibodies (see, e.g., WO 2011157741 A2, which is hereby incorporated by reference in its entirety).

Like other protein pharmaceuticals, however, antibodies are prone to degradation such as oxidation, deamidation and fragmentation as well as particle and aggregate formation. To provide for an ADC pharmaceutical that is stable during transport and storage, the carriers, excipients, and/or stabilizers in the pharmaceutical formulation must therefore be carefully selected. The long-term stability of an antibody or ADC can also be improved by preparing a lyophilized or freeze-dried formulation, using excipients optimized for this purpose. Many such formulations for antibodies or ADC preparations have been described in patent literature, see, e.g. WO9704801, WO9856418, WO02011753, WO02096457, WO03009817, WO03039485, U.S. Pat. No. 8,372,396, WO2004004639, WO2004016286, WO2004055164, WO 2004071439, WO2006014965, WO2006044908 and WO2007019232.

For ADCs, there is an additional challenge in that the drug conjugation in itself can reduce the stability and alter the physicochemical properties of the antibody. For example, it has been reported that the conjugation of the drug moiety DM1 to the anti-HER2 antibody trastuzumab resulted in destabilization of the CH2 domain of the antibody (Wakankar et al, 2010). Further, cytotoxic drugs often being hydrophobic, the ADC conjugate as a whole can be less soluble than the unconjugated antibody, thus becoming more prone to aggregation, particle formation and surface adsorption. Typically, both antibody and ADC formulations include a surfactant, frequently polysorbate 20 or 80, to reduce aggregation and adsorption (see, e.g., patent literature cited supra). For example, brentuximab vedotin (trade name ADCETRIS®) is an ADC based on an anti-CD30 antibody linked to the auristatin derivative MMAE, provided as a lyophilized powder which, when reconstituted in water, contains 5 mg/mL ADC, 70 mg/mL trehalose dihydrate, 5.6 mg/mL sodium citrate dihydrate, 0.21 mg/mL citric acid monohydrate, and 0.20 mg/mL polysorbate 80, at a pH of approximately 6.6.

Accordingly, surfactants are commonly used in pharmaceutical preparations and are generally perceived as acceptable pharmaceutical ingredients. As mentioned above, surfactants are commonly used to reduce aggregate formation during antibody manufacturing and formulation (see e.g. Vásquez-Rey and Lang, 2011, Biotech, Bioeng. 108:7 p 1494). However, it is a general concern of pharmaceutical formulation to reduce the usage of non-active compounds as much as possible. This concern is both to reduce the cost of the resulting drug, but also to reduce potential unwanted effects of the excipient. For example, many surfactants are more or less toxic because of the amphiphilic nature and ability to react with biological membranes. It is not uncommon to observe LC50 of surfactants in aquatic organisms as low as 10 mg/L. Further, autooxidation or the exposure to light of polysorbates can result in the formation of hydrogen peroxide which in turn can oxidize the antibody molecule leading to a an unstable product (Kerwin, 2008; Singh et al., 2012). This not only reduces the efficacy of the ADC, but can lead to the formation of potentially harmful degradation products of the same.

Indeed, a surfactant-free formulation of a huC242-DM1 ADC containing 50 mM succinic acid, pH 6.0 and 5.0% sucrose initially described in WO2004004639 as suitable for e.g. lyophilization was later reported in WO2007019232A2 to not adequately address particle and aggregate formation.

Thus, there still remains a need for surfactant free pharmaceutical formulations for ADCs that are stable during transport and storage and substantially free of particles, aggregates and degradation products.

SUMMARY OF THE INVENTION

The present inventors have discovered lyophilized formulations of anti-TF ADCs in which the anti-TF ADCs remain stable and do not form aggregates or particles when reconstituted. Very surprisingly, these can be prepared without the inclusion of surfactants such as polysorbate 20 or 80, and/or without inorganic salts. The invention thus provides for stable, surfactant free lyophilized formulations of anti-TF ADCs with pharmaceutically acceptable excipients comprising: buffer components which limit pH shifts during the lyophilizing step, at least one stabilizing agent, typically a non-reducing sugar which forms an amorphous phase with the anti-TF ADC in solid state, and at least one bulking agent, optionally wherein the lyophilized formulation can be essentially free of any salt. Exemplary excipients include, but are not limited to buffer components such as, e.g., histidine, citrate, succinate, glycolate, carbonic acid and/or phosphate, typically providing for a pH between about 5 and about 7 in aqueous formulation before lyophilization and/or after reconstitution;

one or more non-reducing sugars such as sucrose and/or trehalose;

one or more bulking agents such as mannitol and/or glycine.

These and other aspects and embodiments are described in more detail in the following sections.

LEGENDS TO THE FIGURES

FIGS. 1A-1C show the percentage HMW (FIG. 1A), main (FIG. 1B) and LMW (FIG. 1C) species obtained using SEC analysis for the HuMax-TF DOE samples stored for four weeks. For these bar graphs, the formulations were arranged in order of increasing pH from left to right for each buffer plus excipient sub-group. For each pair of bars, the left bar represents 2-8° C. and the right bar 45° C. See Example 2 for details.

FIGS. 2A-2C show the effects of various formulations on the percentage peak area for acidic (FIG. 2A), main (FIG. 2B) and basic (FIG. 2C) species observed using cIEF for the HuMax-TF DOE samples stored for one week. For these bar graphs, the formulations are arranged in order of increasing pH from left to right for each buffer plus excipient sub-group. For each pair of bars, the left bar represents 2-8° C. and the right bar 45° C. See Example 4 for details.

(FIG. 7A) Aggregates increase at 50° C. by SEC. (FIG. 7B) Main charge isoform decrease at 40° C. by icIEF. See Example 8 for details.

Figure 9:
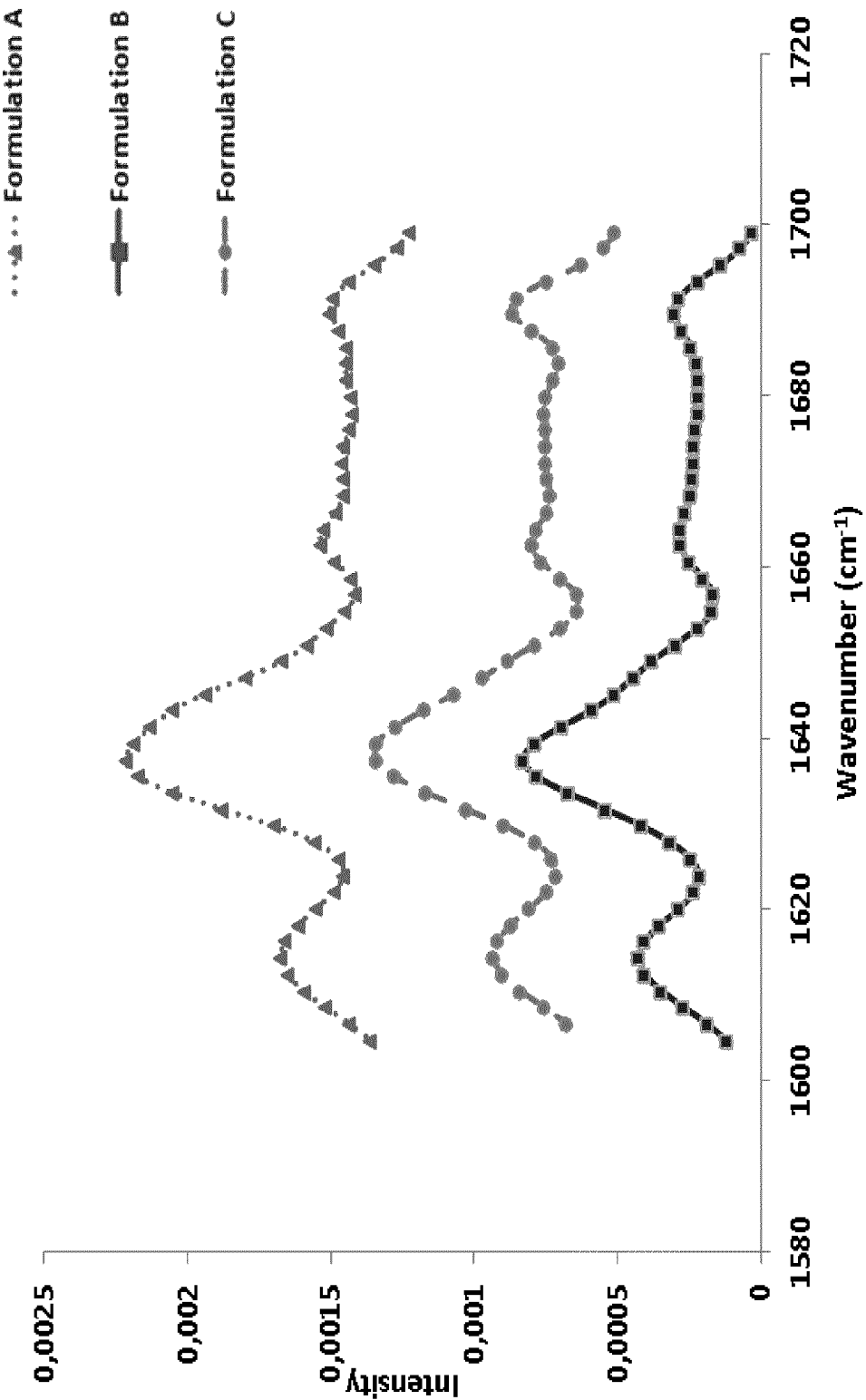

FIG. 9 shows second derivative FTIR spectra for formulations A, B, and C after storage at 50° C. for 2 weeks. The number distribution shows the number of particles in the different size bins. See Example 8 for details.

Figure 10:
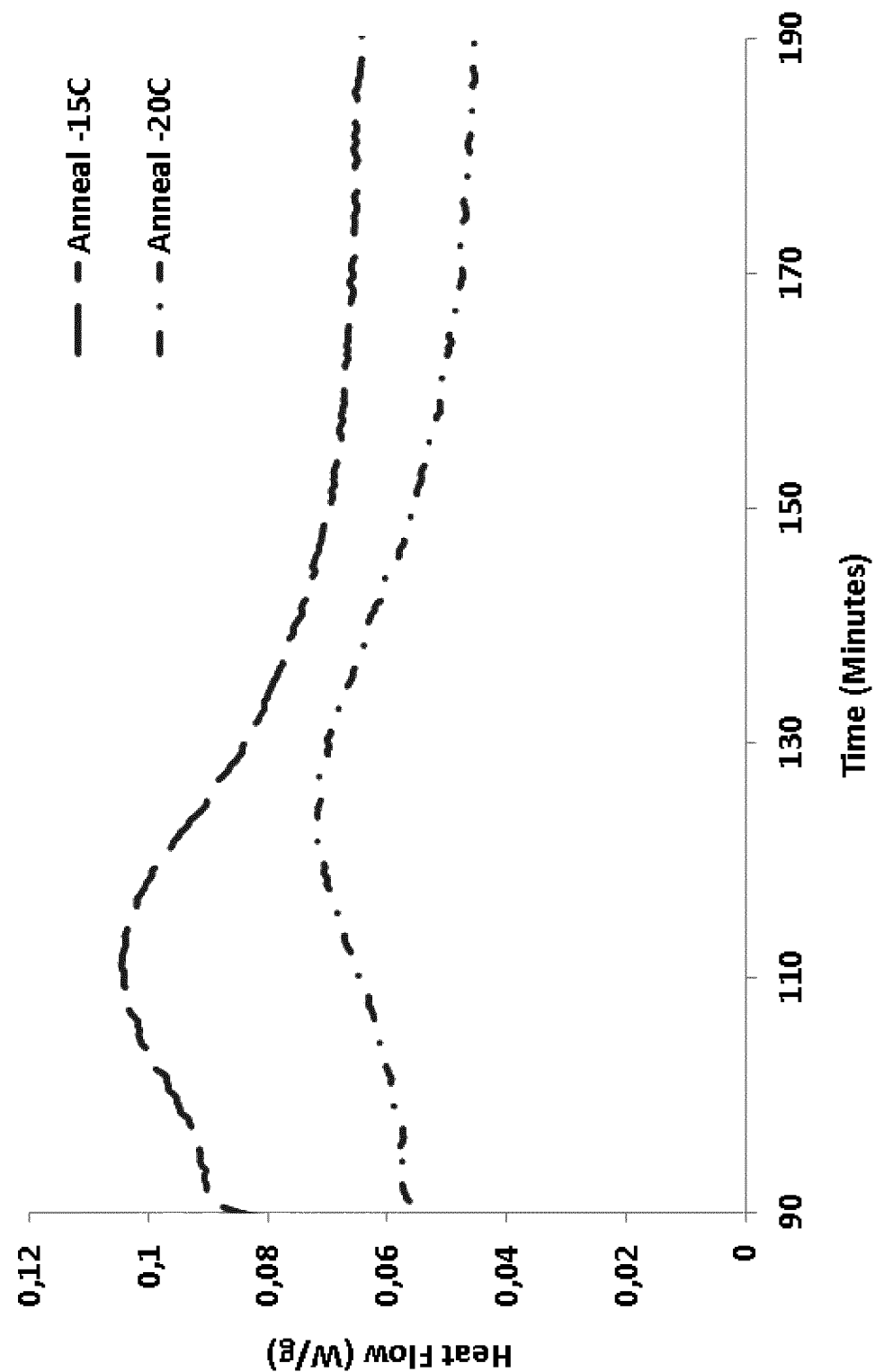

FIG. 10 shows a DSC heat flow thermogram for Formulation B. See Example 11 for details.

FIG. 11 shows the VH and VL sequences of exemplary anti-TF antibodies for use in the ADC formulations of the present invention. CDR1, CDR2 and CDR3 sequences according to Kabat are highlighted: sequences in italics represent the CDR1 region, underlined sequences represent the CDR2 region and bold sequences represent the CDR3 region. VH sequences: Ab 114 (SEQ ID NO: 1), Ab 011 (SEQ ID NO: 5), Ab 017 (SEQ ID NO: 9), Ab 042 (SEQ ID NO: 13), Ab 092 (SEQ ID NO: 17), Ab 101 (SEQ ID NO: 21), Ab 025 (SEQ ID NO: 25), Ab 109 (SEQ ID NO: 29), Ab 098 (SEQ ID NO: 33), Ab 111 (SEQ ID NO: 37). VL sequences: Ab 114 (SEQ ID NO: 41), Ab 011 (SEQ ID NO: 45), Ab 017 (SEQ ID NO: 49), Ab 042 (SEQ ID NO: 53), Ab 092 (SEQ ID NO: 57), Ab 101 (SEQ ID NO: 61), Ab 025 (SEQ ID NO: 65), Ab 109 (SEQ ID NO: 69), Ab 098 (SEQ ID NO: 73), Ab 111 (SEQ ID NO: 77).

Figure 12:
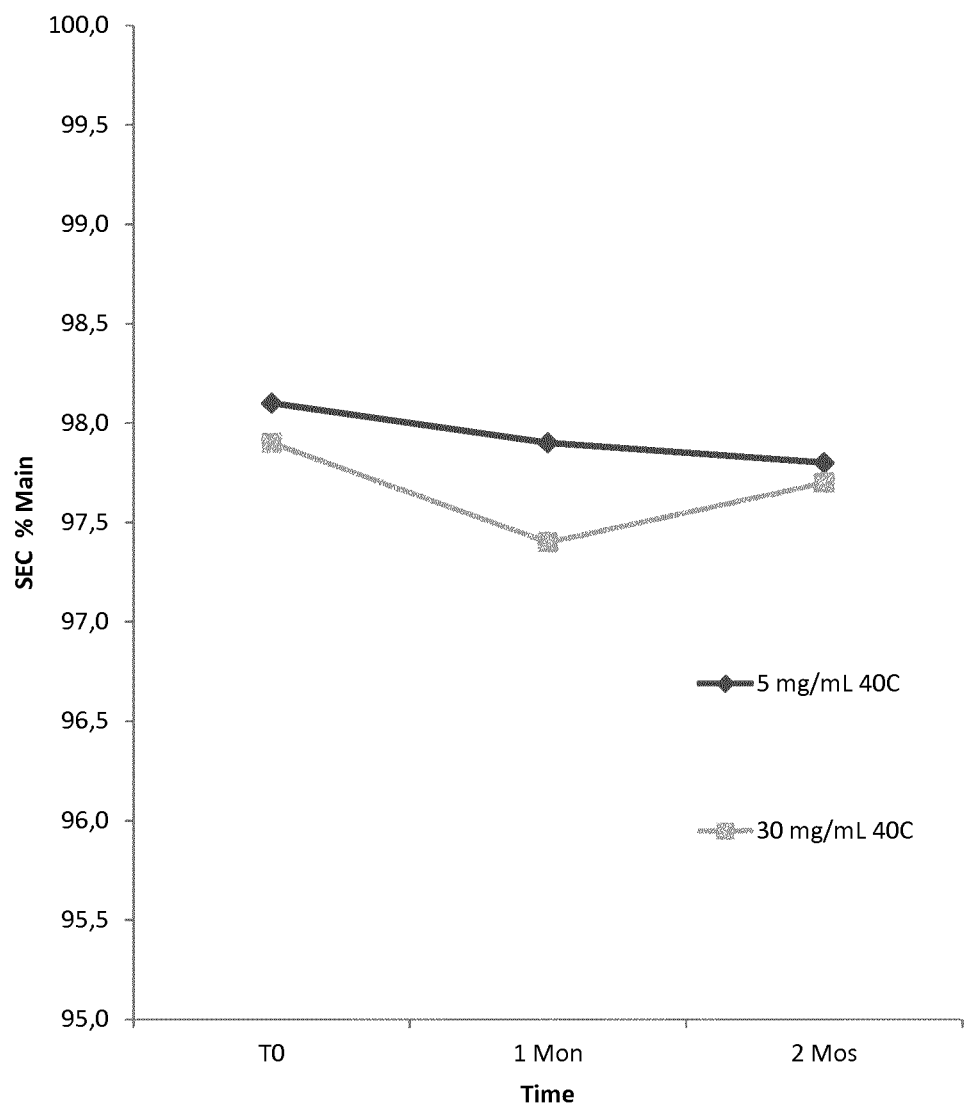

FIG. 12. shows SEC average Percent Main Peak for the 5 mg/mL and 30 mg/mL formulations After Storage at 40° C. for up to 2 Months. See Example 12.

Figure 13:
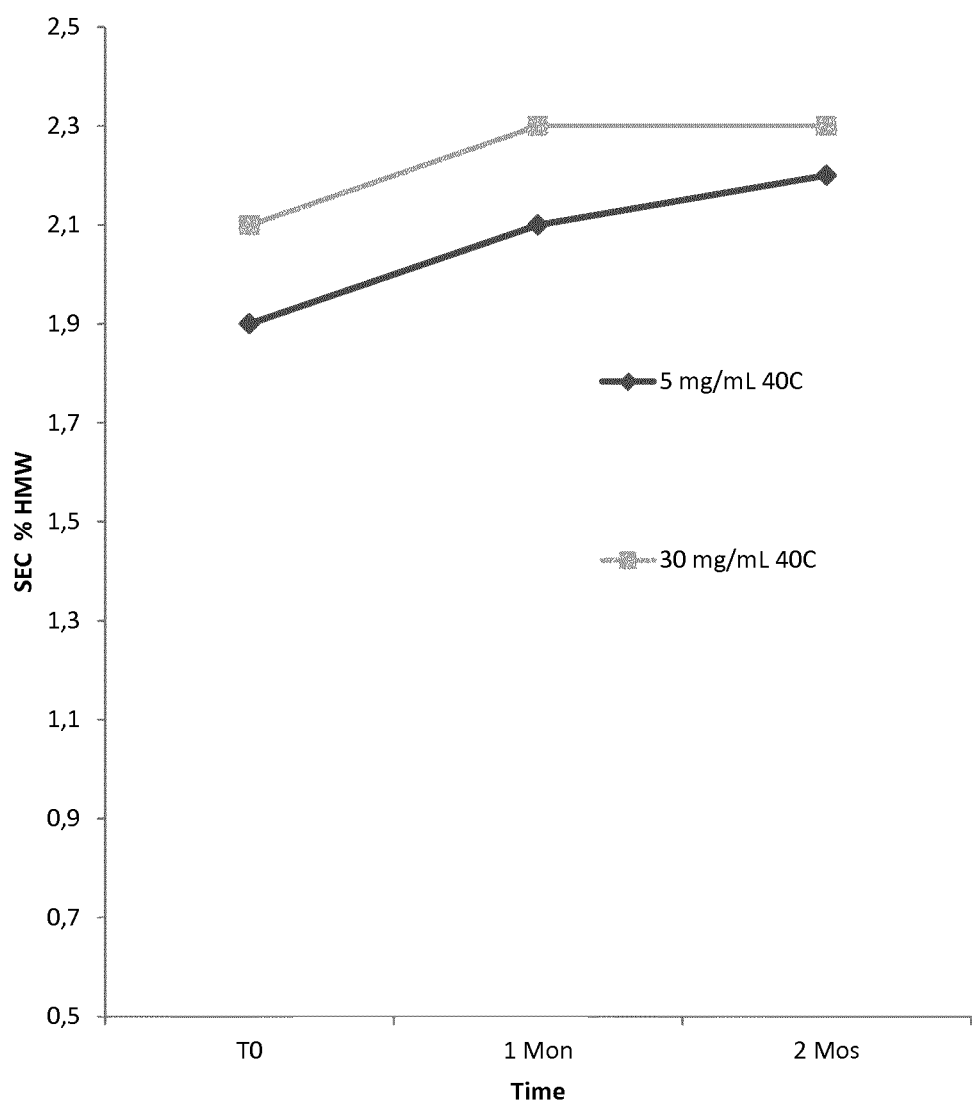

FIG. 13. Shows SEC average percent High Molecular Weight species for the 5 mg/mL and 30 mg/mL formulations after storage at 40° C. for up to 2 Months. See Example 12.

Figure 14:
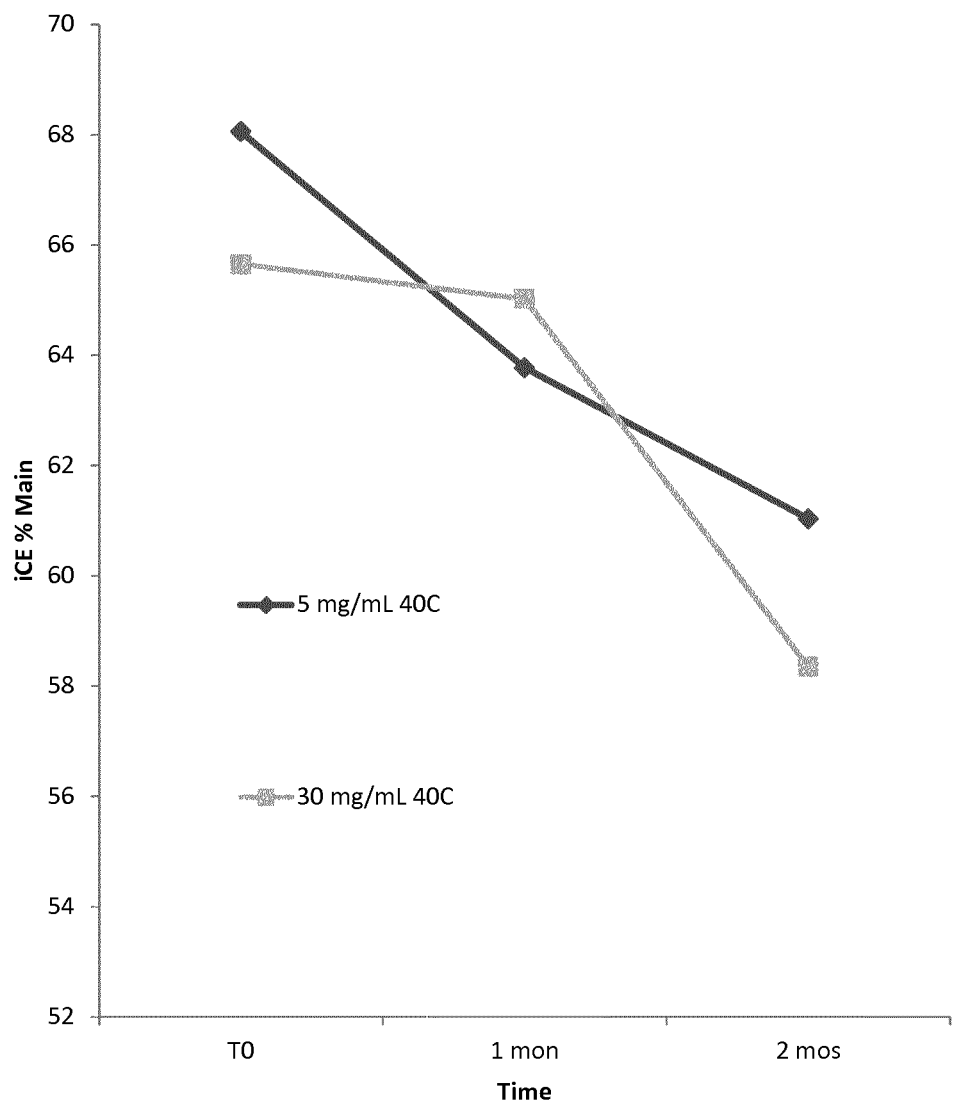

FIG. 14. Shows iCE Percent Main Peak for 5 mg/mL and 30 mg/mL HuMax-TF-ADC formulations after storage at 40° C. for 2 Months. See Example 12.

Figure 15:
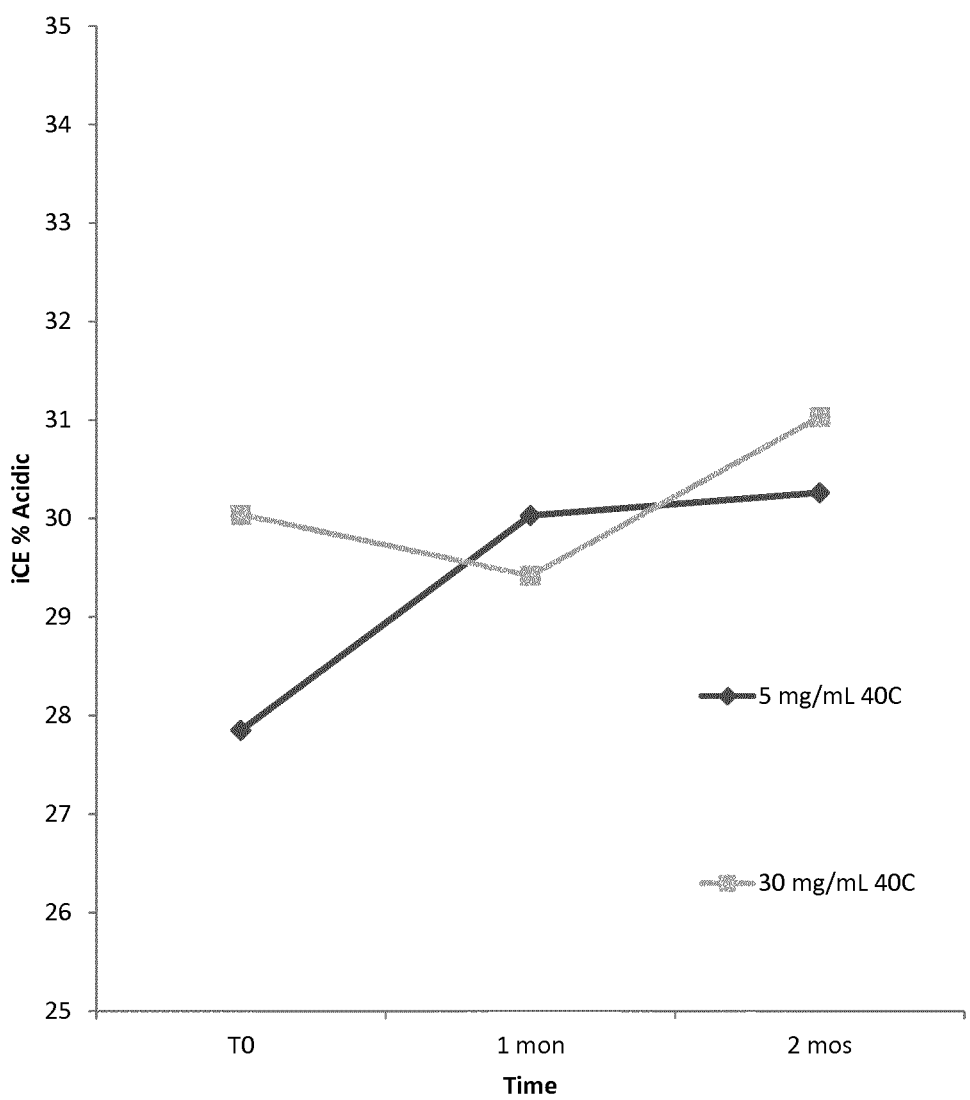

FIG. 15. shows iCE Percent Acidic Species for 5 mg/mL and 30 mg/mL HuMax-TF-ADC formulations after storage at 40° C. for 2 Months. See Example 12.

Figure 16:
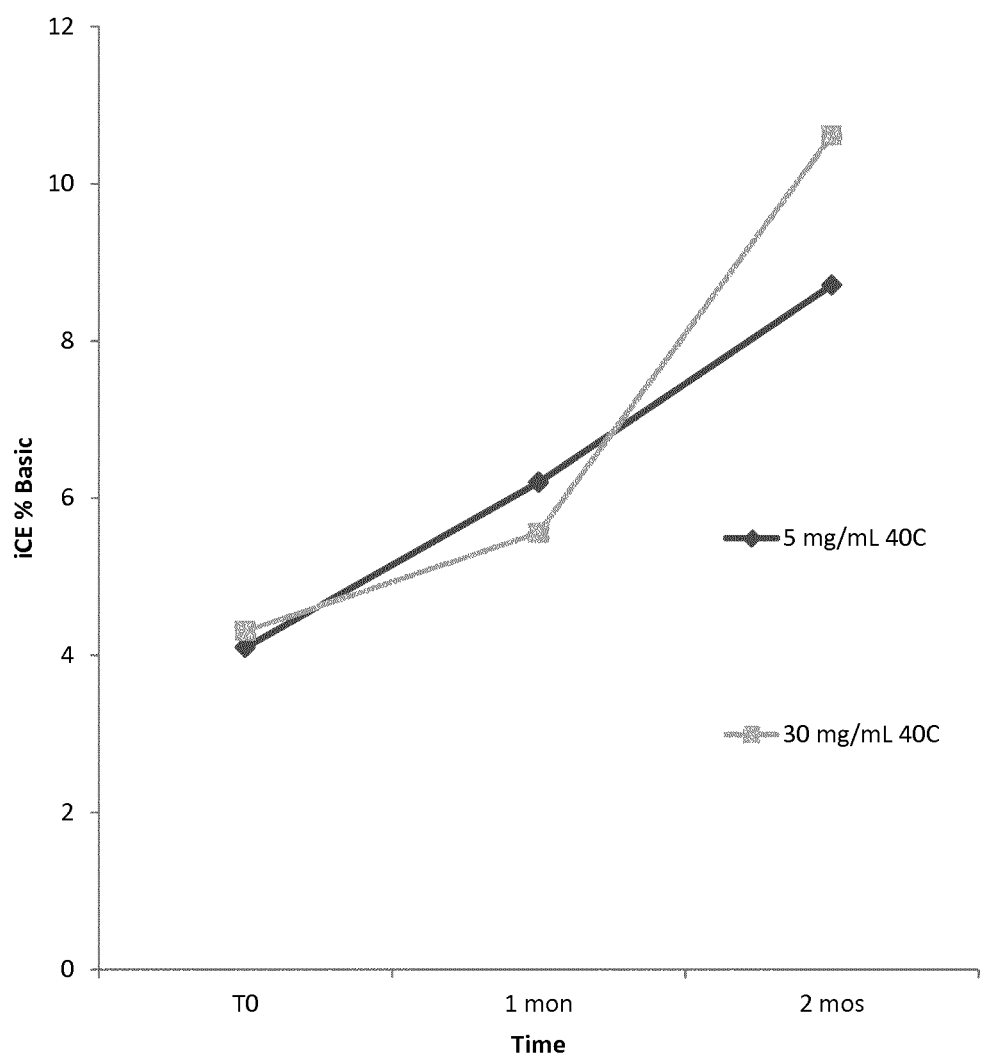

FIG. 16. Shows iCE percent Basic species for 5 mg/ml and 30 mg/ml HuMax-TF-ADC formulations after storage at 40° C. for 2 months. See Example 12.

Figure 17:
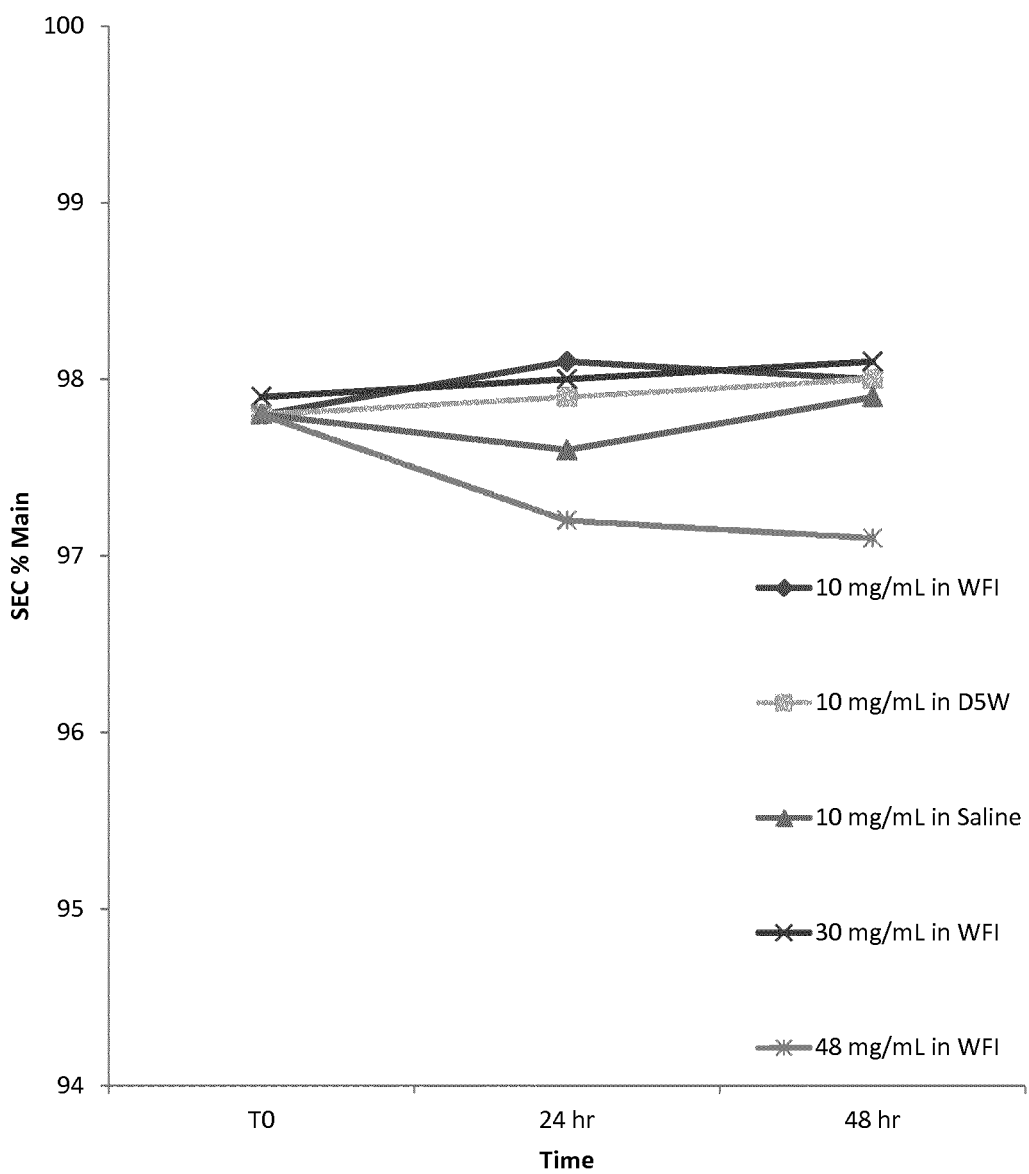

FIG. 17. Shows SEC average % main peak for HuMax-TF-ADC for solution samples stored at 25° C. for up to 48 hours FIG. 18. Shows SEC Average % High Molecular Weight species for solution samples stored at 25° C. for up to 48 hours.

Figure 19:
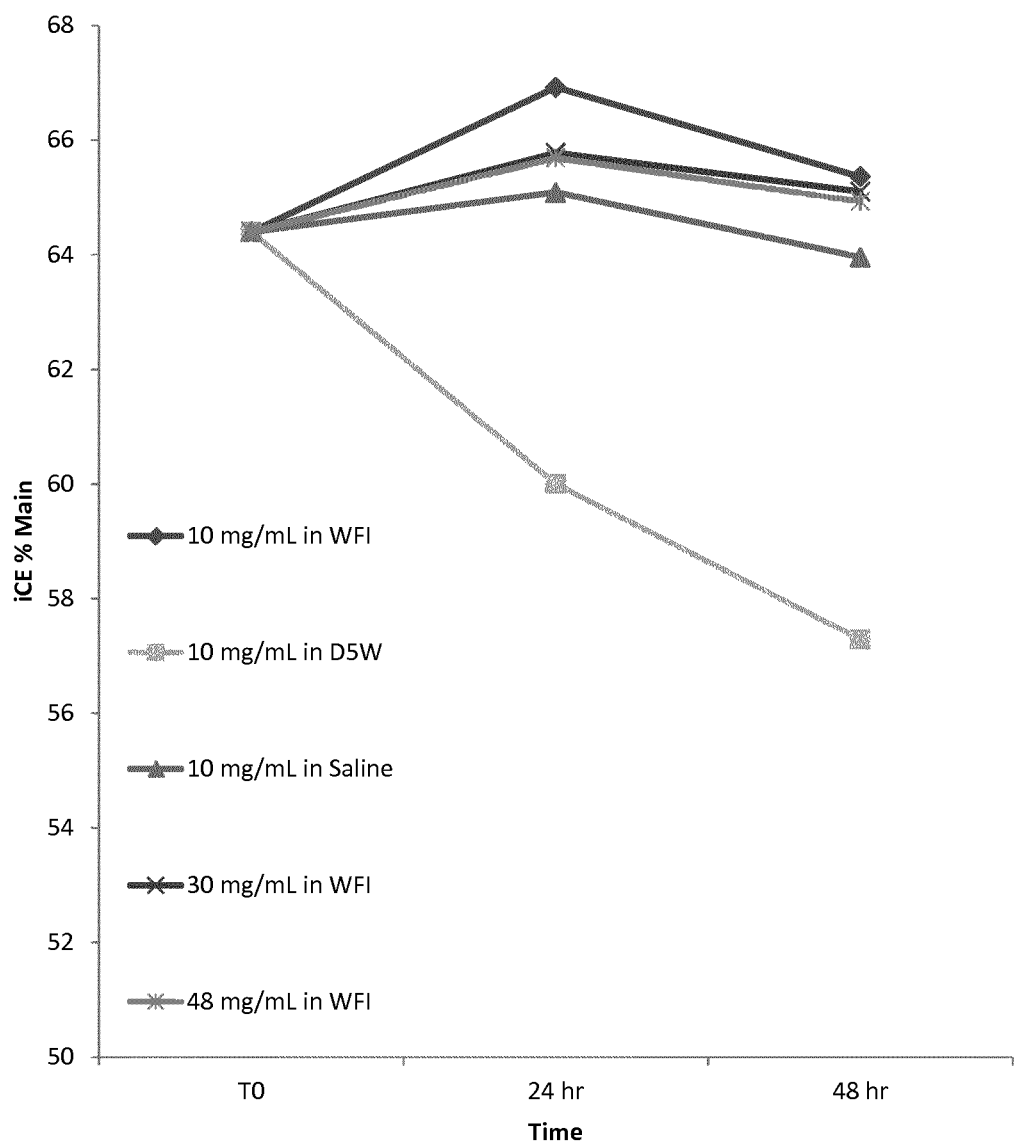

FIG. 19. Shows iCE average % Main Peak for solution samples stored at 25° C. for up to 48 hours.

Figure 20:
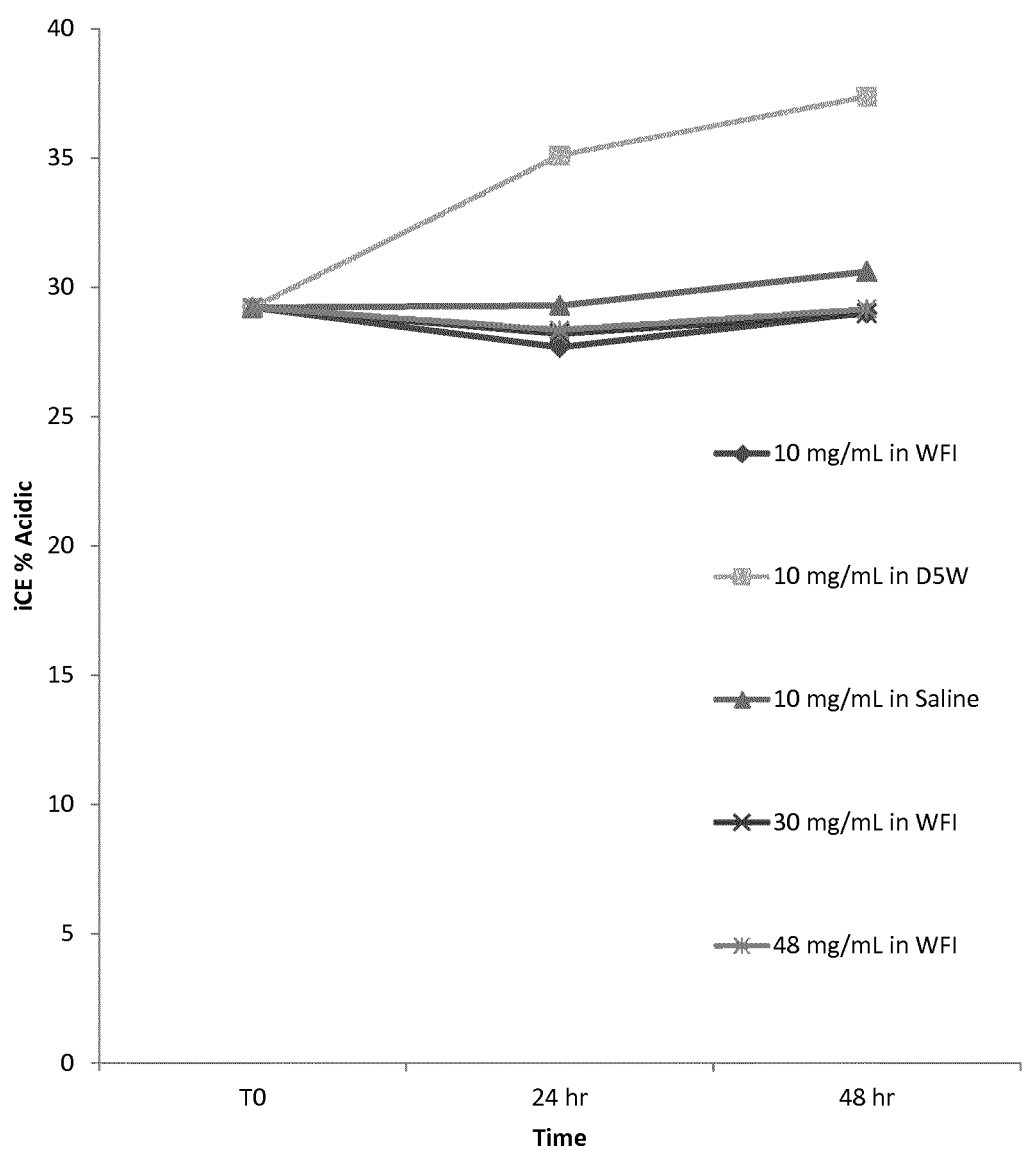

FIG. 20. Shows iCE average % Acidic species for solution samples stored at 25° C. for up to 48 hours.

Figure 21:
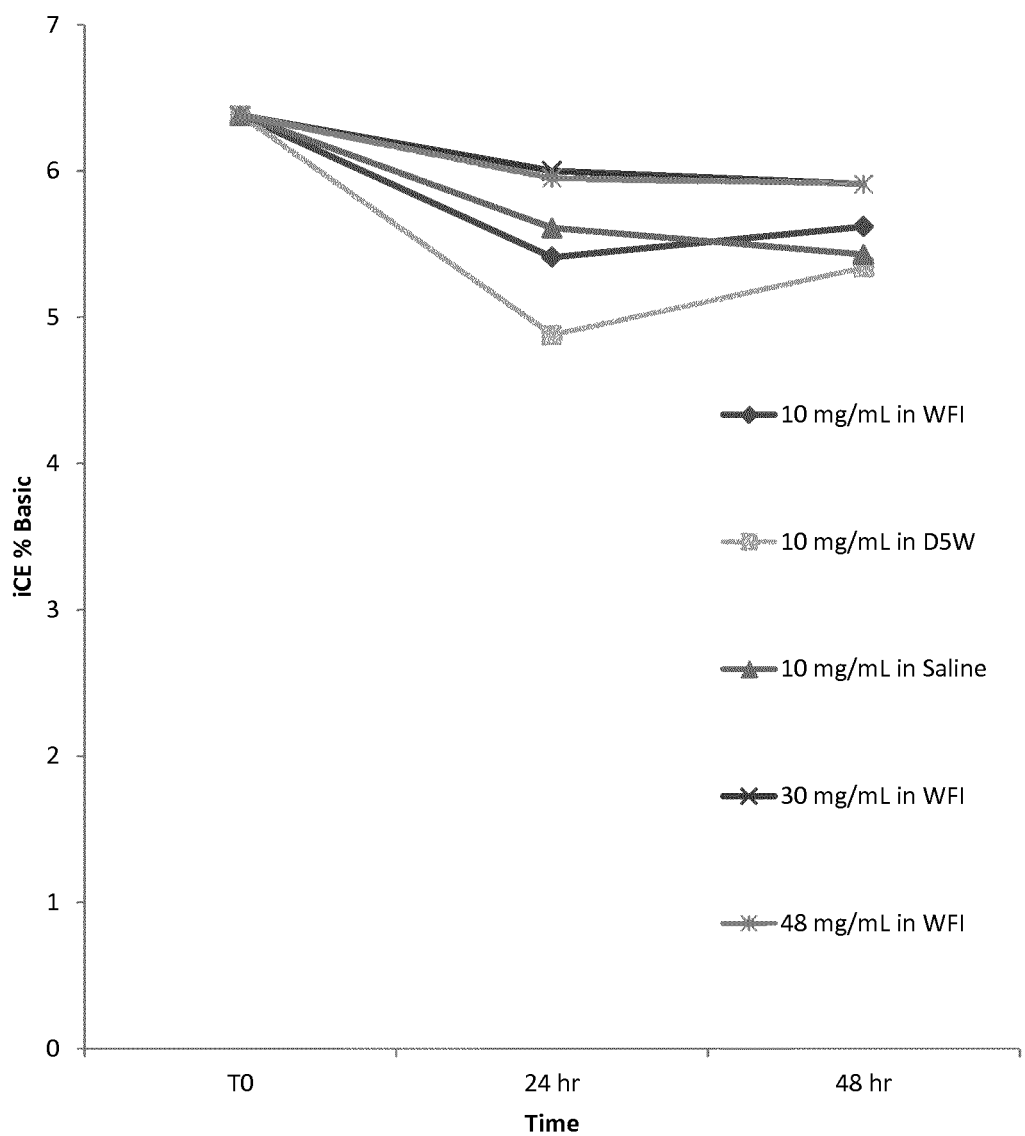

FIG. 21. Shows iCE average % Basic species for solution samples stored at 25° C. for up to 48 hours.

Figure 22:
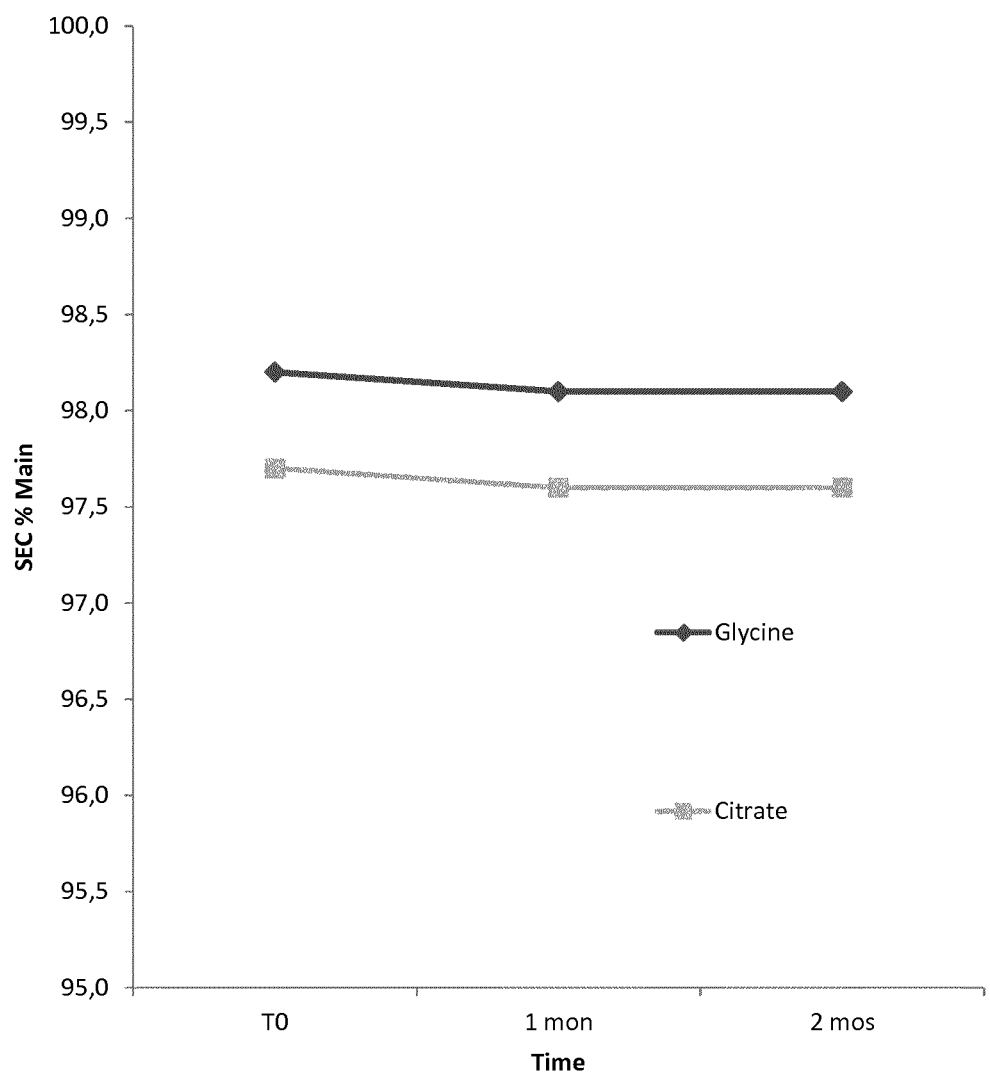

FIG. 22. Shows SEC average Percent Main Peak for lyophilized glycine and citrate formulations stored at 40° C. for up to 2 months.

Figure 23:
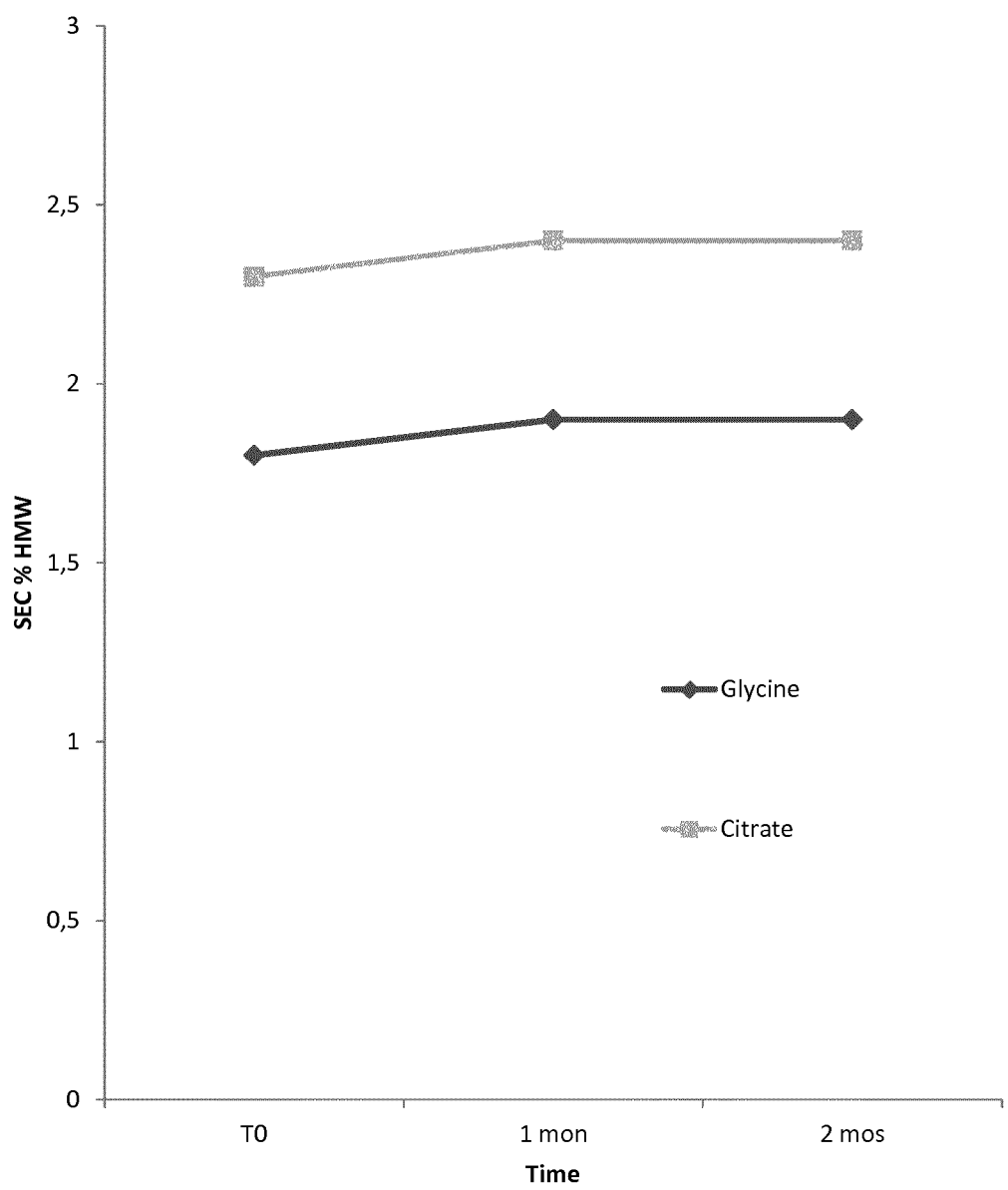

FIG. 23. Shows SEC Average Percent High Molecular Weight species for lyophilized glycine and citrate formulations stored at 40° C. for up to 2 months.

Figure 24:
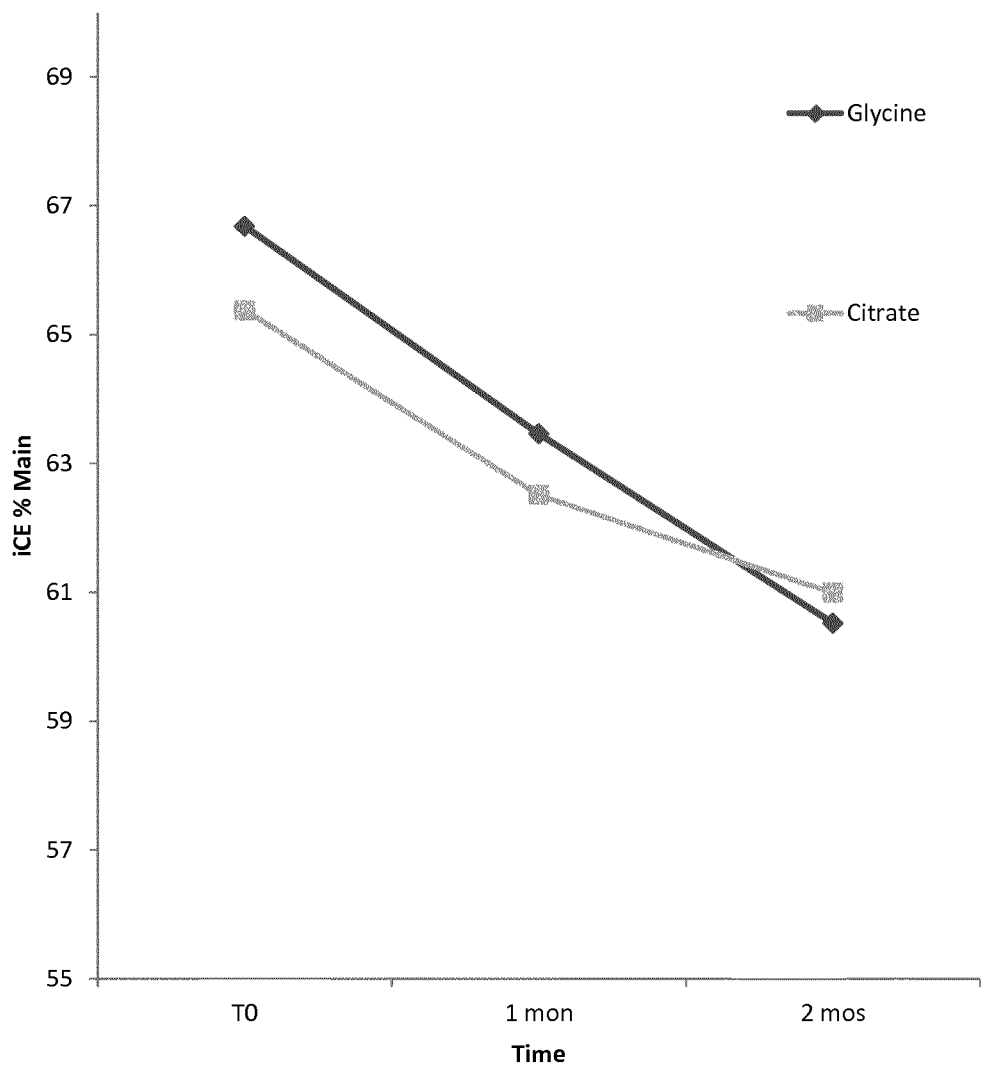

FIG. 24. Shows iCE Percent Main Peak for HuMax-TF-ADC formulations prepared with glycine or citrate after storage at 40° C. for 2 months.

Figure 25:
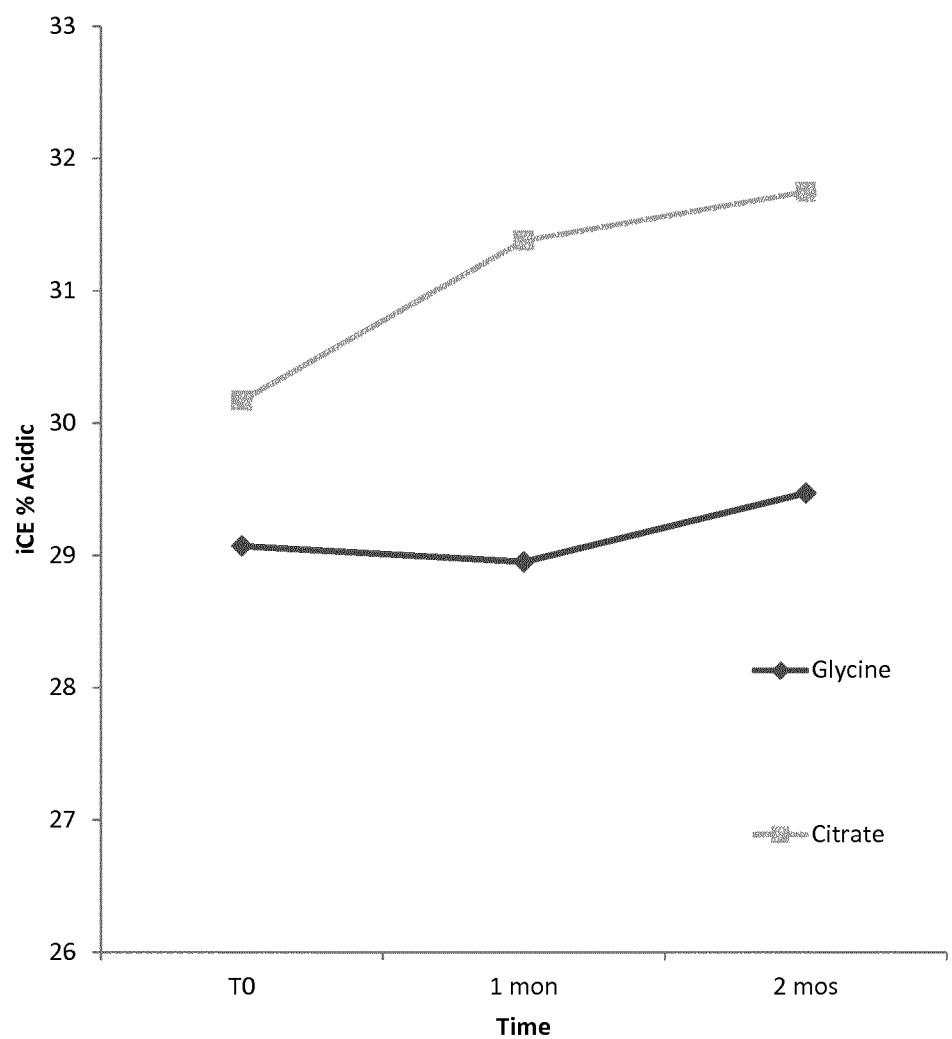

FIG. 25. Shows iCE Percent Acidic species for HuMax-TF-ADC formulations prepared with glycine or citrate after storage at 40° C. for 2 months.

Figure 26:
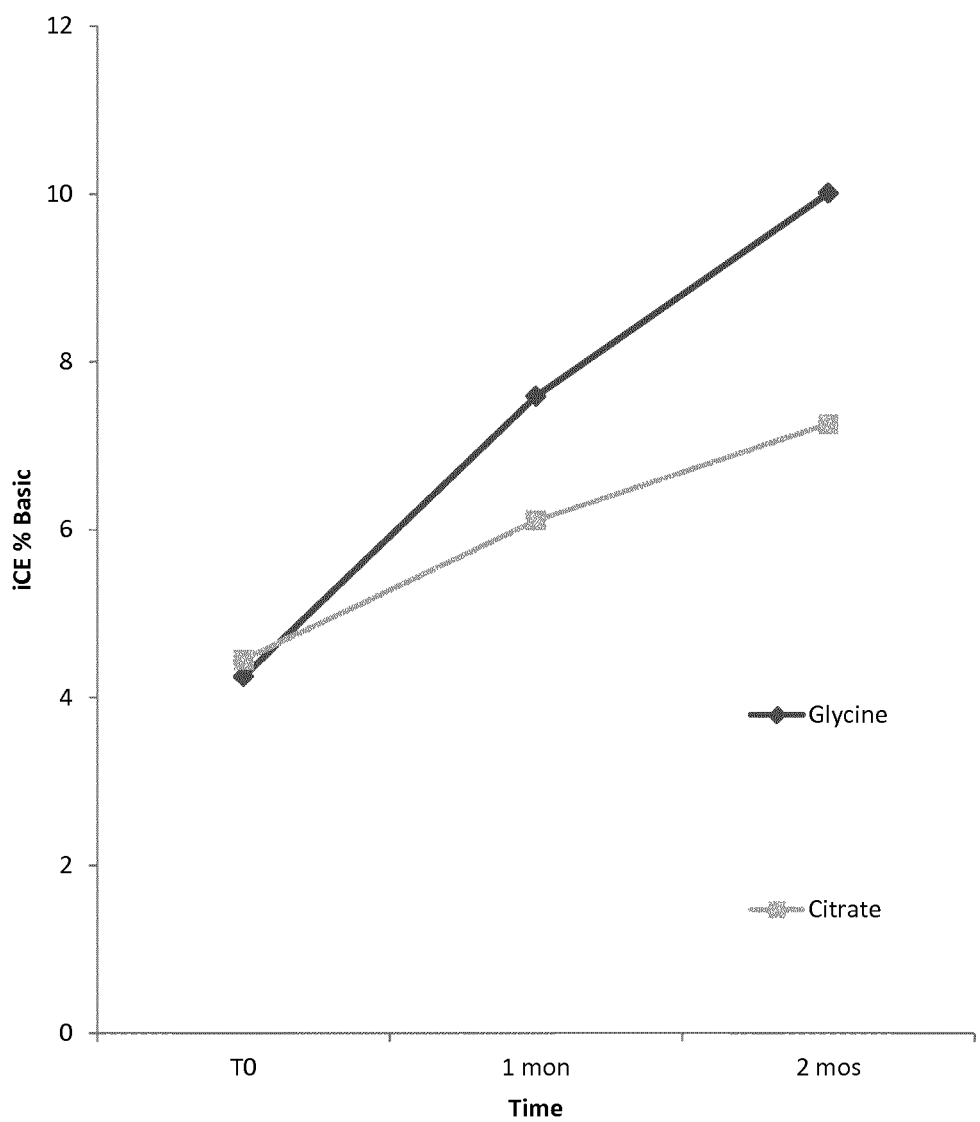

FIG. 26. Shows iCE Percent Basic species for HuMax-TF-ADC formulations prepared with glycine or citrate after storage at 40° C. for 2 months.

Figure 27:
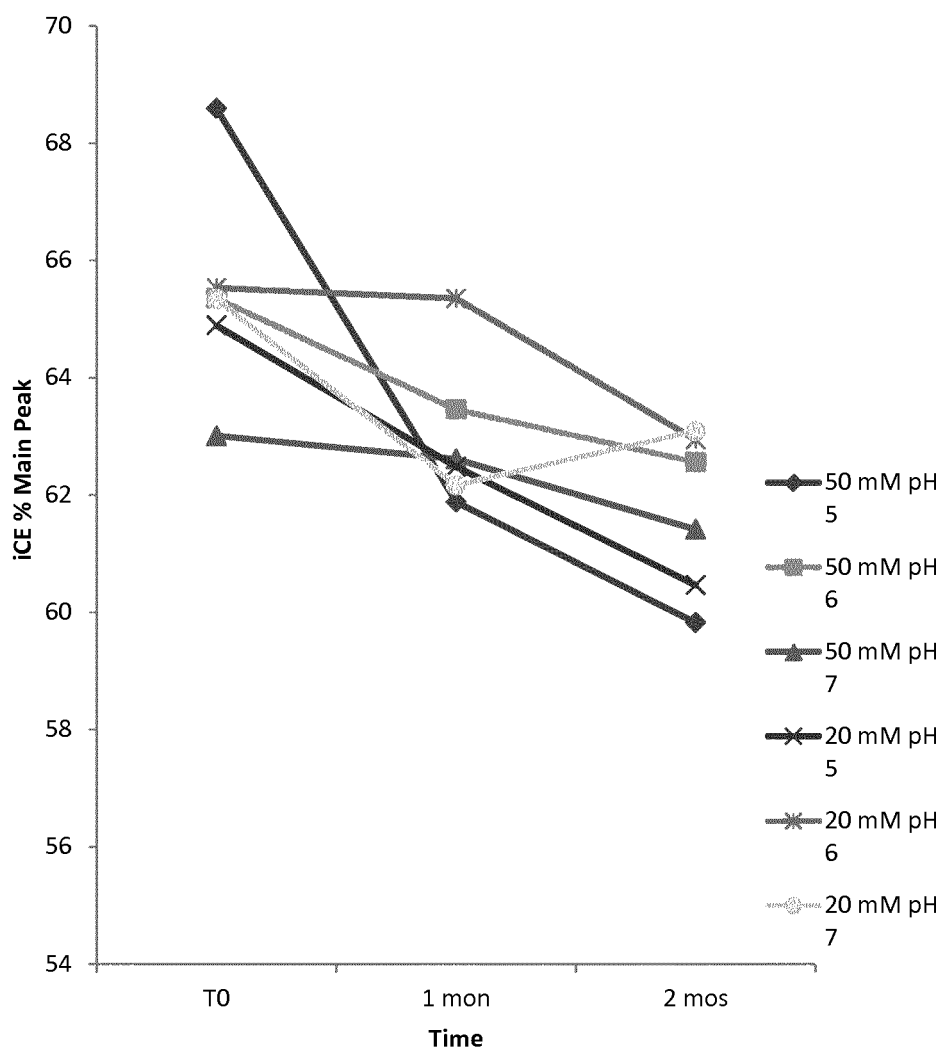

FIG. 27. Shows iCE Percent Main Peak for the 10 mg/mL HuMax-TF-ADC lyophilized formulation prepared with 20 mm or 50 mm histidine at pH 5, or 6, or 7 and stored at 40° C. for 2 months.

Figure 28:
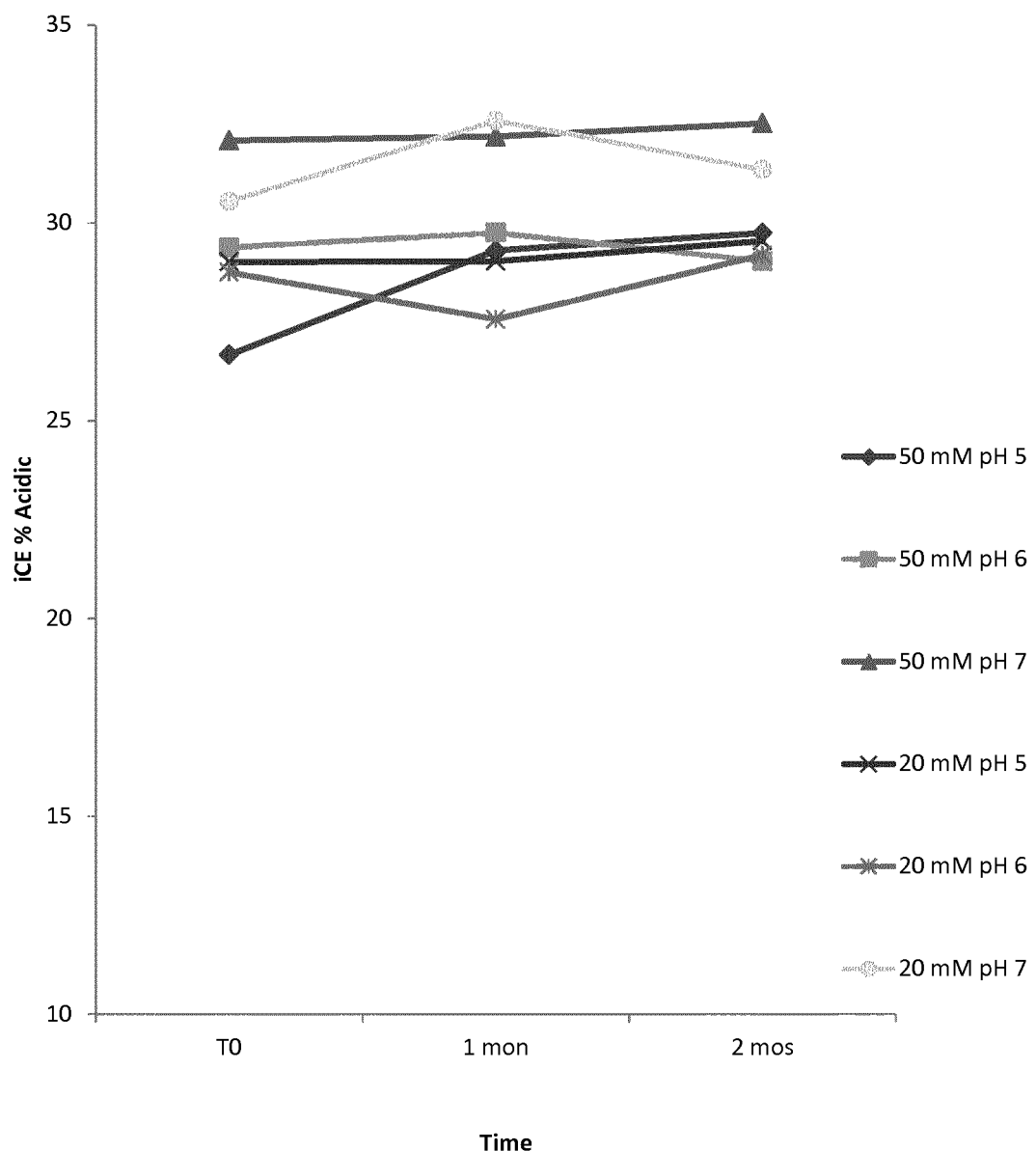

FIG. 28. Shows iCE Percent Acidic species for the 10 mg/mL HuMax-TF-ADC formulation prepared with 20 mM or 50 mM histidine at pH 5, or 6, or 7 and stored at 40° C. for 2 months.

Figure 29:
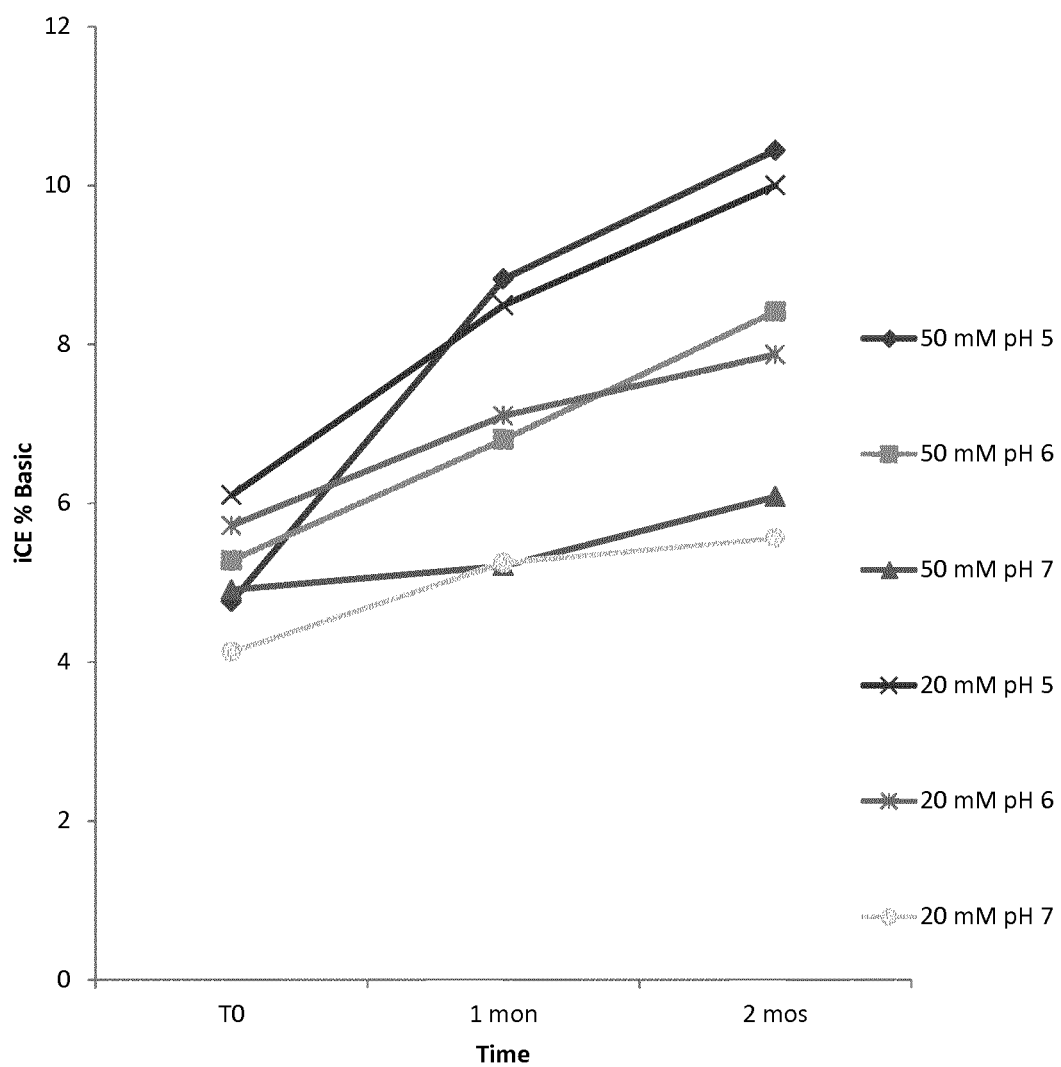

FIG. 29. Shows iCE Percent Basic species for the 10 mg/mL HuMax-TF-ADC formulation prepared with 20 mM or 50 mM histidine at pH 5, or 6, or 7 and stored at 40° C. for 2 months.

Figure 30:
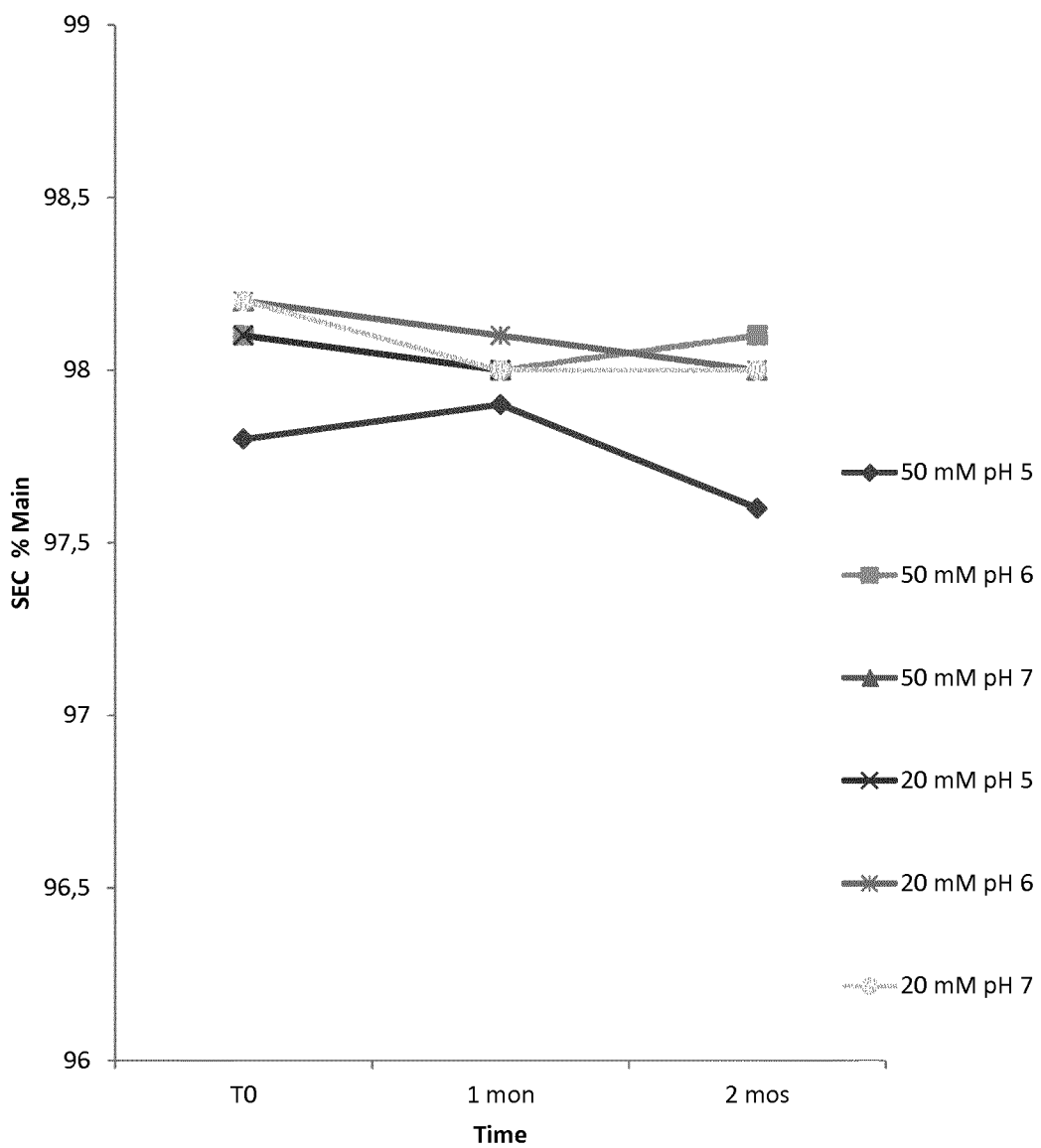

FIG. 30. Shows SEC Percent Main Peak for the 10 mg/mL HuMax-TF-ADC formulation prepared with 20 mM or 50 mM histidine at pH 5, or 6, or 7 and stored at 40° C. for 2 months.

Figure 31:
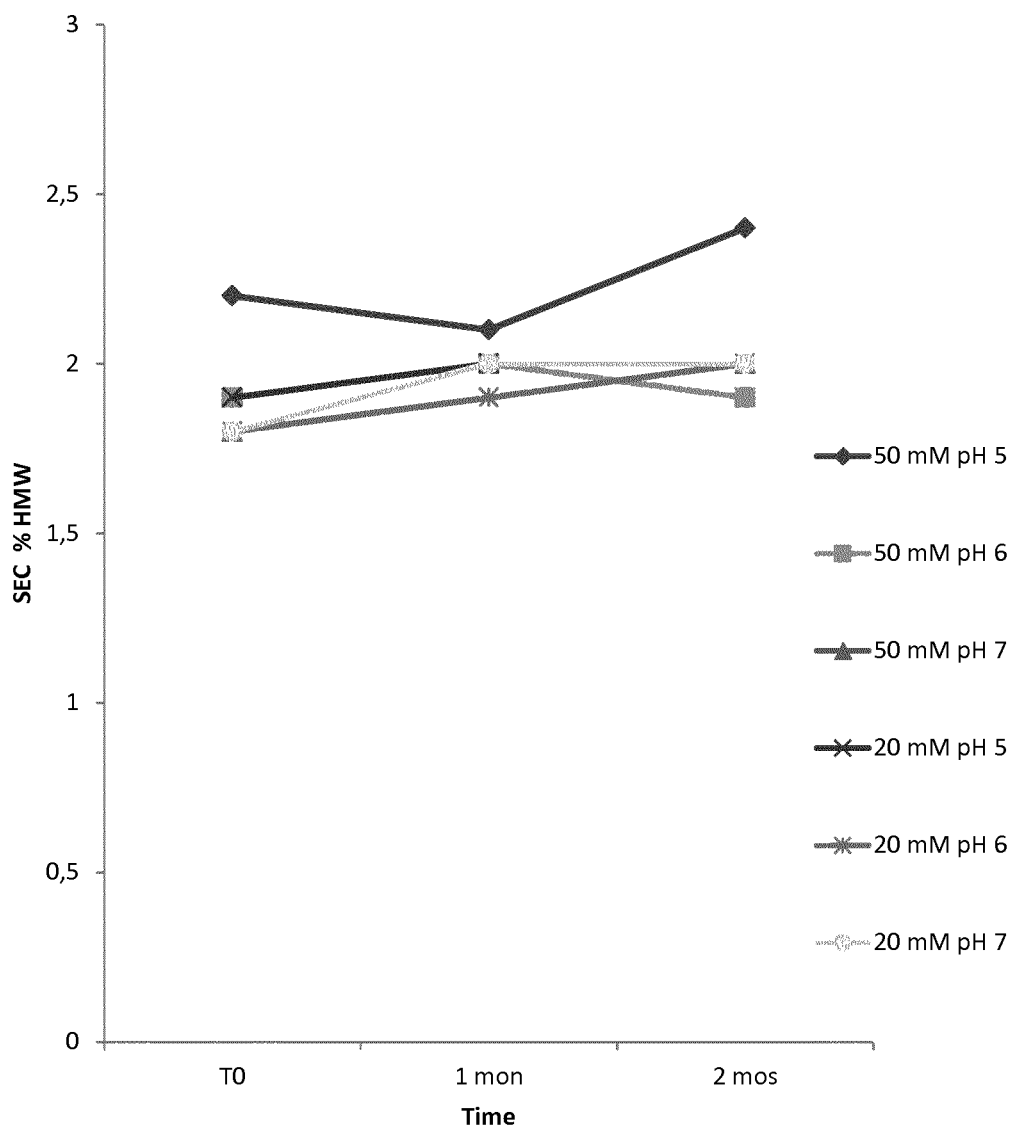

FIG. 31. Shows SEC Average Percent High Molecular Weight species for the 10 mg/mL HuMax-TF-ADC formulation prepared with 20 mM or 50 mM histidine at pH 5, or 6, or 7 and stored at 40° C. for 2 months.

DETAILED DISCLOSURE OF THE INVENTION

Definitions

The terms "lyophilized" and "freeze-dried" are used interchangeably herein and refer to a material that is dehydrated by first freezing and then reducing the surrounding pressure to allow the frozen water in the material to sublimate.

The term "buffer" as used herein denotes a pharmaceutically acceptable buffer. The term "buffer" encompasses those agents which maintain the pH value of a solution, e.g., in an acceptable range and includes, but is not limited to, histidine, TRIS® (tris (hydroxymethyl) aminomethane), citrate, succinate, glycolate and the like, as described herein. Generally, the "buffer" as used herein has a pKa and buffering capacity suitable for the pH range of about 5 to about 7, preferably of about 5.5 to 6.5, such as about pH 6 or about pH 6.0.

The term "bulking agent" includes agents that can provide additional structure to a freeze-dried product (e.g., to provide a pharmaceutically acceptable cake). Commonly used bulking agents include mannitol, glycine, sucrose, and the like. In addition to providing a pharmaceutically acceptable cake, bulking agents also typically impart useful qualities to the lyophilized composition such as modifying the collapse temperature, providing freeze-thaw protection, further enhancing the protein stability over long-term storage, and the like. These agents can also serve as tonicity modifiers.

The term "stabilizer" as used herein includes agents that provide stability to a protein, e.g., serving as a cryoprotectant during freezing and/or a lyoprotectant during a (freeze-) drying or 'dehydration' process. Suitable stabilizers include non-reducing sugars or saccharides and sugar alcohols such as sucrose, trehalose, mannitol, xylitol and the like, as well as amino acids such as glycine, alanine and lysine. Stabilizers can also serve as bulking agents, tonicity-modifying and/or viscosity-increasing agents. The abbreviations "cI EF", "icI EF" and "iCE" are used interchangeably herein and all mean "capillary isoelectric focusing"

A "surfactant" as used herein is a compound that is typically used in pharmaceutical formulations to prevent drug adsorption to surfaces and or aggregation. Furthermore, surfactants lower the surface tension (or interfacial tension) between two liquids or between a liquid and a solid. For example, an exemplary surfactant can significantly lower the surface tension when present at very low concentrations (e.g., 5% w/w or less, such as 3% w/w or less, such as 1% w/w or less). Surfactants are amphiphilic, which means they are usually composed of both hydrophilic and hydrophobic or lipophilic groups, thus being capable of forming micelles or similar self-assembled structures in aqueous solutions. Known surfactants for pharmaceutical use include glycerol monooleat, benzethonium chloride, sodium docusate, phospholipids, polyethylene alkyl ethers, sodium lauryl sulfate and tricaprylin (anionic surfactants); benzalkonium chloride, citrimide, cetylpyridinium chloride and phospholipids (cationic surfactants); and alpha tocopherol, glycerol monooleate, myristyl alcohol, phospholipids, poloxamers, polyoxyethylene alkyl ethers, polyoxyethylene castor oil derivatives, polyoxyethylene sorbintan fatty acid esters, polyoxyethylene sterarates, polyoxyl 15 hydroxystearate, polyoxylglycerides, polysorbates, propylene glycol dilaurate, propylene glycol monolaurate, sorbitan esters sucrose palmitate, sucrose stearate, tricaprylin and TPGS (Nonionic and zwitterionic surfactants).

A "diluent" of interest herein is one which is pharmaceutically acceptable (safe and non-toxic for administration to a human) and is useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

As used herein, a "therapeutic moiety" means a compound which exerts a therapeutic or preventive effect when administered to a subject, particularly when delivered as an ADC as described herein. A "cytotoxic" or "cytostatic" moiety is a compound that is detrimental to (e.g., kills) cells. Some cytotoxic or cytostatic moieties for use in ADCs are hydrophobic, meaning that they have no or only a limited solubility in water, e.g., 1 g/L or less (very slightly soluble), such as 0.8 g/L or less, such as 0.6 g/L or less, such as 0.4 g/L or less, such as 0.3 g/L or less, such as 0.2 g/L or less, such as 0.1 g/L or less (practically insoluble). Exemplary hydrophobic cytotoxic or cytostatic moieties include, but are not limited to, certain microtubulin inhibitors such as auristatin and its derivatives, e.g., MMAF and MMAE.

The term "immunoglobulin" refers to a class of structurally related glycoproteins consisting of two pairs of polypeptide chains, one pair of light (L) chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH or $V_H$) and a heavy chain constant region (CH or $C_H$). The heavy chain constant region typically is comprised of three domains, CH1, CH2, and CH3. Each light chain typically is comprised of a light chain variable region (abbreviated herein as VL or $V_L$) and a light chain constant region (CL or $C_L$). The light chain constant region typically is comprised of one domain, CL. The VH and VL regions may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901 917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of VH CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, a monovalent fragment consisting of the VL, VH, CL and CH1 domains, or a monovalent antibody as described in WO2007059782 (Genmab A/S); (ii) F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., Nature 341, 544 546 (1989)), which consists essentially of a VH domain and also called domain antibodies (Holt et al; Trends Biotechnol. 2003 November; 21(11):484-90); (vi) camelid or nanobodies (Revets et al; Expert Opin Biol Ther. 2005 Jan.; 5(1): 111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423 426 (1988) and Huston et al., PNAS USA 85, 5879 5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention are discussed further herein. It also should be understood that the term antibody, unless specified otherwise, also includes polyclonal antibodies, monoclonal antibodies (mAbs), bi-specific antibodies, antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

In the context of the present invention the term "ADC" refers to an antibody drug conjugate, which in the context of the present invention refers to an anti-TF antibody which is coupled to another moiety as described in the present application. It may e.g. be coupled with a linker to e.g. cysteine or with other conjugation methods to other amino acids. The moiety may e.g. be a drug or a toxin or the like.

An "anti-TF antibody" is an antibody as described above, which binds specifically to the antigen tissue factor or tissue factor antigen. The terms "tissue factor", "TF", "CD142", "tissue factor antigen", "TF antigen" and "CD142 antigen" are used interchangeably herein, and, unless specified otherwise, include any variants, isoforms and species homologs of human tissue factor which are naturally expressed by cells or are expressed on cells transfected with the tissue factor gene. In one embodiment, the tissue factor amino acid sequence comprises the mature form of the Genbank accession NP_001984.1 sequence. Anti-TF antibodies, in particular human anti-TF antibodies, can be produced and characterized according to the methods described in WO2011/157741.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

In a preferred embodiment, the antibody of the ADC or the ADC of the invention is isolated. An "isolated antibody" or "isolated ADC" as used herein, is intended to refer to an antibody or ADC which is substantially free of other antibodies having different antigenic specificities (for instance an isolated antibody that specifically binds to TF is substantially free of antibodies that specifically bind antigens other than TF). An isolated antibody drug conjugate as used herein is intended to refer to an antibody drug conjugate which is also substantially free of "free toxin", wherein "free toxin" is intended to mean toxin which is not conjugated to the antibody. The term "substantially free of" as used in relation to the toxin may in particular mean that less than 5%, such as less than 4%, or less than 3%, or less than 2%, or less than 1.5%, or less than 1%, or less than 0.5% unconjugated drug is present when determined as described in Example 16 in WO2011157741. An isolated antibody or isolated antibody drug conjugate that specifically binds to an epitope, isoform or variant of human TF may, however, have cross-reactivity to other related antigens, for instance from other species (such as tissue factor species homologs). Moreover, an isolated antibody or ADC may be substantially free of other cellular material and/or chemicals. In one embodiment of the present invention, two or more "isolated" monoclonal antibodies or ADCs having different antigen-binding specificities are combined in a well-defined composition. In one embodiment, the two or more isolated monoclonal antibodies or ADC's bind TF at two or more different epitopes. In another embodiment it may be a mix of mAbs or ADC's with binding specificity for TF and one or more mAb or ADC's with a second binding specificity which is not TF.

When used herein in the context of two or more antibodies, the term "competes with" or "cross-competes with" indicates that the antibody competes with another antibody, e.g., a "reference" antibody in binding to an antigen. For example, two or more antibodies competing for binding to TF can be analysed using the assay as described in Example 12 of WO10066803, in which antibody cross-competition studies are made using sandwich ELISA. Briefly, plate wells are coated overnight with an anti-TF antibody to be tested (e.g at +4 degrees Celsius with an anti-TF antibody to be tested using 100 microliter per well of 0.5 or 2 microgram/ml antibody in PBS buffer. The ELISA wells are washed with PBS, blocked for one hour at room temperature with 2% (v/v) serum (e.g., chicken serum,) in PBS and washed again with PBS. Subsequently, 50 microliter anti-TF reference antibody (10 microgram/mL) followed by 50 microliter His-tagged extracellular domain TF (TFECDHis) (0.5 or 1 microgram/ml) is added, and incubated for 1 hour at RT (while shaking). Plates are washed 3 times with PBST (PBS+0.05% tween), and incubated with 1:2000 diluted an anti-his-biotinylated antibody (e.g., anti-his biotin BAM050) for one hour at RT (while shaking). Plates are washed and incubated with streptavidin conjugated to a directly or indirectly detectable compound (e.g., Streptavidin-poly-HRP (Sanquin, Amsterdam, The Netherlands)) for 20 minutes at RT, and washed again. Then, the amount of bound streptavidin is detected and/or quantified. For example, if the indirectly detectable compound is HRP, the reaction is further developed with ABTS (Roche Diagnostics) at RT in the dark, stopped after 15 minutes by adding 2% (w/v) oxalic acid and the absorbance at 405 nm measured. The assay can also be reversed, in that the plate wells can be coated with reference antibody, to which the test antibody is then added in conjunction with the TF. For some pairs of antibodies, competition as in the assay of Example 12 of WO10066803 is only observed when one antibody is coated on the plate and the other is used to compete, and not vice versa. The term "competes with" when used herein is also intended to cover such combinations of antibodies.

The terms "monoclonal antibody" or "monoclonal antibody composition" as used herein refer to a preparation of antibody molecules of single molecular composition. The monoclonal antibody or composition thereof may be drug conjugated antibodies according to the present invention. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or trans-chromosomal non-human animal, such as a transgenic mouse, having a genome comprising a human heavy chain transgene and a light chain transgene, fused to an immortalized cell. Using molecular biology well-known in the art, the cDNA and/or amino acid sequences of a human monoclonal antibody can then be determined so that the antibody, optionally with another isotype can be recombinantly produced.

As used herein, the terms "binding" or "specifically binds" in the context of the binding of an antibody to a pre-determined antigen typically is a binding with an affinity corresponding to a KD, the dissociation equilibrium constant of a particular antibody-antigen interaction, of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the pre-determined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold.

The present invention also provides, in one embodiment, formulations of antibodies comprising functional variants of the VL region, VH region, or one or more CDRs of the antibodies described herein. A functional variant of a VL, VH, or CDR used in the context of an anti-TF antibody still allows the antibody to retain at least a substantial proportion (at least about 50%, 60%, 70%, 80%, 90%, 95% or more) of the affinity/avidity and/or the specificity/selectivity of the parent antibody and in some cases such an anti-TF antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described below.

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment).

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment).

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more such as about 96%, 97% or 98% or 99% of the substitutions in the variant are conservative amino acid residue replacements.

The sequence of CDR variants may differ from the sequence of the CDR of the parent antibody sequences through mostly conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in one or more of the following three tables:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

| Alternative conservative amino acid residue substitution classes | | | |
| --- | --- | --- | --- |
| 1 | A | S | T |
| 2 | D | E | |
| 3 | N | Q | |
| 4 | R | K | |
| 5 | I | L | M |
| 6 | F | Y | W |

| Alternative Physical and Functional Classifications of Amino Acid Residues | |
| --- | --- |
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

More conservative substitution groupings include: valine-leucine-isoleucine, phenylalanine-tyrosine, lysine-arginine, alanine-valine, and asparagine-glutamine. Additional groups of amino acids may also be designed using the principles described in, e.g., Creighton (1984) Proteins: Structure and Molecular Properties (2d Ed. 1993), W.H. Freeman and Company.

In one embodiment of the present invention, conservation in terms of hydropathic/hydrophilic properties and residue weight/size also is substantially retained in a variant CDR as compared to a CDR of an antibody of the examples (e.g., the weight class, hydropathic score, or both of the sequences are at least about 50%, at least about 60%, at least about 70%, at least about 75%, at least about 80%, at least about 85%, at least about 90%, at least about 95%, or more (e.g., about 99%) retained). For example, conservative residue substitutions may also or alternatively be based on the replacement of strong or weak based weight based conservation groups, which are known in the art.

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent peptide.

As used herein, "isotype" refers to the immunoglobulin class (for instance IgG1, IgG2, IgG3, IgG4, IgD, IgA, IgE, or IgM) that is encoded by heavy chain constant region genes.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of an anti-TF antibody drug conjugate may vary according to factors such as the disease state, age, sex, and weight of the individual, and the ability of the anti-TF antibody drug conjugate to elicit a desired response in the individual. A therapeutically effective amount is also one in which any toxic or detrimental effects of the antibody or antibody portion are outweighed by the therapeutically beneficial effects.

Specific Embodiments of the Invention

The present invention is based, at least in part, on the discovery of certain aqueous compositions of anti-TF ADCs which, when lyophilized, provide for stable lyophilized formulations suitable for pharmaceutical purposes and for therapeutic applications of the anti-TF ADCs. The formulations disclosed herein also provide for the option of excluding surfactants such as, e.g., polysorbate 20 and 80, inorganic salts such as, e.g., NaCl.

In order to ensure efficacy and safety during the time course of the shelf life of pharmaceutical compositions, the composition is stability tested. Typically, the stability tests include but are not limited to tests regarding identity, purity and potency of the composition. The stability is tested both at the intended storage temperature and at elevated temperature or temperatures. Purity tests may include but are not limited to SDS-PAGE, CE-SDS, isoelectrofocusing, immunoelectrophoresis, Western blot, reversed-phase chromatography, Size-exclusion chromatography (SEC), ion exchange and affinity chromatography. Other tests may include, but are not limited to: visual appearance such as colour and transparency, particulates, pH, moisture and reconstitution time.

The degradation profile regarding, in particular, purity and potency, during the stability time course is intimately coupled to the composition and/or the formulation of the pharmaceutical product. In particular, proper choice of formulation may significantly change the degradation profile. Surfactants such as for example polysorbate 20 are often added to pharmaceutical compositions to reduce the formation of shelf life limiting degradation products. Typical degradation profiles of monoclonal antibodies and conjugated drug products derived from monoclonal antibodies includes the formation of covalent and non-covalent high molecular weight aggregates, fragments, deamidation and oxidation products. Particularly, de-amidation and oxidation products as well as other acidic species usually develop during the time course of the stability testing. In some cases the acidic species limits the acceptable shelf life of the pharmaceutical composition. The formation of acidic species due to, for example, deamidation, can be tested by, e.g., imaged capillary isoelectrofocusing (icI EF). In other cases the formation of high molecular weight aggregates limits the acceptable shelf life of the pharmaceutical composition. The formation of aggregates may be tested by for example SEC (size exclusion chromatography), DLS, MFI, SDS-PAGE or CE-SDS.

For example, an anti-TF ADC formulation of the invention of pharmaceutically acceptable stability can be one wherein, when stored at a temperature of about 5±3° C. or 25±2° C. for a period of least about 3 months, preferably about 6 months, and more preferably about 12 months or longer, such as 18 months or longer, such as for at least 24 or even 36 months, the percentage of aggregates is less than about 10%, preferably less than about 5%, more preferably less than about 2%, when determined using SEC analysis e.g. according to Example 10. Additionally or alternatively, a stable anti-TF ADC formulation of the invention can be one wherein, when stored at a temperature of about 5±3° C. or 25±2° C. for a period of least about 3 months, preferably about 6 months, and more preferably about 12 months or longer, the changes of main isoform are less than 15%, preferably less than 10%, more preferably less than 8%, most preferably less than 5%, when determined using icI EF analysis, e.g., according to Example 10.

The invention thus provides for the following exemplary and non-limiting lyophilized formulations of anti-TF ADCs, each representing a specific embodiment:

A lyophilized formulation of an anti-tissue factor (TF) antibody-drug conjugate (ADC), the lyophilized formulation obtainable or obtained by lyophilizing an aqueous formulation comprising said anti-TF ADC and pharmaceutically acceptable excipients, wherein the formulation is free of surfactant.

In one embodiment the pharmaceutically acceptable excipients comprises:
a) a buffer which limits pH shifts during the lyophilizing step so that pH is kept between 5 and 7,
b) at least one non-reducing sugar which forms an amorphous phase with the anti-TF ADC in solid state; and
c) at least one bulking agent.

In another embodiment, the invention relates to a lyophilized formulation prepared by lyophilizing an aqueous formulation comprising about 5 g/L to about 30 g/L anti-TF ADC and pharmaceutically acceptable excipients comprising about 20 to about 50 mM histidine buffer having a pH of about 5 to about 7, optionally between about 5.5 and about 6.5; about 10 to about 250 mM sucrose or trehalose; and about 50 mM to about 300 mM mannitol or glycine.

In another embodiment, the invention relates to a lyophilized formulation prepared by lyophilizing an aqueous formulation comprising about 7 g/L to about 20 g/L anti-TF ADC and pharmaceutically acceptable excipients comprising about 20 to about 50 mM histidine buffer having a pH of about 5 to about 7, optionally between about 5.5 and about 6.5; about 10 to about 250 mM sucrose or trehalose; and about 50 mM to about 300 mM mannitol or glycine.

In another embodiment, the invention relates to a lyophilized formulation prepared by lyophilizing an aqueous formulation comprising about 5 g/L to about 30 g/L anti-TF ADC and pharmaceutically acceptable excipients comprising about 25 to about 40 mM histidine buffer, such as about 29 to about 31 mM, having a pH of about 5 to about 7, optionally between about 5.5 and about 6.5; about 10 to about 250 mM sucrose or trehalose; and about 50 mM to about 300 mM mannitol or glycine.

In another embodiment, the invention relates to a lyophilized formulation prepared by lyophilizing an aqueous formulation comprising about 5 g/L to about 30 g/L anti-TF ADC and pharmaceutically acceptable excipients comprising about 20 to about 50 mM histidine buffer having a pH of about 5 to about 7, optionally between about 5.5 and about 6.5; about 50 to 225 mM sucrose or trehalose, such as about 84 to about 165 mM sucrose or trehalose; and about 50 mM to about 300 mM mannitol or glycine.

In another embodiment, the invention relates to a lyophilized formulation prepared by lyophilizing an aqueous formulation comprising about 5 g/L to about 30 g/L anti-TF ADC and pharmaceutically acceptable excipients comprising about 20 to about 50 mM histidine buffer having a pH of about 5 to about 7, optionally between about 5.5 and about 6.5; about 10 to about 250 mM sucrose or trehalose; and about 100 mM to about 274 mM, such as about 158 to about 274, such as about 158 to about 172 mM mannitol or glycine.

In another embodiment, the invention relates to a lyophilized formulation prepared by lyophilizing an aqueous formulation comprising about 5 g/L to about 30 g/L anti-TF ADC and pharmaceutically acceptable excipients comprising about 20 to about 50 mM histidine buffer having a pH between about 5.5 and about 6.5; about 50 to about 225 mM sucrose or trehalose; and about 100 mM to about 274 mM mannitol or glycine.

In another embodiment, the invention relates to a lyophilized formulation prepared by lyophilizing an aqueous formulation comprising about 5 g/L to about 30 g/L anti-TF ADC and pharmaceutically acceptable excipients comprising about 20 to about 50 mM histidine buffer having a pH of about 5 to about 7, optionally between about 5.5 and about 6.5; about 84 to about 165 mM sucrose or trehalose; and about 100 to about 274 mM mannitol or glycine.

In another embodiment, the invention relates to a lyophilized formulation prepared by lyophilizing an aqueous formulation comprising about 5 g/L to about 30 g/L anti-TF ADC and pharmaceutically acceptable excipients comprising about 20 to about 50 mM histidine buffer having a pH of between about 5.5 and about 6.5; about 84 to about 146 mM sucrose; and about 158 mM to about 274 mM mannitol.

In another embodiment, the invention relates to a lyophilized formulation prepared by lyophilizing an aqueous formulation comprising about 5 g/L to about 30 g/L anti-TF ADC and pharmaceutically acceptable excipients comprising about 25 to about 40 mM histidine buffer having a pH between about 5.5 and about 6.5; about 84 to about 92 mM sucrose; and about 158 to about 274 mM mannitol.

In another embodiment, the invention relates to a lyophilized formulation prepared by lyophilizing an aqueous formulation comprising about 7 g/L to about 20 g/L anti-TF ADC and pharmaceutically acceptable excipients comprising about 25 to about 40 mM histidine buffer having a pH between about 5.5 and about 6.5; about 84 to about 92 mM sucrose; and about 100 mM to about 274 mM mannitol or glycine.

In another embodiment, the invention relates to a lyophilized formulation prepared by lyophilizing an aqueous formulation comprising about 7 g/L to about 20 g/L, such as about 9 to about 11 g/L anti-TF ADC and pharmaceutically acceptable excipients comprising about 25 to about 40 mM histidine buffer having a pH of about 5.5 to about 6.5; about 84 to about 92 mM sucrose or trehalose; and about 158 to about 172 mM mannitol or glycine.

In another embodiment, the invention relates to a lyophilized formulation prepared by lyophilizing an aqueous formulation comprising about 9 to about 11 g/L anti-TF ADC and pharmaceutically acceptable excipients comprising about 29 to about 31 mM histidine buffer having a pH of about 5.5 to about 6.5; about 84 to about 92 mM sucrose; and about 158 to about 172 mM mannitol or glycine.

In another embodiment, the invention relates to a lyophilized formulation prepared by lyophilizing an aqueous formulation comprising about 9 to about 11 g/L anti-TF ADC, such as about 10 mg/mL anti-TF ADC, and pharmaceutically acceptable excipients comprising about 30 mM histidine buffer having a pH of about 6; about 88 mM sucrose; and about 165 mM mannitol or glycine.

In another embodiment, the invention relates to a lyophilized formulation prepared by lyophilizing an aqueous formulation comprising about 10 mg/mL anti-TF ADC, and pharmaceutically acceptable excipients comprising about 25 to about 40 mM to histidine buffer, such as 30-35 mM histidine buffer, such as about 30 mM, and having a pH of about 6; about 88 mM sucrose; and about 165 mM mannitol.

In another embodiment, the invention relates to a lyophilized formulation prepared by lyophilizing an aqueous formulation comprising about 9 to about 11 g/L anti-TF ADC, such as about 10 mg/mL anti-TF ADC wherein the anti-TF-ADC is HuMax TF ADC (IgG1, vcMMA), which is an ADC composed of a human monoclonal IgG1, κ antibody 011 against TF conjugated via a protease cleavable valine citrulline linker to the drug monomethyl auristatin E (vcMMAE), and pharmaceutically acceptable excipients comprising about 30 mM histidine buffer having a pH of about 6; about 88 mM sucrose; and about 165 mM mannitol or glycine.

In separate and specific embodiments, the formulations are essentially free of surfactant.

In yet another aspect of the invention the formulations are free of surfactant.

In another embodiment, the invention relates to a lyophilized formulation of an anti-TF ADC, the lyophilized formulation prepared by lyophilizing an aqueous formulation comprising pharmaceutically acceptable excipients comprising: a buffer which limits pH shifts during the lyophilizing step, at least one non-reducing sugar which forms an amorphous phase with the anti-TF ADC in solid state and at least one bulking agent, wherein the anti-TF ADC comprises a drug-linker which is selected from mcMMAF, mcMMAE, vcMMAF and vcMMAE and an anti-TF antibody comprising VH and VL regions selected from the group consisting of: a VH region comprising an amino acid sequence of SEQ ID NO: 5 and a VL region comprising an amino acid sequence of SEQ ID NO: 45; a VH region comprising an amino acid sequence of SEQ ID NO: 33 and a VL region comprising an amino acid sequence of SEQ ID NO: 73; a VH region comprising an amino acid sequence of SEQ ID NO: 37 and a VL region comprising an amino acid sequence of SEQ ID NO: 77; or a VH region comprising an amino acid sequence of SEQ ID NO: 1 and a VL region comprising an amino acid sequence of SEQ ID NO: 41; optionally wherein the lyophilized formulation is essentially free of any surfactant.

In separate and specific embodiments, the antibody-moiety of the ADC of any one of the preceding embodiments comprises the VH and VL CDRs, optionally the VH (SEQ ID NO:5) and VL (SEQ ID NO:45) sequences, of human anti-TF antibody 011, and a drug-linker which is mcMMAE, vcMMAE, vcMMAF or mcMMAF.

In separate and specific embodiments, the antibody-moiety of the ADC of any one of the preceding embodiments comprises the VH and VL CDRs, optionally the VH (SEQ ID NO:33) and VL (SEQ ID NO:73) sequences, of human anti-TF antibody 098, and a drug-linker which is mcMMAE, vcMMAE, vcMMAF or mcMMAF.

In separate and specific embodiments, the antibody-moiety of the ADC of any one of the preceding embodiments comprises the VH and VL CDRs, optionally the VH (SEQ ID NO:37) and VL (SEQ ID NO:77) sequences, of human anti-TF antibody 111, and a drug-linker which is mcMMAE, vcMMAE, vcMMAF or mcMMAF.

In other separate and specific embodiments, the invention provides for a lyophilized formulation of any one of the preceding embodiments, which is essentially free of any polysorbate, optionally of any surfactant.

The invention also provides for a lyophilized formulation consisting essentially of an anti-TF antibody drug conjugate; a buffering agent selected from histidine, citrate and tris; a non-reducing sugar selected from sucrose, trehalose and a combination thereof, and a bulking agent selected from mannitol and glycine. In one embodiment, the anti-TF antibody comprises the VH and VL CDR regions, optionally the VH and VL sequences, of the VH and VL sequences selected from the group consisting of: a VH region comprising an amino acid sequence of SEQ ID NO: 5 and a VL region comprising an amino acid sequence of SEQ ID NO: 45; a VH region comprising an amino acid sequence of SEQ ID NO: 33 and a VL region comprising an amino acid sequence of SEQ ID NO: 73; a VH region comprising an amino acid sequence of SEQ ID NO: 37 and a VL region comprising an amino acid sequence of SEQ ID NO: 77; or a VH region comprising an amino acid sequence of SEQ ID NO: 1 and a VL region comprising an amino acid sequence of SEQ ID NO: 41. In one embodiment, the anti-TF ADC comprises the VH and VL CDRs of SEQ ID NOS:5 and 45, respectively. In one embodiment, the anti-TF ADC comprises the VH and VL CDRs of SEQ ID NOS:33 and 73, respectively. In one embodiment, the anti-TF ADC comprises the VH and VL CDRs of SEQ ID NOS:37 and 77, respectively.

In one specific embodiment of any one of the preceding embodiments, the lyophilized formulation of any one of the preceding embodiments comprises mannitol and sucrose, wherein the weight ratio of mannitol to sucrose is at least about 1, such as between about 1 and about 30, such as between 1 and about 10, such as between about 1 and about 2, such as about 1.

In one specific embodiment of any one of the preceding embodiments, the lyophilized formulation of any one of the preceding embodiments comprises mannitol and trehalose, wherein the weight ratio of mannitol to trehalose is at least about 1, such as between about 1 and about 30, such as between 1 and about 10, such as between about 1 and about 2, such as about 1.

In one specific embodiment of any one of the preceding embodiments, the lyophilized formulation of any one of the preceding embodiments comprises mannitol and sucrose, wherein the weight ratio of mannitol to sucrose is between about 1 and about 10 and the weight ratio of mannitol to ADC is at least about 3, such as between 3 and 30.

The invention also provides for a lyophilized formulation obtainable by lyophilizing an aqueous formulation comprising, optionally consisting of, from about 9 to about 11 g/L anti-TF ADC and about 30 mM histidine; about 88 mM sucrose; and about 165 mM mannitol.

The invention also provides for an aqueous solution suitable for preparing a lyophilized formulation of an anti-TF ADC, comprising
 a. from about 7 to about 20 g/L anti-TF ADC, optionally comprising the VH and VL CDRs or the VH and VL sequences, of anti-TF antibody 011,
 b. about 28 to 34 mM histidine;
 c. about 84 to about 146 mM sucrose;
 d. about 158 to about 274 mM mannitol; or
 e. a combination of a) and any two, three or all of (b) to (d).

The invention also provides for an aqueous solution suitable for preparing a lyophilized formulation of an anti-TF ADC wherein said aqueous solution does not contain a surfactant, said solution comprising:
 a. from about 7 to about 20 g/L anti-TF ADC, optionally comprising the VH and VL CDRs or the VH and VL sequences, of anti-TF antibody 011,
 b. about 28 to 34 mM histidine;
 c. about 84 to about 146 mM sucrose;
 d. about 158 to about 274 mM mannitol; or
 e. a combination of (a) and any two, three or all of (b) to (d).

The invention also provides for an aqueous solution suitable for preparing a lyophilized formulation of an anti-TF ADC, consisting of:
 a. from about 7 to about 20 g/L anti-TF ADC, optionally comprising the VH and VL CDRs or the VH and VL sequences, of anti-TF antibody 011,
 b. about 28 to 34 mM histidine;
 c. about 84 to about 146 mM sucrose;
 d. about 158 to about 274 mM mannitol; or
 e. a combination of (a) and any two, three or all of (b) to (d).

The invention also provides for a pharmaceutically acceptable liquid formulation obtained by reconstituting the lyophilized formulation of any one of the preceding aspects or embodiments in a sterile aqueous diluent. For example, such a liquid formulation may comprise or essentially consist of about 5 g/L to about 30 g/L anti-TF ADC, about 20 to about 50 mM histidine having a pH of about 5 to about 7; about 10 to about 250 mM sucrose or trehalose; and about 50 mM to about 300 mM mannitol or glycine. In one embodiment, the liquid formulation comprises or essentially consists of about 9 to about 11 mg/mL anti-TF ADC, about 28 to about 34 mM histidine, about 84 to about 92 mM sucrose and about 158 to about 274 mM mannitol.

A lyophilized formulation of an anti-TF ADC can be prepared by lyophilizing an aqueous formulation comprising about 9 g/L to about 11 g/L anti-TF ADC and pharmaceutically acceptable excipients comprising: about 30 mM histidine buffer having a pH of about 5.5 to about 6.5; about 88 mM sucrose; and about 165 mM mannitol; wherein the antibody comprises a VH region comprising an amino acid sequence of SEQ ID NO: 5 and a VL region comprising an amino acid sequence of SEQ ID NO: 45; a VH region comprising an amino acid sequence of SEQ ID NO: 33 and a VL region comprising an amino acid sequence of SEQ ID NO: 73; a VH region comprising an amino acid sequence of SEQ ID NO: 37 and a VL region comprising an amino acid sequence of SEQ ID NO: 77; or a VH region comprising an amino acid sequence of SEQ ID NO: 1 and a VL region comprising an amino acid sequence of SEQ ID NO: 41, and wherein the drug is MMAF or MMAE, e.g., a linker-drug which is vcMMAE.

In another embodiment, the lyophilized formulation of the invention contains less than 3.0 wt. % moisture. In another embodiment, the lyophilized formulation of the invention contains less than 2.0 wt. % moisture. In another embodiment, the lyophilized formulation of the invention contains less than 1.0 wt. % moisture. In another embodiment, the lyophilized formulation of the invention contains less than 0.5 wt. % moisture.

In another preferred aspect, any one of the preferred formulations as above comprises an exact quantity or exact quantities of one or more components as comprised therein and/or an exact pH value. In other words, one or more of the terms "about" are deleted in this other preferred aspect of the invention.

Antibody Drug-conjugate

As described herein, the formulations of the invention are suitable for, e.g., anti-TF ADCs. In one embodiment, the lyophilized formulations of the invention comprise an anti-TF ADC conjugated to a therapeutic moiety selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin, carboplatin, duocarmycin A, duocarmycin SA, rachelmycin (CC-1065), or an analog or derivative thereof; pyrrolo[2,1-c][1,4] benzodiazepines (PDBs) or analogues thereof; an antibiotic such as dactinomycin, bleomycin, daunorubicin, doxorubicin, idarubicin, mithramycin, mitomycin, mitoxantrone, plicamycin, anthramycin (AMC)); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP S, *momordica charantia* inhibitor, curcin, crotin, *sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In one embodiment, the antibody is conjugated to a cytotoxic or cytostatic moiety which is a drug selected from the group consisting of dolastatin, maytansine, calicheamicin, duocarmycin, rachelmycin (CC-1065), or an analog, derivative, or prodrug of any thereof.

In one embodiment, the antibody is conjugated to a therapeutic, cytostatic, and/or cytotoxic moiety which is a tubulin inhibitor, DNA interactive compound and/or a kinase inhibitor. In one embodiment, the antibody is conjugated to a hydrophobic compound, such as a hydrophobic tubulin inhibitor, preferably an auristatin, more preferred MMAE or MMAF, and most preferred MMAE.

The drug-loading (or average number of cytostatic or cytotoxic drugs per antibody molecule), is typically 1 to about 8, e.g. p may be from 3-6, such as from 4-6 or from 3-5, or p may be 1, 2, 3, 4, 5, 6, 7 or 8, such as 3, 4 or 5, such as 4.

The ADCs for use in the formulations of the invention typically comprise a linker unit between the cytostatic or cytotoxic drug unit and the antibody unit.

In some embodiments, the linker is cleavable under intracellular conditions, such that the cleavage of the linker releases the drug unit from the antibody in the intracellular environment. In yet another embodiment, the linker unit is not cleavable and the drug is for instance released by antibody degradation. In some embodiments, the linker is cleavable by a cleavable agent that is present in the intracellular environment (e. g. within a lysosome or endosome or caveola). The linker can be, e. g. a peptidyl linker that is cleaved by an intracellular peptidase or protease enzyme, including but not limited to, a lysosomal or endosomal protease. In some embodiments, the peptidyl linker is at least two amino acids long or at least three amino acids long.

Cleaving agents can include cathepsins B and D and plasmin, all of which are known to hydrolyze dipeptide drug derivatives resulting in the release of active drug inside the target cells (see e. g. Dubowchik and Walker, 1999, Pharm. Therapeutics 83:67-123). In a specific embodiment, the peptidyl linker cleavable by an intracellular protease is a Val-Cit (valine-citrulline) linker or a Phe-Lys (phenylalanine-lysine) linker (see e.g. U.S. Pat. No. 6,214,345, which describes the synthesis of doxorubicin with the Val-Cit linker and different examples of Phe-Lys linkers). Examples of the structures of a Val-Cit and a Phe-Lys linker include but are not limited to MC-vc-PAB described below, MC-vc-GABA, MC-Phe-Lys-PAB or MC-Phe-Lys-GABA, wherein MC is an abbreviation for maleimido caproyl, vc is an abbreviation for Val-Cit, PAB is an abbreviation for p-aminobenzylcarbamate and GABA is an abbreviation for γ-aminobutyric acid. An advantage of using intracellular proteolytic release of the therapeutic agent is that the agent is typically attenuated when conjugated and the serum stabilities of the conjugates are typically high.

In some embodiments, the linker unit is not cleavable and the drug is released by antibody degradation (see US 2005/0238649). Typically, such a linker is not substantially sensitive to the extracellular environment.

In a preferred embodiment, the antibody is conjugated to a dolastatin derivative such as an auristatin. Auristatins or auristatin peptide analogs and derivates have been shown to interfere with microtubule dynamics, GTP hydrolysis and nuclear and cellular division and have anti-cancer and anti-fungal activity are described in, e.g., U.S. Pat. Nos. 5,635,483; 5,780,588; U.S. Pat. No. 5,663,149; all of which incorporated here by reference, in their entireties). The auristatin drug moiety is typically attached to the antibody via a linker, through the N (amino) terminus or the C (terminus) of the peptidic drug moiety. Exemplary auristatin embodiments include the N-terminus-linked monomethyl auristatin drug moieties DE and DF, disclosed in Senter et al., Proceedings of the American Association for Cancer Research. Volume 45, abstract number 623, presented Mar. 28, 2004 and described in US 2005/0238649).

In one embodiment the auristatin is monomethyl auristatin E (MMAE):

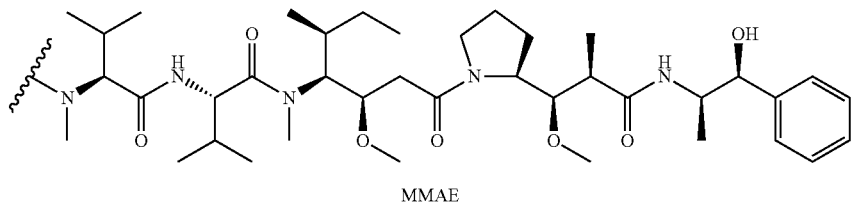 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE wherein the wavy line indicates the attachment site for the linker.

In one embodiment the auristatin is monomethyl auristatin F (MMAF):

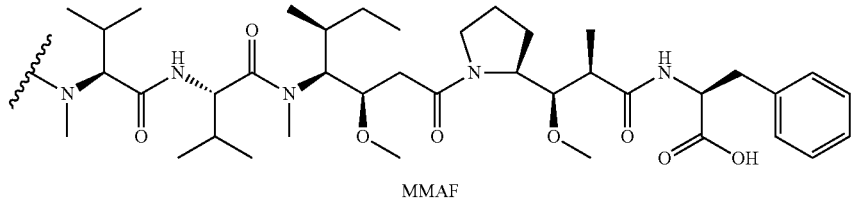

MMAF wherein the wavy line indicates the attachment site for the linker.

In one embodiment the linker is attached to sulphydryl residues of the antibody, e.g., an anti-TF antibody, obtained by (partial) reduction of the antibody.

In one embodiment the linker-auristatin is MC-vc-PAB-MMAF (also designated as vcMMAF) or MC-vc-PAB-MMAE (also designated as vcMMAE):

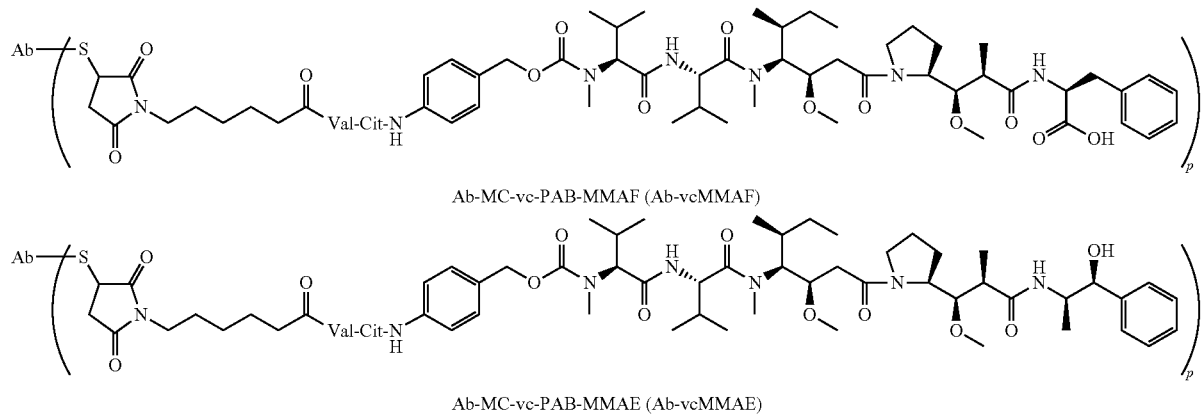

Ab-MC-vc-PAB-MMAF (Ab-vcMMAF)

Ab-MC-vc-PAB-MMAE (Ab-vcMMAE)

wherein p denotes a number of from 1 to 8, e.g. p may be from 3-5, S represents a sulphydryl residue of the antibody, and Ab designates the antibody. In one embodiment the linker-auristatin is vcMMAE.

In one embodiment the linker-conjugate is mcMMAF (where mc/MC is an abbreviation of maleimido caproyl):

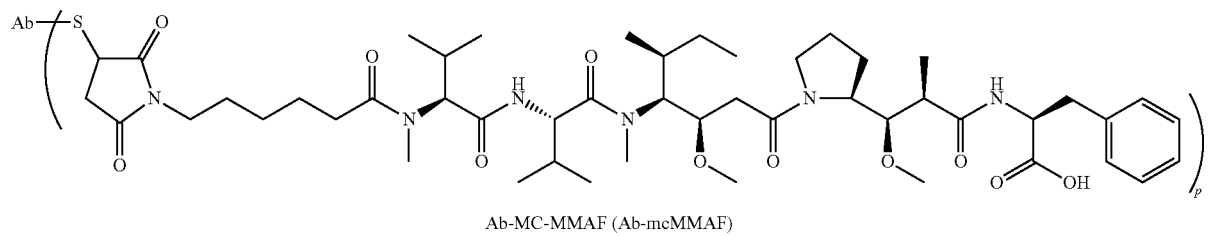

Ab-MC-MMAF (Ab-mcMMAF)

wherein p denotes a number of from 1 to 8, e.g. p may be from 3-5, S represents a sulphydryl residue of the anti-TF antibody, and Ab designates the antibody.

Although generally applicable to any anti-TF antibody, antibodies particularly suitable for the ADC formulations of the invention are those that share one or more physicochemical and/or antigen-binding binding properties with any one or more of the anti-TF antibodies for which VH and VL sequences are provided herein (see Table 1 and FIG. 11), such as, e.g., antibody 011, 098, 114, 017-D12, 042, 092-A09, 101, 025, 109 or 111, such as, e.g., antibody 011, 098 or 111, such as 011. Accordingly, in one embodiment, when conjugated to the drug in question, the resulting ADC can have a pI in the range of about 5 to about 12, such as about 7 to about 10, such as about 8.5 to about 9.5, such as about 8.5 to about 9.0.

In one embodiment, the ADC can bind to the same epitope as and/or comprise one or more CDR sequence of, human antibody 011, optionally in an IgG1,κ format.

In one embodiment, the ADC can bind to the same epitope as and/or comprise one or more CDR sequence of, human antibody 098, optionally in an IgG1,κ format.

In one embodiment, the ADC can bind to the same epitope as and/or comprise one or more CDR sequence of, human antibody 114, optionally in an IgG1,κ format.

In one embodiment, the ADC can bind to the same epitope as and/or comprise one or more CDR sequence of, human antibody 017-D12 optionally in an IgG1,κ format.

In one embodiment, the ADC can bind to the same epitope as and/or comprise one or more CDR sequence of, human antibody 042, optionally in an IgG1,κ format.

In one embodiment, the ADC can bind to the same epitope as and/or comprise one or more CDR sequence of, human antibody 092-A09, optionally in an IgG1,κ format.

In one embodiment, the ADC can bind to the same epitope as and/or comprise one or more CDR sequence of, human antibody 101, optionally in an IgG1,κ format.

In one embodiment, the ADC can bind to the same epitope as and/or comprise one or more CDR sequence of, human antibody 025, optionally in an IgG1,κ format.

In one embodiment, the ADC can bind to the same epitope as and/or comprise one or more CDR sequence of, human antibody 109 optionally in an IgG1,κ format.

In one embodiment, the ADC can bind to the same epitope as and/or comprise one or more CDR sequence of, human antibody 111, optionally in an IgG1,κ format.

In one embodiment the antibody is an anti-TF antibody competing for tissue factor binding with a reference antibody comprising a VH region comprising the sequence of SEQ ID NO:33 and a VL region comprising the sequence of SEQ ID NO:73, or with an antibody comprising a VH region comprising the sequence of SEQ ID NO:1 and a VL region comprising the sequence of SEQ ID NO:41, or with an antibody comprising a VH region comprising the sequence of SEQ ID NO:5 and a VL region comprising the sequence of SEQ ID NO:45, or with an antibody comprising a VH region comprising the sequence of SEQ ID NO:9 and a VL region comprising the sequence of SEQ ID NO:49, or with an antibody comprising a VH region comprising the sequence of SEQ ID NO:13 and a VL region comprising the sequence of SEQ ID NO:53, or with an antibody comprising a VH region comprising the sequence of SEQ ID NO:17 and a VL region comprising the sequence of SEQ ID NO:57, or with an antibody comprising a VH region comprising the sequence of SEQ ID NO:21 and a VL region comprising the sequence of SEQ ID NO:61, or with an antibody comprising a VH region comprising the sequence of SEQ ID NO:25 and a VL region comprising the sequence of SEQ ID NO:65, or with an antibody comprising a VH region comprising the sequence of SEQ ID NO:29 and a VL region comprising the sequence of SEQ ID NO:69, or with an antibody comprising a VH region comprising the sequence of SEQ ID NO:37 and a VL region comprising the sequence of SEQ ID NO:77. In one embodiment the antibody is an anti-TF antibody competing for tissue factor binding with a reference antibody comprising a VH region comprising the sequence of SEQ ID NO:5 and a VL region comprising the sequence of SEQ ID NO:45.

In one embodiment the anti-TF antibody comprises: a VH region comprising the CDR1, 2 and 3 sequences of SEQ ID NO:34, 35 and 36 and a VL region comprising the CDR1, 2 and 3 sequences of SEQ ID NO:74, 75 and 76; or a VH region comprising the CDR1, 2 and 3 sequences of SEQ ID NO:2, 3 and 4 and a VL region comprising the CDR1, 2 and 3 sequences of SEQ ID NO:42, 43 and 44; or a VH region comprising the CDR1, 2 and 3 sequences of SEQ ID NO:6, 7 and 8 and a VL region comprising the CDR1, 2 and 3 sequences of SEQ ID NO:46, 47 and 48; or a VH region comprising the CDR1, 2 and 3 sequences of SEQ ID NO:10, 11 and 12 and a VL region comprising the CDR1, 2 and 3 sequences of SEQ ID NO:50, 51 and 52, or a VH region comprising the CDR1, 2 and 3 sequences of SEQ ID NO: 14, 15 and 16 and a VL region comprising the CDR1, 2 and 3 sequences of SEQ ID NO:54, 55 and 56; or a VH region comprising the CDR1, 2 and 3 sequences of SEQ ID NO:18, 19 and 20 and a VL region comprising the CDR1, 2 and 3 sequences of SEQ ID NO:58, 59 and 60; or a VH region comprising the CDR1, 2 and 3 sequences of SEQ ID NO:22, 23 and 24 and a VL region comprising the CDR1, 2 and 3 sequences of SEQ ID NO:62, 63 and 64, or a VH region comprising the CDR1, 2 and 3 sequences of SEQ ID NO:26, 27 and 28 and a VL region comprising the CDR1, 2 and 3 sequences of SEQ ID NO:66, 67 and 68; or a VH region comprising the CDR1, 2 and 3 sequences of SEQ ID NO:30, 31 and 32 and a VL region comprising the CDR1, 2 and 3 sequences of SEQ ID NO:70, 71 and 72; or a VH region comprising the CDR1, 2 and 3 sequences of SEQ ID NO:38, 39 and 40 and a VL region comprising the CDR1, 2 and 3 sequences of SEQ ID NO:78, 79 and 80; or a variant of any of said antibodies, wherein said variant preferably has at most 1, 2 or 3 amino-acid modifications, more preferably amino-acid substitutions, such as conservative amino-acid substitutions in said sequences. In one embodiment, the anti-TF antibody comprises: a VH region comprising the CDR1, 2 and 3 sequences of SEQ ID NO:6, 7 and 8 and a VL region comprising the CDR1, 2 and 3 sequences of SEQ ID NO:46, 47 and 48, or a variant which has at most 1, 2 or 3 amino-acid modifications, more preferably amino-acid substitutions, such as conservative amino-acid substitutions in said sequences.

In one embodiment the anti-TF antibody comprises a VH having at least 80% identity, such as at least 90%, at least 95%, or at least 98% or 100% identity to a VH region sequence selected from the group consisting of: SEQ ID NO:33, 1, 5, 9, 13, 17, 21, 25, 37 and 29; or at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO: 1, 5, 9, 13, 17, 21, 25, 33, 37 and 29.

In one embodiment, the anti-TF antibody comprises a VL having at least 80% identity, such as at least 90%, at least 95%, or at least 98% or 100% identity to a VL region sequence selected from the group consisting of: SEQ ID NO:41, 45, 49, 53, 57, 61, 65, 73, 77 and 69; or at most 20, such as 15, or 10, or 5, 4, 3, 2 or 1 amino-acid modifications, more preferably amino-acid substitutions, such as conservative amino-acid substitutions as compared to a VH region sequence selected from the group consisting of: SEQ ID NO:41, 45, 49, 53, 57, 61, 65, 73, 77 and 69.

In separate and specific embodiments, the anti-TF antibody is the full-length, fully human monoclonal IgG1,κ antibody Anti-TF HuMab 092-A09, Anti-TF HuMab 101, Anti-TF HuMab 025, Anti-TF HuMab 109, Anti-TF HuMab 017-D12, Anti-TF HuMab 114, Anti-TF HuMab 042, Anti-TF HuMab 011, Anti-TF HuMab 098 or Anti-TF HuMab 111 or an antibody comprising the VH and VL CDRs of any thereof, or an antibody comprising the VH and VL sequence thereof. In one particular embodiment, the anti-TF antibody is anti-TF HuMab 011, or an antibody comprising the VH CDR1, 2, 3 and VL CDR 1, 2, 3 sequences thereof, or an antibody comprising the VH and VL sequence thereof. In one particular embodiment, the anti-TF antibody is anti-TF HuMab 098, or an antibody comprising the VH CDR1, 2, 3 and VL CDR 1, 2, 3 sequences thereof, or an antibody comprising the VH and VL sequence thereof. In one particular embodiment, the anti-TF antibody is anti-TF HuMab 111, or an antibody comprising the VH CDR1, 2, 3 and VL CDR 1, 2, 3 sequences thereof, or an antibody comprising the VH and VL sequence thereof.

Table 1 sets out the specific sequence identifiers (SEQ ID No) relating to the VH (1A) and VL (1B) sequences of these antibodies.

TABLE 1A

| VH-region | |
|---|---|
| SEQ ID No: 1 | VH 114 |
| SEQ ID No: 2 | VH 114, CDR1 |
| SEQ ID No: 3 | VH 114, CDR2 |
| SEQ ID No: 4 | VH 114, CDR3 |
| SEQ ID No: 5 | VH 011 |
| SEQ ID No: 6 | VH 011, CDR1 |
| SEQ ID No: 7 | VH 011, CDR2 |
| SEQ ID No: 8 | VH 011, CDR3 |
| SEQ ID No: 9 | VH 017-D12 |
| SEQ ID No: 10 | VH 017-D12, CDR1 |
| SEQ ID No: 11 | VH 017-D12, CDR2 |
| SEQ ID No: 12 | VH 017-D12, CDR3 |
| SEQ ID No: 13 | VH 042 |
| SEQ ID No: 14 | VH 042, CDR1 |
| SEQ ID No: 15 | VH 042, CDR2 |
| SEQ ID No: 16 | VH 042, CDR3 |
| SEQ ID No: 17 | VH 092-A09 |
| SEQ ID No: 18 | VH 092-A09, CDR1 |
| SEQ ID No: 19 | VH 092-A09, CDR2 |
| SEQ ID No: 20 | VH 092-A09, CDR3 |
| SEQ ID No: 21 | VH 101 |
| SEQ ID No: 22 | VH 101, CDR1 |
| SEQ ID No: 23 | VH 101, CDR2 |
| SEQ ID No: 24 | VH 101, CDR3 |
| SEQ ID No: 25 | VH 025 |
| SEQ ID No: 26 | VH 025, CDR1 |
| SEQ ID No: 27 | VH 025, CDR2 |
| SEQ ID No: 28 | VH 025, CDR3 |
| SEQ ID No: 29 | VH 109 |
| SEQ ID No: 30 | VH 109, CDR1 |

TABLE 1A-continued

VH-region

| | |
|---|---|
| SEQ ID No: 31 | VH 109, CDR2 |
| SEQ ID No: 32 | VH 109, CDR3 |
| SEQ ID No: 33 | VH 098 |
| SEQ ID No: 34 | VH 098, CDR1 |
| SEQ ID No: 35 | VH 098, CDR2 |
| SEQ ID No: 36 | VH 098, CDR3 |
| SEQ ID No: 37 | VH 111 |
| SEQ ID No: 38 | VH 111, CDR1 |
| SEQ ID No: 39 | VH 111, CDR2 |
| SEQ ID No: 40 | VH 111, CDR3 |

TABLE 1B

VL-region

| | |
|---|---|
| SEQ ID No: 41 | VL 114 |
| SEQ ID No: 42 | VL 114, CDR1 |
| SEQ ID No: 43 | VL 114, CDR2 |
| SEQ ID No: 44 | VL 114, CDR3 |
| SEQ ID No: 45 | VL 011 |
| SEQ ID No: 46 | VL 011, CDR1 |
| SEQ ID No: 47 | VL 011, CDR2 |
| SEQ ID No: 48 | VL 011, CDR3 |
| SEQ ID No: 49 | VL 017-D12 |
| SEQ ID No: 50 | VL 017-D12, CDR1 |
| SEQ ID No: 51 | VL 017-D12, CDR2 |
| SEQ ID No: 52 | VL 017-D12, CDR3 |
| SEQ ID No: 53 | VL 042 |
| SEQ ID No: 54 | VL 042, CDR1 |
| SEQ ID No: 55 | VL 042, CDR2 |
| SEQ ID No: 56 | VL 042, CDR3 |
| SEQ ID No: 57 | VL 092-A09 |
| SEQ ID No: 58 | VL 092-A09, CDR1 |
| SEQ ID No: 59 | VL 092-A09, CDR2 |
| SEQ ID No: 60 | VL 092-A09, CDR3 |
| SEQ ID No: 61 | VL 101 |
| SEQ ID No: 62 | VL 101, CDR1 |
| SEQ ID No: 63 | VL 101, CDR2 |
| SEQ ID No: 64 | VL 101, CDR3 |
| SEQ ID No: 65 | VL 025 |
| SEQ ID No: 66 | VL 025, CDR1 |
| SEQ ID No: 67 | VL 025, CDR2 |
| SEQ ID No: 68 | VL 025, CDR3 |
| SEQ ID No: 69 | VL 109 |
| SEQ ID No: 70 | VL 109, CDR1 |
| SEQ ID No: 71 | VL 109, CDR2 |
| SEQ ID No: 72 | VL 109, CDR3 |
| SEQ ID No: 73 | VL 098 |
| SEQ ID No: 74 | VL 098, CDR1 |
| SEQ ID No: 75 | VL 098, CDR2 |
| SEQ ID No: 76 | VL 098, CDR3 |
| SEQ ID No: 77 | VL 111 |
| SEQ ID No: 78 | VL 111, CDR1 |
| SEQ ID No: 79 | VL 111, CDR2 |
| SEQ ID No: 80 | VL 111, CDR3 |

In a particularly preferred embodiment, the ADC is HuMax TF ADC (IgG1, vcMMAE), which is an ADC composed of a human monoclonal IgG1,κ antibody 011 against TF conjugated via a protease cleavable valine citrulline linker to the drug monomethyl auristatin E (vcMMAE). The identification and production of this antibody is described in WO 2011157741. Each monoclonal antibody (mAb) molecule carries an average of 4 drug molecules. The antibody portion has an approximate molecular weight of 147 kDa. On average, four molecules of vcMMAE (molecular weight 1.3 kDa) are attached to each mAb molecule yielding a total average molecular weight of HuMax TF ADC of 152 kDa. The isoelectric point of HuMax-TF-ADC is approximately 8.7.

Formulation

Therapeutic formulations of the antibodies used in accordance with the present invention are prepared for storage by mixing an ADC having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed.

Generally, the lyophilized and reconstituted formulations according to the invention comprise an anti-TF ADC, a buffering agent, a stabilizing agent (typically a non-reducing sugar or a sugar alcohol or an amino acid), and a bulking agent. Preferred stabilizing agents are sucrose, trehalose and combinations thereof. Preferred bulking agents are mannitol, glycine and combinations thereof.

The term "buffer" as used herein denotes a pharmaceutically acceptable buffer. Generally, the buffer has a pKa and buffering capacity suitable for the pH range of about 5 to about 7, preferably of about 5.5 to 6.5, such as about pH 6 or about pH 6.0. For lyophilized formulations, the buffer components should not crystallize at sub-ambient temperatures at the concentration used. Buffers having a higher collapse temperature are preferred, since it will enable a faster and more robust lyophilization cycle. Suitable pharmaceutically acceptable buffers include, but are not limited to, histidine-buffers, citrate-buffers, succinate-buffers, carbonic acid-buffers, phosphate buffers, glycolate-buffers, TRIS® (tris (hydroxymethyl) aminomethane) buffers and mixtures thereof. Preferred buffers are based on L-histidine, citrate, phosphate, carbonic acid, succinate and/or glycolate, such as histidine and/or citrate, and include also mixtures, e.g., of L-histidine with L-histidine hydrochloride or with TRIS® (tris (hydroxymethyl) aminomethane). Potentially, pH adjustment with an acid or a base known in the art may be needed. The above-mentioned L-histidine, citrate, phosphate, carbonic acid, succinate and/or glycolate buffers are generally used in an amount of about 1 mM to about 100 mM, such as from about 5 to about 80 mM, preferably of about 20 mM to about 50 mM, more preferably of about 10 to about 30 mM, and still more preferably of about 30 mM. The concentration of a phosphate buffer is preferably in the range of about 1 to about 30 mM. Independently from the buffer used, the pH can be adjusted at a value comprising about 5 to about 7 and preferably about 5.5 to about 6.5 and most preferably about 6.0 by adjustment with an acid or base known in the art or by using adequate mixtures of buffer components or both. Preferably, the buffer comprises a histidine and/or citrate buffer at a concentration of about 10 to about 30 mM, such as a histidine buffer at a concentration of about 30 mM.

The formulation of the invention can further comprise one or more pharmaceutically acceptable stabilizers as defined hereinabove and ingredients also known in the art as "lyoprotectants" such as sugars, sugar alcohols, amino sugars, amino acids and dextrans as known in the art. Typically, pharmaceutically acceptable stabilizer can be used in an amount of about 1 mM to about 500 mM. Suitable sugars comprise but are not limited to monosaccharides and disaccharides. Non-limiting examples of sugars and sugar alcohols for use according to the invention include trehalose, sucrose, mannitol, sorbitol, mannose, maltose, galactose, fructose, sorbose, raffinose, glucosamine, N-methylglucosamine (also referred to as "meglumine"), galactosamine and neuraminic acid and combinations thereof. Preferred are non-reducing sugars and sugar alcohols, such as sucrose or trehalose, at concentrations of about 10 to about 250 mM, such as about 50 to 225 mM, such as about 84 to 146, such as about 84 to 92 mM. Most preferred is sucrose.

In one embodiment the formulation comprises 84 to 92 mM sucrose, such as 85, 86, 87, 88, 89, 90, 91 or 92 mM sucrose. Most preferred the formulation comprises 88 mM sucrose.

Particularly, sugar alcohols such as mannitol may also be used as bulking agent to produce a homogeneous and stable lyophilization cake, which can be reconstituted within an acceptable time, more specifically within 0-600 seconds. In general, a "bulking agent" is used when the total amount of API is too small to provide adequate structure to the cake. Bulking agents should provide an inert matrix which gives a pharmaceutically elegant cake. The bulking agent also modifies the thermal characteristics of a formulation. The concentration of the active drug is often so low that the freeze-drying characteristics of the system are due solely to the bulking agent. Common bulking agents are including mannitol, glycine as crystalline bulking agents; sucrose, trehalose, gelatin, dextran as amorphous bulking agents. Preferred bulking agents are mannitol and glycine.

In one embodiment, the formulation comprises from about 158 to about 274 mM mannitol, such as 160 mM, or 162 mM, or 165 mM, or 170 mM, or 180 mM, or 200 mM mannitol. Most preferred it comprises about 165 mM mannitol, or 165 mM mannitol.

Certain lyophilized formulations according to the invention are designed so that it is possible to exclude surfactants. However, as a person skilled in the art can appreciate, for some purposes it may nonetheless be desirable to include a surfactant. Suitable pharmaceutically acceptable surfactants comprise but are not limited to polyethylen-sorbitan-fatty acid esters, polyethylene-polypropylene glycols, polyoxyethylene-stearates and sodium dodecyl sulphates. Polyethylen-sorbitan-fatty acid esters include polyethylen(20)-sorbitan-esters (synonym to polysorbate 20, sold under the trademark (™) Tween 20™ and polyoxyethylene(20)sorbitanmonooleate (synonym to polysorbate 80 sold under the trademark Tween 80(TM)). Polyethylene-polypropylene glycols are those sold under the names Pluronic® F68 or Poloxamer 188™. Polyoxyethylene-stearates are sold under the trademark Myrj™. Polyoxyethylene monolauryl ether are those sold under the trademark Brij™. When desirable, polyethylen-sorbitan-polyethylen(20)-sorbitan-esters (Tween 20™) and polyoxyethylene(20)sorbitanmonooleate (Tween 80™) can be used, e.g., in an amount of about 0.01% to about 0.06%, such as about 0.02% to about 0.04%.

Certain lyophilized formulations according to the invention are designed so that it is possible to exclude inorganic salts such as sodium chloride (NaCl), often used as isotonicity agent, from the pre-lyophilization liquid and lyophilized formulation. Other examples of salts include salts of any combinations of the cations sodium potassium, calcium or magnesium with anions chloride, phosphate, citrate, succinate, sulphate or mixtures thereof. However, as a person of skill in the art can appreciate, for some purposes it may nonetheless be desirable to include an inorganic salts, e.g., for reconstitution of the lyophilized formulation, i.e., as a diluent as described below.

The formulation of the invention can further comprise one or more of the following ingredients: antioxidants, ascorbic acid, glutathione, preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); cyclodextrin, e.g. hydroxypropyl- -cyclodextrin, sulfobutylethyl- -cyclodextrin, [beta]-cyclodextrin, polyethyleneglycol, e.g. PEG 3000, 3350, 4000, or 6000; low molecular weight (less than about 10 residues) polypeptides; proteins, such as serum albumin, gelatin, or immunoglobulins; chelating agents such as EDTA; salt-forming counterions such as sodium; and metal complexes (e.g. Zn-protein complexes).

Process

Freeze drying generally contains three main steps: freezing, primary drying, and secondary drying. The first stage is for the product to be frozen at a temperature lower than eutectic or glass transition temperature of the product. Rate of freezing affects size of water crystals and subsequent rate of drying. The second stage is primary drying, which removes the solvent (ice) water. It is important that product temperature remains below the collapse temperature and all ice/water is sublimed. The third stage is secondary drying which removes "bound" water or water from solute, during which the shelf temperature often raised higher than 40° C. to accelerate desorption process. Lyophilization methods suitable for antibody- and other protein or protein conjugate formulations are well-known by a person the skilled in the art and are described in, e.g. "Lyophilization of Biopharmaceuticals" by Henry R. Costantino and Michael J. Pikal; "Freeze Drying/Lyophilization of Pharmaceuticals and Biological Products" by Louis Rey and Joan C. May.

In one aspect of the invention, the lyophilization of the aqueous solution comprises the steps of:
a. cooling the aqueous solution at 0.3° C./min to 3° C./min to between −40° C. and −60;
b. holding isothermally for at least 120 min;
c. warming to between −20° C. and −15° C. at a rate of 0.3° C./min to 6° C./min;
d. holding isothermally for at least 180 min;
e. applying vacuum using a pressure between 30 mTorr and 300 mTorr at a temperature between −40° C. and −10° C.;
f. increasing the temperature to between 35° C. and 50° C. at between 0.3° C./min and 3° C./min and
g. holding isothermally for at least 10 hours or until the residual moisture is not more than 2%.

In another embodiment the lyophilization of the aqueous solution comprises the steps of:
a. cooling the aqueous solution at a rate of from 0.5° C./min to 1° C./min to −40° C. or less;
b. holding isothermally for at least 120 min;
c. warming to between −20° C. and −15° C. at a rate of from 0.5° C./min to 3° C./min;
d. holding isothermally for at least 180 min;
e. applying vacuum using a pressure between 50 mTorr and 200 mTorr at a temperature between −30° C. and −10° C.;
f. increasing the temperature to between 35° C. and 50° C. at a rate of from 0.5° C./min and 1° C./min and
g. holding isothermally for at least 10 hours.

In one embodiment the cooling step a) is performed by cooling the aqueous solution with at least 0.3° C./min such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0° C./min to a temperature of −40° C.

In another embodiment the cooling step a) is performed by cooling the aqueous solution with at least 0.3° C./min such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0° C./min to a temperature of −50° C.

In another embodiment the cooling step a) is performed by cooling the aqueous solution with at least 0.3° C./min such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0° C./min to a temperature of −60° C.

In another embodiment the warming step c) is performed by warming the material with at least 0.3° C./min such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 3.8, 3.9, 4.0, 4.5, 5.0 or 6.0° C./min to a temperature of −15° C.

In another embodiment the warming step c) is performed by warming the material with at least 0.3° C./min such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 3.8, 3.9, 4.0, 4.5, 5.0 or 6.0° C./min to a temperature of −20° C.

In another embodiment the temperature increase of step f) is performed with at least 0.3° C./min, such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0° C./min to a temperature of 35° C.

In another embodiment the temperature increase of step f) is performed with at least 0.3° C./min, such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0° C./min to a temperature of 40° C.

In another embodiment the temperature increase of step f) is performed with at least 0.3° C./min, such as 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0° C./min to a temperature of 50° C.

Use

In another aspect the invention provides the ADC formulation as defined in any of aspects or embodiments herein for use in the treatment of cancer. Exemplary cancers include, but are not limited to, those caused by tumors of the central nervous system, head and neck cancer, lung cancer, such as NSCLC, breast cancer, specifically triple-negative breast cancer, esophageal cancer, gastric or stomach cancer, liver and biliary cancer, pancreatic cancer, colorectal cancer, bladder cancer, kidney cancer, prostate cancer, endometrial cancer, ovarian cancer, malignant melanoma, sarcoma, tumors of unknown primary origin, bone marrow cancer, acute lymphoblastic leukemia, chronic lymphoblastic leukemia and non-Hodgkin lymphoma, skin cancer, glioma, cancer of the brain, uterus, acute myeloid leukemia and rectum. In one embodiment, the antibody part of the ADC is an anti-TF antibody and the formulation of the invention is administered to a subject suffering from pancreatic cancer, colorectal cancer, breast cancer, bladder cancer, prostate cancer or ovarian cancer.

Prior to administration to a subject, a lyophilized formulation of the invention comprising a therapeutically effective amount of ADC is dissolved, i.e., reconstituted, into a pharmaceutically acceptable diluent. Exemplary, non-limiting diluents include sterile pharmaceutical grade water (water for injection, WFI) or saline, bacteriostatic water for injection (BWFI), a pH buffered solution (e.g. phosphate-buffered saline), Ringer's solution and dextrose solution. For example, a lyophilized formulation of the invention can be reconstituted in water, pH buffered solution (e.g. phosphate-buffered saline), Ringer's solution and dextrose solution. For example, a lyophilized formulation of the invention can be reconstituted in sterile water for injection (WFI) to a concentration of about 5 to about 30 mg/mL ADC, such as about 7 to about 20 mg/mL ADC, such as about 8 to 15 mg/mL ADC, such as about 9 to about 11 mg/mL ADC, such as about 10 mg/mL ADC. The concentrate may optionally be further diluted for, e.g., infusion into a pH buffered solution (e.g. phosphate-buffered saline, Ringer's solution and/or dextrose solution) to a concentration of about 0.05 mg/mL to 30 mg/mL ADC, such as, e.g., 0.12 mg/mL to 2.40 mg/mL ADC.

Typically, the reconstituted formulation of the present invention is suitable for parenteral administration. The phrases "parenteral administration" and "administered parentally" as used herein means modes of administration other than enteral and topical administration, usually by injection or infusion, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In one embodiment the pharmaceutical composition is administered by intravenous or subcutaneous injection or infusion, e.g., by reconstituting the lyophilized formulation in sterile water or saline and held in IV bags or syringes before administration to a subject.

The invention also provides for a kit comprising the lyophilized formulation of an anti-TF ADC according to the invention, typically in a hermetically sealed container such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

Embodiments of the Invention

1. A lyophilized formulation of an anti-tissue factor (TF) antibody-drug conjugate (ADC), the lyophilized formulation obtainable or obtained by lyophilizing an aqueous formulation comprising about 5 g/L to about 30 g/L anti-TF ADC and pharmaceutically acceptable excipients comprising;
   a. about 20 to about 50 mM histidine or citrate buffer having a pH of about 5 to about 7;
   b. about 10 to about 250 mM sucrose or trehalose; and
   c. about 50 mM to about 300 mM mannitol or glycine.

2. A lyophilized formulation of an anti-TF ADC, the lyophilized formulation obtainable or obtained by lyophilizing an aqueous formulation comprising
   a. an anti-TF ADC comprising a therapeutic moiety which is selected from MMAE and MMAF and an anti-TF antibody comprising VH and VL regions selected from the group consisting of: a VH region comprising an amino acid sequence of SEQ ID NO: 5 and a VL region comprising an amino acid sequence of SEQ ID NO: 45; a VH region comprising an amino acid sequence of SEQ ID NO: 33 and a VL region comprising an amino acid sequence of SEQ ID NO: 73; a VH region comprising an amino acid sequence of SEQ ID NO: 37 and a VL region comprising an amino acid sequence of SEQ ID NO: 77; or a VH region comprising an amino acid sequence of SEQ ID NO: 1 and a VL region comprising an amino acid sequence of SEQ ID NO: 41; and b. pharmaceutically acceptable excipients comprising: a buffer which limits pH shifts during the lyophilizing step, at least one non-reducing sugar which forms an amorphous phase with the anti-TF ADC in solid state and at least one bulking agent,
wherein the lyophilized formulation is essentially free of any surfactant.

3. The lyophilized formulation of embodiment 2, wherein the aqueous formulation comprises a buffer selected from the group consisting of histidine, citrate, phosphate, carbonic acid, succinate, glycolate and a combination of any thereof.

4. The lyophilized formulation of any of embodiments 1 or 3, wherein the buffer is histidine.

5. The lyophilized formulation of any one of the preceding embodiments, wherein the aqueous formulation comprises from about 7 to about 20 g/L anti-TF ADC, such as from about 8 to about 15 g/L anti-TF ADC.

6. The lyophilized formulation of any one of the preceding embodiments, wherein the aqueous formulation comprises from about 9 to about 11 g/L anti-TF ADC.

7. The lyophilized formulation of any one of the preceding embodiments, wherein the pH of the aqueous formulation is in a range from about 5.5 and 6.5, such as about 6.

8. The lyophilized formulation of any one of the preceding embodiments, wherein the aqueous formulation comprises from about 25 to about 40 mM histidine, such as from about 28 to about 34 mM histidine.

9. The lyophilized formulation of any one of the preceding embodiments, wherein the aqueous formulation comprises from about 29 to about 31 mM histidine.

10. The lyophilized formulation of any one of the preceding embodiments, wherein the aqueous formulation comprises from about 50 to about 225 mM sucrose or trehalose, such as 84 to about 165 mM sucrose or trehalose.

11. The lyophilized formulation of any one of the preceding embodiments, wherein the aqueous formulation comprises from about 84 to about 146 mM sucrose, such as from about 84 to about 92 mM sucrose.

12. The lyophilized formulation of any one of the preceding embodiments, wherein the aqueous formulation comprises from about 100 to about 274 mM mannitol or glycine.

13. The lyophilized formulation of any one of the preceding embodiments, wherein the aqueous formulation comprises from about 158 to about 172 mM mannitol.

14. The lyophilized formulation of any one of the preceding embodiments, wherein the aqueous formulation comprises from about 9 to about 11 g/L anti-TF ADC, such as about 10 mg/mL anti-TF ADC, and about 30 mM histidine, about 88 mM sucrose and about 165 mM mannitol.

15. A lyophilized formulation comprising
a. an anti-TF antibody drug conjugate,
b. a buffering agent selected from histidine, citrate, succinate, glycolate, carbonic acid and phosphate;
c. a non-reducing sugar selected from sucrose, trehalose and a combination thereof, and
d. a bulking agent selected from mannitol and glycine.

16. The lyophilized formulation of any one of the preceding embodiments, which is essentially free of any polysorbate.

17. The lyophilized formulation of any one of the preceding embodiments, which is essentially free of any surfactant.

18. The lyophilized formulation of any one of the preceding embodiments, which is free of any surfactant.

19. A lyophilized formulation consisting essentially of
a. an anti-TF antibody drug conjugate,
b. a buffering agent selected from histidine and citrate;
c. a non-reducing sugar selected from sucrose, trehalose and a combination thereof, and
d. a bulking agent selected from mannitol and glycine.

20. The lyophilized formulation of any one of the preceding embodiments, comprising mannitol and sucrose, wherein the weight ratio of mannitol to sucrose is at least about 1.

21. The lyophilized formulation of any one of the preceding embodiments, comprising mannitol and sucrose, wherein the weight ratio of mannitol to sucrose is between about 1 and about 30, such as between 1 and about 10, such as between about 1 and about 2.

22. The lyophilized formulation of any one of the preceding embodiments, comprising mannitol and sucrose, wherein the weight ratio of mannitol to sucrose is about 1.

23. The lyophilized formulation of any one of the preceding embodiments, comprising mannitol, wherein the weight ratio of mannitol to anti-TF ADC is at least about 3.

24. The lyophilized formulation of any one of the preceding embodiments, comprising mannitol and sucrose, wherein the weight ratio of mannitol to anti-TF ADC is about 3 and the weight ratio of mannitol to sucrose is about 1.

25. The lyophilized formulation of any one of the preceding embodiments, obtainable or obtained by lyophilizing an aqueous formulation comprising less than about 250 mM sucrose and less than about 300 mM mannitol.

26. The lyophilized formulation of any one of the preceding embodiments, obtainable or obtained by lyophilizing an aqueous formulation comprising less than about 160 mM sucrose and less than about 274 mM mannitol.

27. The lyophilized formulation of any one of the preceding embodiments, obtainable or obtained by lyophilizing an aqueous formulation comprising from about 7 to about 20 g/L anti-TF ADC and
a. about 28 to 34 mM histidine;
b. about 84 to about 146 mM sucrose;
c. about 158 to about 274 mannitol; or
d. a combination of any two or all of (a) to (c).

28. The lyophilized formulation of any one of the preceding embodiments, obtainable or obtained by lyophilizing an aqueous formulation comprising from about 9 to about 11 g/L anti-TF ADC, such as about 10 mg/mL anti-TF ADC, and
a. about 30 mM histidine;
b. about 88 mM sucrose;
c. about 165 mM mannitol; or
d. a combination of any two or all of (a) to (c).

29. The lyophilized formulation of any one of the preceding embodiments, wherein the average absolute number of drug moieties per antibody molecule is 1, 2, 3, 4, 5, 6, 7, or 8, such as 3, 4 or 5.

30. The lyophilized formulation of any one of the preceding embodiments, wherein the antibody is conjugated to a hydrophobic drug.

31. The lyophilized formulation of any one of the preceding embodiments, wherein the drug is an auristatin or a functional peptide analogue or derivate thereof.

32. The lyophilized formulation of any one of the preceding embodiments, wherein the drug is linked to the anti-TF antibody via a linker attached to sulphydryl residues of the anti-TF antibody, the sulphydryl residues obtained by partial reduction, or reduction of the anti-TF antibody.

33. The lyophilized formulation of any of the above embodiments, wherein the drug is MMAE or MMAF.

34. The lyophilized formulation of any of the above embodiments, wherein the drug is linked to the anti-TF antibody via a linker-drug which is selected from: vcMMAE, vcMMAF or mcMMAF.

35. The lyophilized formulation of any one of the preceding embodiments, wherein the antibody is a full-length antibody.

36. The lyophilized formulation of any one of the preceding embodiments, wherein the antibody is a human IgG1κ antibody.

37. The lyophilized formulation of any one of the preceding embodiments, wherein the antibody competes for binding to human TF with one or more reference antibodies comprising VH and VL regions selected from the groups consisting of:
   a. a VH region comprising an amino acid sequence of SEQ ID NO: 5 and a VL region comprising an amino acid sequence of SEQ ID NO: 45;
   b. a VH region comprising an amino acid sequence of SEQ ID NO: 33 and a VL region comprising an amino acid sequence of SEQ ID NO: 73;
   c. a VH region comprising an amino acid sequence of SEQ ID NO: 37 and a VL region comprising an amino acid sequence of SEQ ID NO: 77; or
   d. a VH region comprising an amino acid sequence of SEQ ID NO: 1 and a VL region comprising an amino acid sequence of SEQ ID NO: 41.

38. The lyophilized formulation of any one of the preceding embodiments, wherein the anti-TF antibody comprises
   a. a variable heavy (VH) region comprising a CDR1 region having the amino acid sequence set forth in SEQ ID NO: 6, a CDR2 region having the amino acid sequence set forth in SEQ ID NO: 7, and a CDR3 region having the amino acid sequence set forth in SEQ ID NO: 8, and a variable light (VL) region comprising a CDR1 region having the amino acid sequence set forth in SEQ ID NO:46, a CDR2 region having the amino acid sequence set forth in SEQ ID NO: 47, and a CDR3 region having the amino acid sequence set forth in SEQ ID NO: 48;
   b. a VH region comprising a CDR1 region having the amino acid sequence set forth in SEQ ID NO: 34, a CDR2 region having the amino acid sequence set forth in SEQ ID NO: 35, and a CDR3 region having the amino acid sequence set forth in SEQ ID NO: 36, and a VL region comprising a CDR1 region having the amino acid sequence set forth in SEQ ID NO: 74, a CDR2 region having the amino acid sequence set forth in SEQ ID NO: 75, and a CDR3 region having the amino acid sequence set forth in SEQ ID NO: 76, or
   c. a VH region comprising a CDR1 region having the amino acid sequence set forth in SEQ ID NO: 38, a CDR2 region having the amino acid sequence set forth in SEQ ID NO: 39, and a CDR3 region having the amino acid sequence set forth in SEQ ID NO: 40, and a VL region comprising a CDR1 region having the amino acid sequence set forth in SEQ ID NO: 78, a CDR2 region having the amino acid sequence set forth in SEQ ID NO: 79 and a CDR3 region having the amino acid sequence set forth in SEQ ID NO: 80, or
   d. a VH region comprising a CDR1 region having the amino acid sequence set forth in SEQ ID NO: 2; a CDR2 region having the amino acid sequence set forth in SEQ ID NO: 3, and a CDR3 region having the amino acid sequence set forth in SEQ ID NO: 4, and a VL region comprising a CDR1 region having the amino acid sequence set forth in SEQ ID NO: 42, a CDR2 region having the amino acid sequence set forth in SEQ ID NO: 43, and a CDR3 region having the amino acid sequence set forth in SEQ ID NO: 44, or
   e. a variant of any of said antibodies, wherein said variant preferably has at most 1, 2 or 3 amino-acid modifications, more preferably amino-acid substitutions, such as conservative amino-acid substitutions in said sequences.

39. The lyophilized formulation of any one of the preceding embodiments, wherein the antibody comprises
   a. a VH region comprising an amino acid sequence of SEQ ID NO: 5 and a VL region comprising an amino acid sequence of SEQ ID NO: 45;
   b. a VH region comprising an amino acid sequence of SEQ ID NO: 33 and a VL region comprising an amino acid sequence of SEQ ID NO: 73;
   c. a VH region comprising an amino acid sequence of SEQ ID NO: 37 and a VL region comprising an amino acid sequence of SEQ ID NO: 77; or
   d. a VH region comprising an amino acid sequence of SEQ ID NO: 1 and a VL region comprising an amino acid sequence of SEQ ID NO: 41.

40. The lyophilized formulation of any one of the preceding embodiments, wherein the antibody is a full length fully human monoclonal IgG1 antibody, optionally IgG1κ.

41. An aqueous solution suitable for preparing a lyophilized formulation of an anti-TF ADC, comprising
   a. from about 7 to about 20 g/L anti-TF ADC, optionally wherein the antibody portion comprises the VH and VL sequences of any one of embodiments 37 to 39.
   b. about 28 to 34 mM histidine;
   c. about 84 to about 146 mM sucrose;
   d. about 158 to about 274 mannitol; or
   e. a combination of any two or all of (b) to (d).

42. A pharmaceutically acceptable liquid formulation obtained by reconstituting the lyophilized formulation of any one of embodiments 1-40 in a sterile aqueous diluent.

43. The liquid formulation of embodiment 42, comprising about 5 g/L to about 30 g/L anti-TF ADC, about 20 to about 50 mM histidine having a pH of about 5 to about 7; about 10 to about 250 mM sucrose or trehalose; and about 50 mM to about 300 mM mannitol or glycine.

44. The liquid formulation of embodiment 43, comprising about 9 to about 11 mg/mL anti-TF ADC, about 28 to about 34 mM histidine, about 84 to about 92 mM sucrose and about 158 to about 274 mM mannitol.

45. A method of preparing an injectable solution of an anti-TF ADC, comprising the step of reconstituting the lyophilized formulation of any one of embodiments 1 to 40 in a sterile aqueous diluent.

46. A lyophilized formulation of an anti-TF ADC, the lyophilized formulation prepared by lyophilizing an aqueous formulation comprising about 9 g/L to about 11 g/L anti-TF ADC and pharmaceutically acceptable excipients comprising: about 30 mM histidine buffer having a pH of about 5 to about 7; about 88 mM sucrose; and about 165 mM mannitol; wherein the antibody comprises a VH region comprising an amino acid sequence of SEQ ID NO: 5 and a VL region comprising an amino acid sequence of SEQ ID NO: 45; a VH region comprising an amino acid sequence of SEQ ID NO: 33 and a VL region comprising an amino acid sequence of SEQ ID NO: 73; a VH region comprising an amino acid sequence of SEQ ID NO: 37 and a VL region comprising an amino acid sequence of SEQ ID NO: 77; or a VH region comprising an amino acid sequence of SEQ ID NO: 1 and a VL region comprising an amino acid sequence of SEQ ID NO: 41, and wherein the linker-drug is vcMMAE, vcMMAF or mcMMAF.

EXAMPLE 1

This example shows the effect of certain buffers and pH values on the thermal stability of Anti-TF HuMab 098 (see WO2011157741 A2), herein referred to as HuMax-TF. An accelerated stability study for selected excipients, buffers and pH conditions was designed using the histidine and acetate buffer systems at pH 4.5-6.5.

The DOE (Design of Experiments) used was a response surface, linear design with one numerical (pH) and two categorical factors (buffer and excipient types). The DOE included duplicate samples for each formulation composition to assess the experimental variability associated with the various biophysical and analytical methods. Additional off-DOE samples at 50 mg/mL in the center point formulations and at 20 mg/mL with combined sorbitol and sodium chloride excipients were included in the study. Table 2 shows the preformulation design of experiment (DOE) samples for HuMax-TF.

TABLE 2

|   | pH | Buffer | Excipient | Protein Conc (mg/ml) |
|---|---|---|---|---|
| A | 4.5 | 30 mM Acetate | 140 mM NaCl | 20 |
| B | 4.5 | 30 mM Acetate | 140 mM NaCl | 20 |
| C | 5.0 | 30 mM Acetate | 140 mM NaCl | 20 |
| D | 6.0 | 30 mM Histidine | 140 mM NaCl | 20 |
| E | 6.5 | 30 mM Histidine | 140 mM NaCl | 20 |
| F | 5.5 | 30 mM Histidine | 140 mM NaCl | 20 |
| G | 5.5 | 30 mM Acetate | 140 mM NaCl | 20 |
| H | 4.5 | 30 mM Acetate | 225 mM sorbitol | 20 |
| I | 5.5 | 30 mM Histidine | 225 mM sorbitol | 20 |
| J | 5.5 | 30 mM Acetate | 140 mM NaCl | 20 |
| K | 6.0 | 30 mM Histidine | 225 mM sorbitol | 20 |
| L | 6.5 | 30 mM Histidine | 140 mM NaCl | 20 |
| M | 6.0 | 30 mM Histidine | 140 mM NaCl | 20 |
| N | 6.5 | 30 mM Histidine | 225 mM sorbitol | 20 |
| O | 5.0 | 30 mM Acetate | 225 mM sorbitol | 20 |
| P | 5.5 | 30 mM Acetate | 225 mM sorbitol | 20 |
| Q | 5.5 | 30 mM Histidine | 225 mM sorbitol | 20 |
| R | 5.0 | 30 mM Acetate | 140 mM NaCl | 20 |
| S | 5.5 | 30 mM Acetate | 225 mM sorbitol | 20 |
| T | 6.5 | 30 mM Histidine | 225 mM sorbitol | 20 |
| U | 5.0 | 30 mM Acetate | 225 mM sorbitol | 20 |
| V | 4.5 | 30 mM Acetate | 225 mM sorbitol | 20 |
| W | 5.5 | 30 mM Histidine | 140 mM NaCl | 20 |
| X | 6.0 | 30 mM Histidine | 225 mM sorbitol | 20 |
| Off-DOE Compositions for Higher Protein Concentration | | | | |
| Y | 5.0 | 30 mM Acetate | 225 mM sorbitol | 50 |
| Z | 5.0 | 30 mM Acetate | 140 mM NaCl | 50 |
| AA | 6.0 | 30 mM Histidine | 225 mM sorbitol | 50 |
| BB | 6.0 | 30 mM Histidine | 140 mM NaCl | 50 |
| Off-DOE Compositions for Excipient Mixtures | | | | |
| CC | 5.0 | 30 mM Acetate | 110 mM sorbitol + 70 mM NaCl | 20 |
| DD | 6.0 | 30 mM Histidine | 110 mM sorbitol + 70 mM NaCl | 20 |

The accelerated stability samples were tested by a variety of analytical methods. Selected results are discussed in Examples 2, 3 and 4.

EXAMPLE 2

Figure 1A:
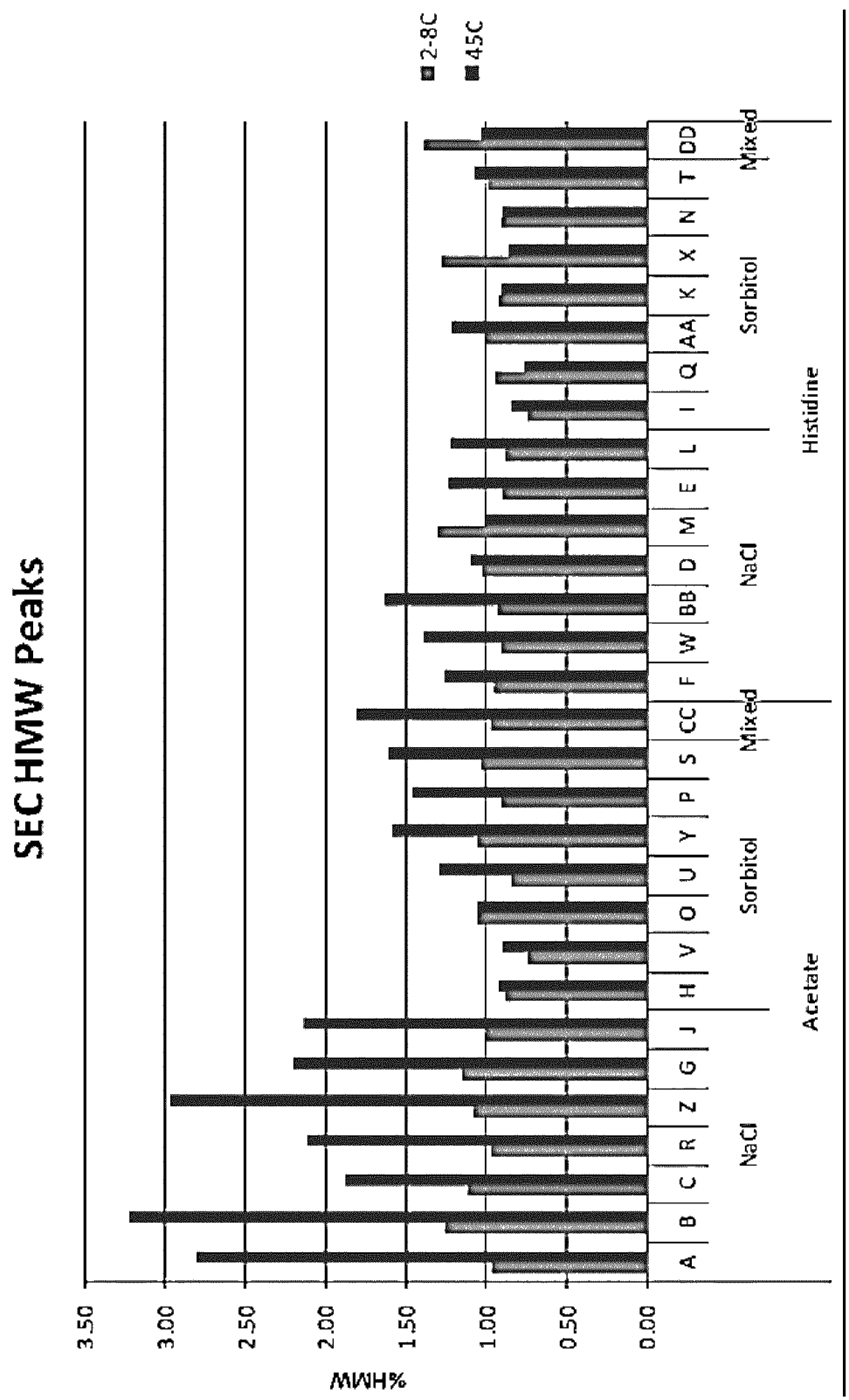
Figure 1B:
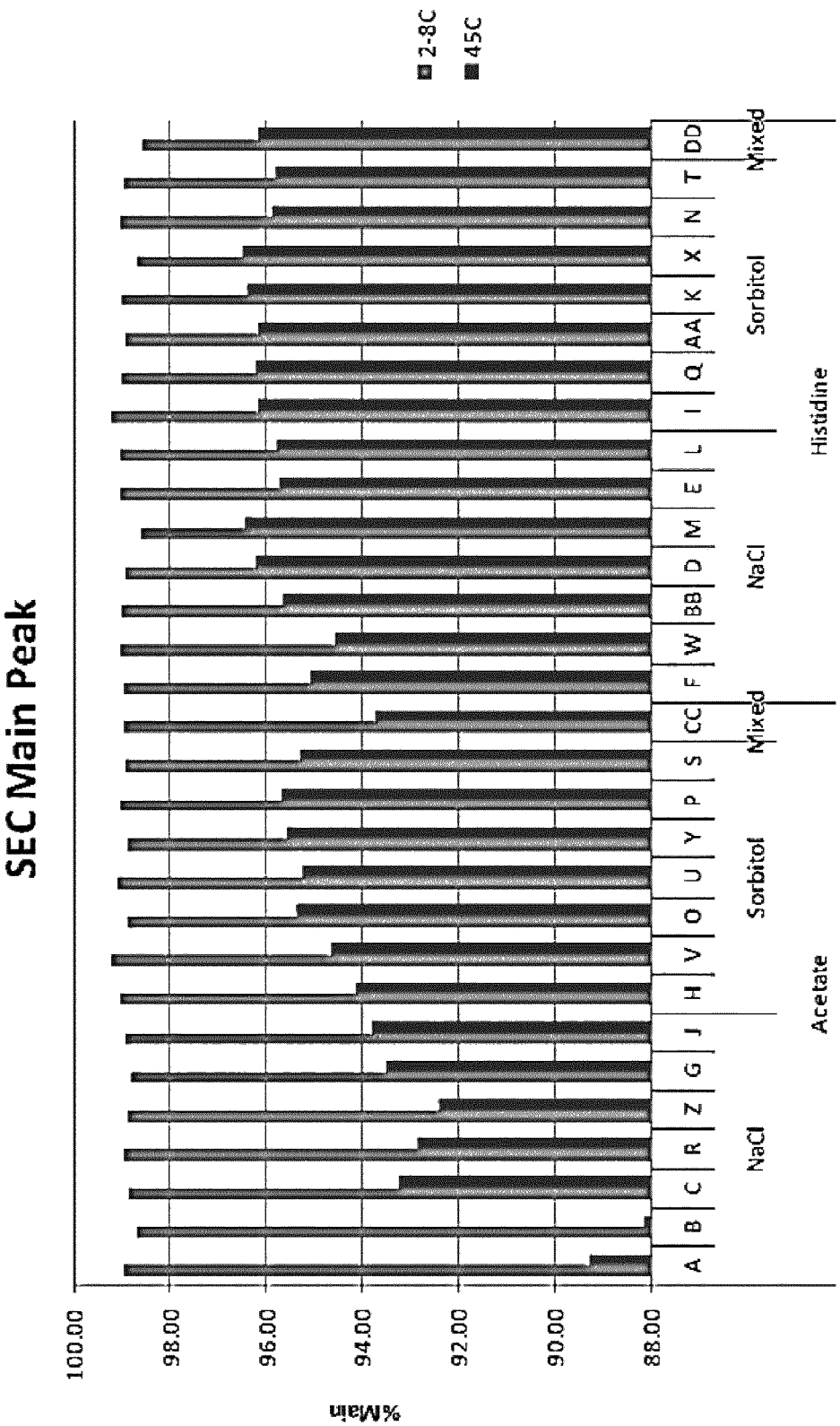
Figure 1C:
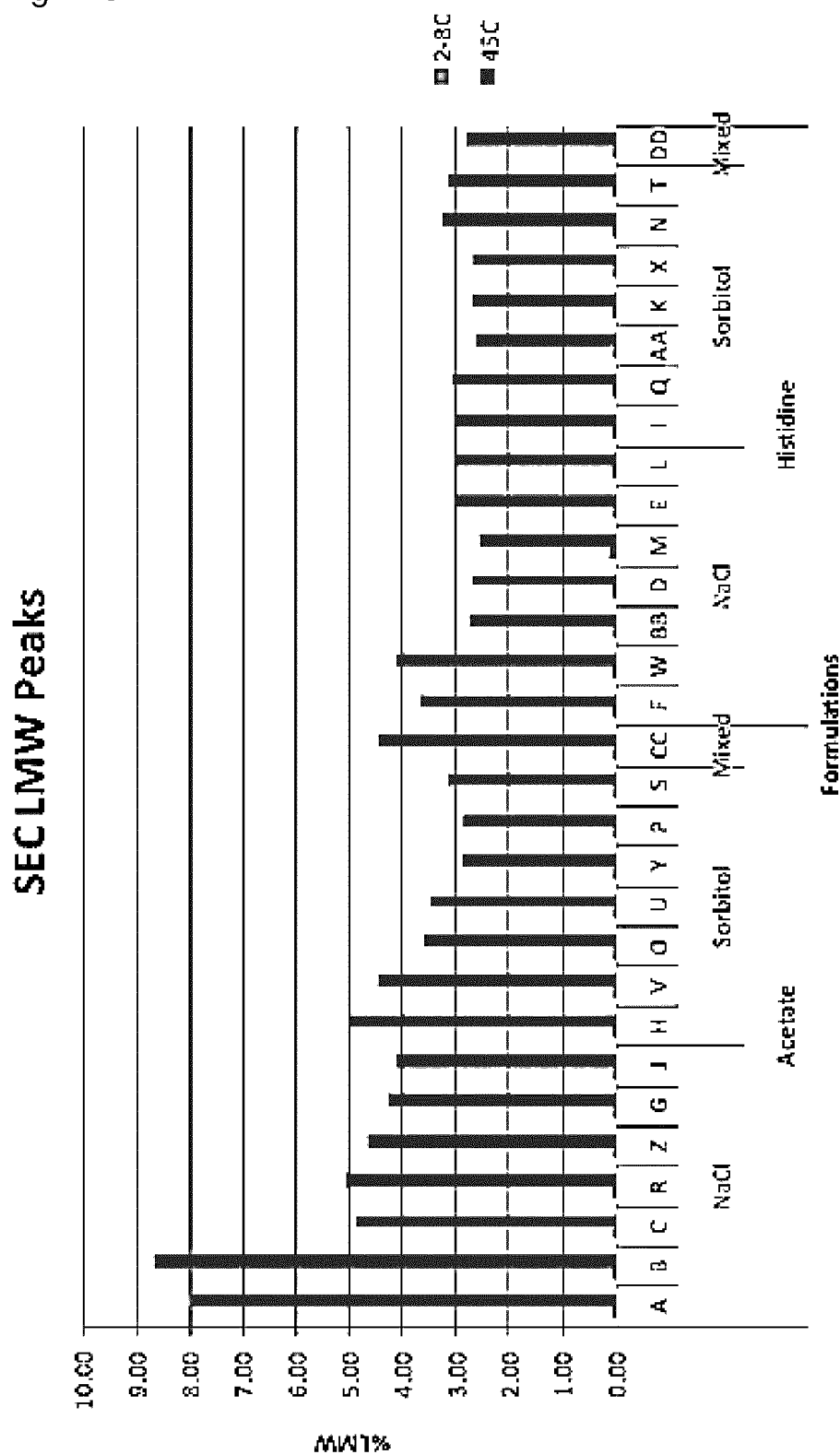

The HuMax-TF samples incubated at 5 and 45° C. (non-stressed and stressed, respectively) for four weeks were analyzed using SEC (size exclusion chromatography) to determine the effect of various formulations on the extent of aggregation and degradation. The SEC chromatograms of non-stressed HuMax-TF samples showed one major peak that corresponded to the monomeric antibody, and accounted for more than 98% of the total peak area. This one major SEC peak reflected the antibody's size homogeneity in each formulation. For the comparison of SEC data between various formulations, the peak area values for species that eluted before the main peak were combined and reported as percent HMW. Similarly, the peak area values for species that eluted after the main peak were combined and reported as percent degraded. The bar graphs presented in FIG. 1 showed no significant trends for any of the species for any of the formulations under the non-stressed conditions. For the stressed conditions, however, increased % HMW and % LMW and decreased % Main values due to aggregation and degradation were observed. Higher % HMW and % LMW values were observed for the acetate formulations relative to the histidine formulations. For both buffer types, and more notably in acetate formulations, the % HMW and % LMW species decreased in with increasing pH and with sorbitol relative to sodium chloride.

EXAMPLE 3

SDS-PAGE analysis was performed under both reducing and non-reducing conditions for selected four-week DOE samples. Under reducing conditions, the heavy chain band appeared at approximately 54 kDa, and the light chain band appeared at approximately 26 kDa. Under non-reducing conditions, the main HuMax-TF band migrated at approximately 145 kDa. Samples were analyzed using reduced and non-reduced SDS-PAGE. Compared to the non-stressed samples, the heat stressed formulations showed an increase in the intensity of LMW bands below the intact IgG in the non-reduced gel. Similarly, increased intensities of new bands were observed between the heavy and light chain bands for the stressed samples relative to the non-stressed samples. For both the reduced and non-reduced samples, the acetate formulations showed a larger increase in intensity of these degraded species relative to the histidine formulations.

EXAMPLE 4

Figure 2A:
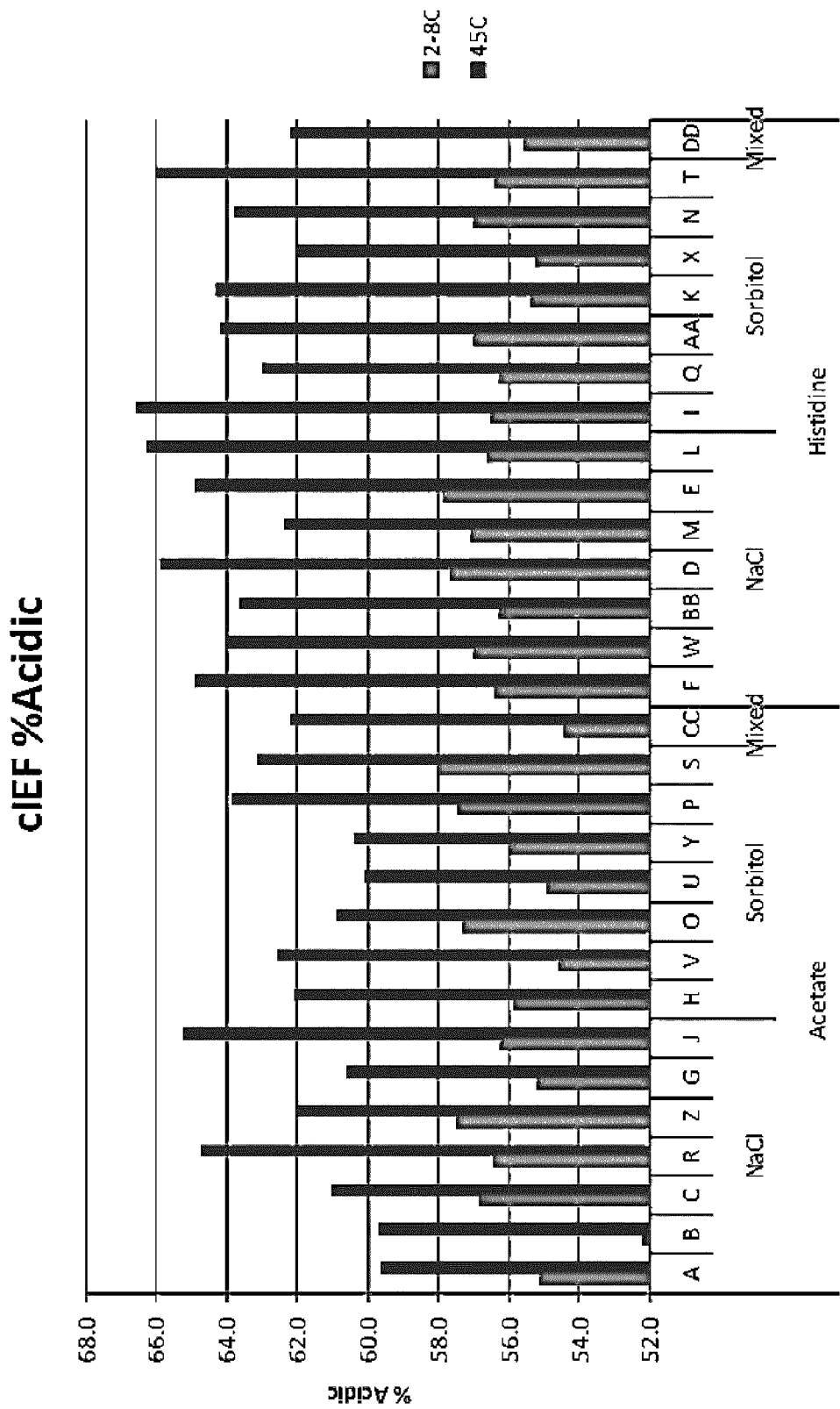
Figure 2B:
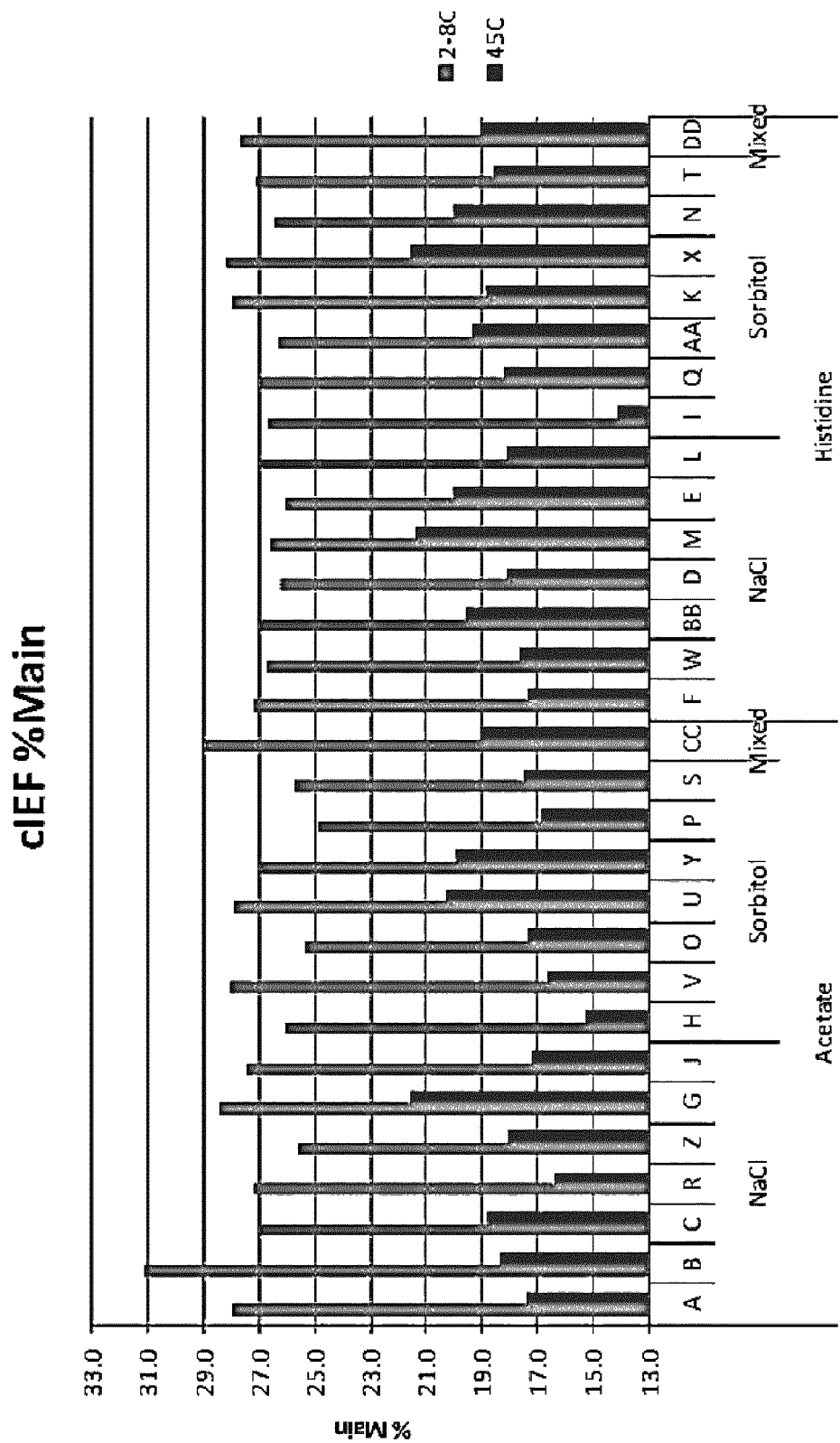
Figure 2C:
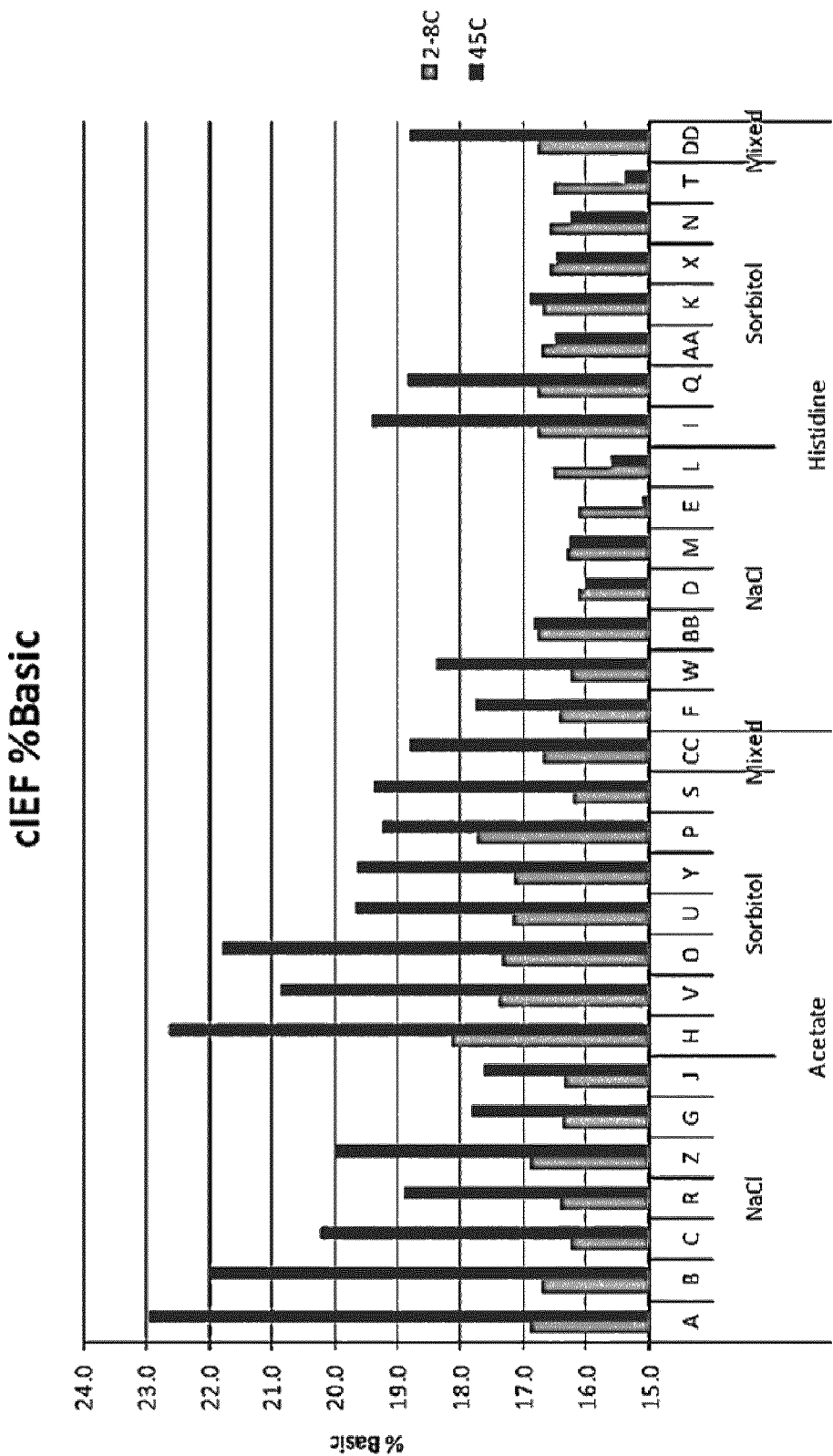

The one-week stressed and non-stressed HuMax-TF DOE samples were analyzed using cI EF (Imaged Capillary Isoelectric Focusing) to evaluate the effects of various formulation components on the observed peak areas. The results are shown in FIG. 2. The percent peak area values for the species with pI values lower than that of the main peak were combined and reported as percent acidic, and the percent peak area values for the species with pI values higher than that of the main peak were combined and reported as percent basic.

The cI EF analysis of non-stressed HuMax-TF DOE samples presented in FIG. 2 did not show any obvious trends for the dependence of cI EF results on pH, buffer type or excipient type for the non-stressed samples. The cI EF analysis of stressed DOE samples showed 5-13% decrease in the main peak percent area. The decrease in main peak area occurred concomitantly with an increase in the peak area for acidic species and, for most formulations, an increase in the percent basic peak area as well. The changes in percent acidic species depicted in the bar graphs did not show obvious pH dependency, but the acetate formulations generally showed slightly lower percent acidic peak areas than the histidine formulations. However, the percent basic species showed strong pH dependence with percent basic peak areas decreasing with increasing pH. Additionally, histidine formulations showed lower percent basic species than the acetate formulations.

EXAMPLE 5

A screening study was designed to test the effect of pH, presence of polysorbate, and presence of sorbitol on the stability of HuMax-TF-ADC in solution. HuMax-TF-ADC is an antibody-drug conjugate composed of the human monoclonal IgG1 antibody HuMax-TF 011 chemically conjugated via a protease cleavable valine citrulline (vc) linker to the microtubule-disrupting agent monomethyl auristatin E (MMAE).

Twelve different formulations were prepared using 3 different pH values. The solution formulation study design is shown in Table 3. All formulations contained HuMax-TF-ADC at 10 mg/mL with 30 mM Histidine. Tween=polysorbate 80 (PS80).

TABLE 3

| Formulation | pH | Tween Concentration (%) | Sorbitol (mM) |
|---|---|---|---|
| 1 | 5.5 | 0 | 0 |
| 2 | 5.5 | 0 | 225 |
| 3 | 5.5 | 0.02 | 0 |
| 4 | 5.5 | 0.02 | 225 |
| 5 | 6.0 | 0 | 0 |
| 6 | 6.0 | 0 | 225 |
| 7 | 6.0 | 0.02 | 0 |
| 8 | 6.0 | 0.02 | 225 |
| 9 | 6.5 | 0 | 0 |
| 10 | 6.5 | 0 | 225 |
| 11 | 6.5 | 0.02 | 0 |
| 12 | 6.5 | 0.02 | 225 |

The 12 formulations prepared for the screening study were analyzed using UV/Vis (UltraViolet-Visible Spectroscopy), icI EF, SEC, and DAR-HIC (Drug-to-Antibody Molar Ratio using Hydrophobic Interaction Chromatography). Formulation screening studies had shown that the main stability indicating parameters for HuMax-TF-ADC were aggregates measured by SEC and acidic isoforms (presumably due to deamidation) measured by icI EF.

Figure 3:
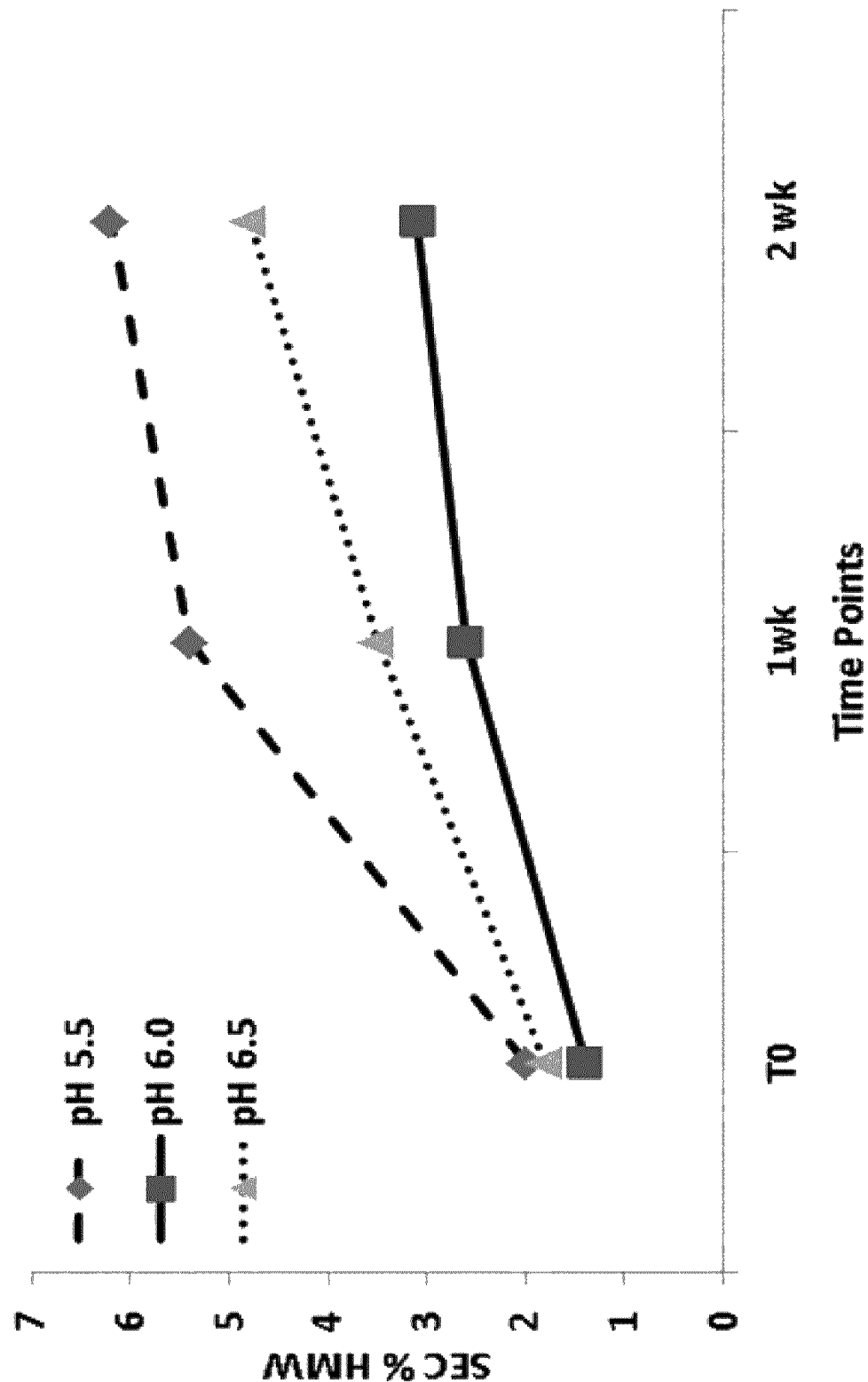
FIG. 3 shows the effect of pH on the percent HMW for HuMax TF ADC as determined by SEC when stored at 40° C. for 2 weeks. See Example 5 for details.

The effect of pH on the percentage of HMW formation in solution samples stored at 40° C. for 2 weeks was measured by SEC (FIG. 3 shows SEC % HMW for formulations 1, 5, and 9 in table 3). A pH of 6.0 was shown to be the most efficient on limiting aggregation of HuMax-TF-ADC in the histidine buffer.

Figure 4:
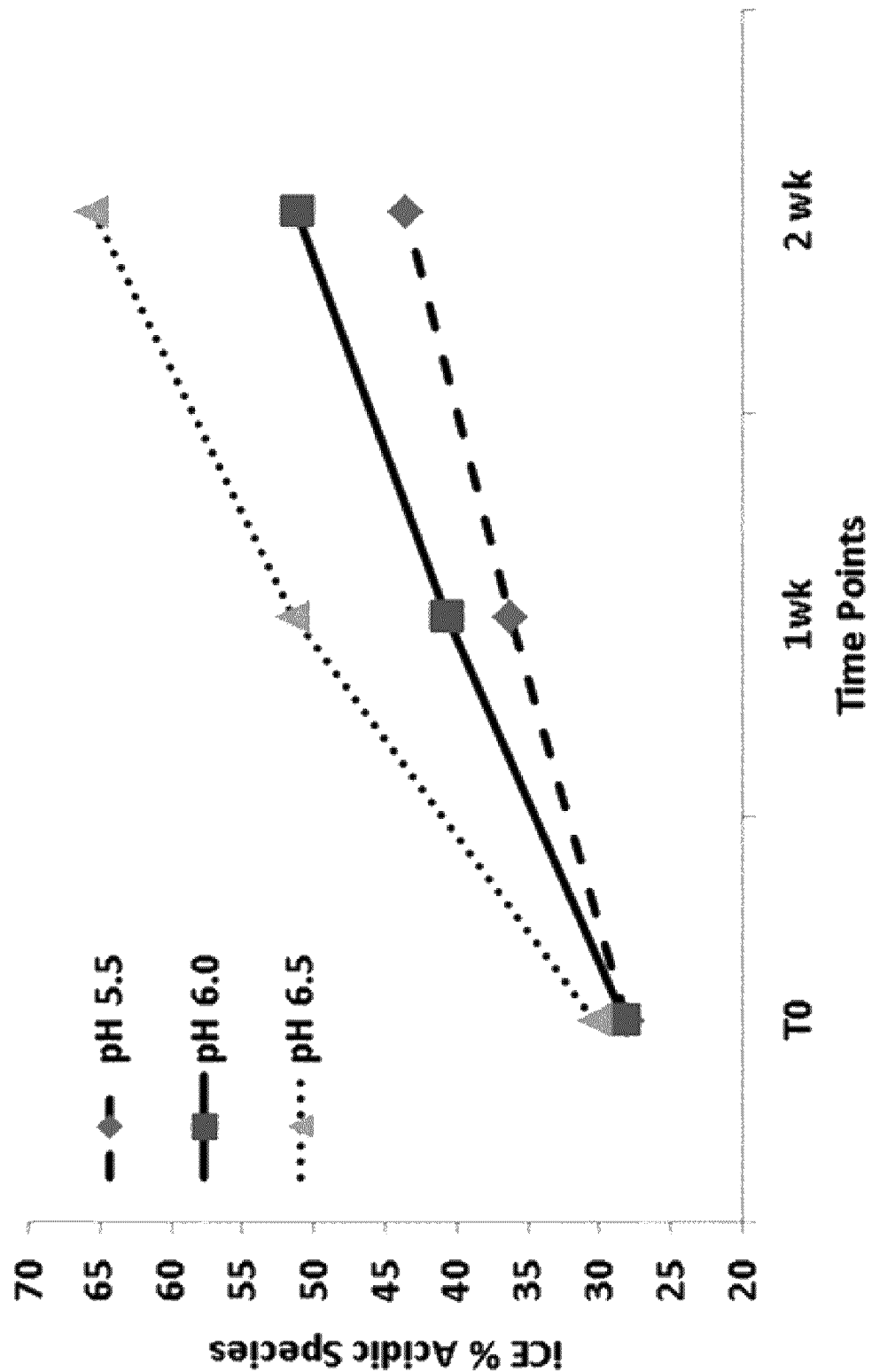
FIG. 4 shows the effect of pH on the percent acidic species as determined by iCE for HuMax TF ADC solutions stored at 40° C. for 2 weeks. See Example 5 for details.

The effect of pH on deamidation of HuMax-TF-ADC in solution samples stored at 40° C. for 2 weeks was measured by acidic species increase in icI EF (FIG. 4 shows results for formulations 1, 5, and 9 in table 3). A pH of 5.5 was found to be most efficient to limit deamidation, followed by pH 6.0 and pH 6.5.

Figure 5A:
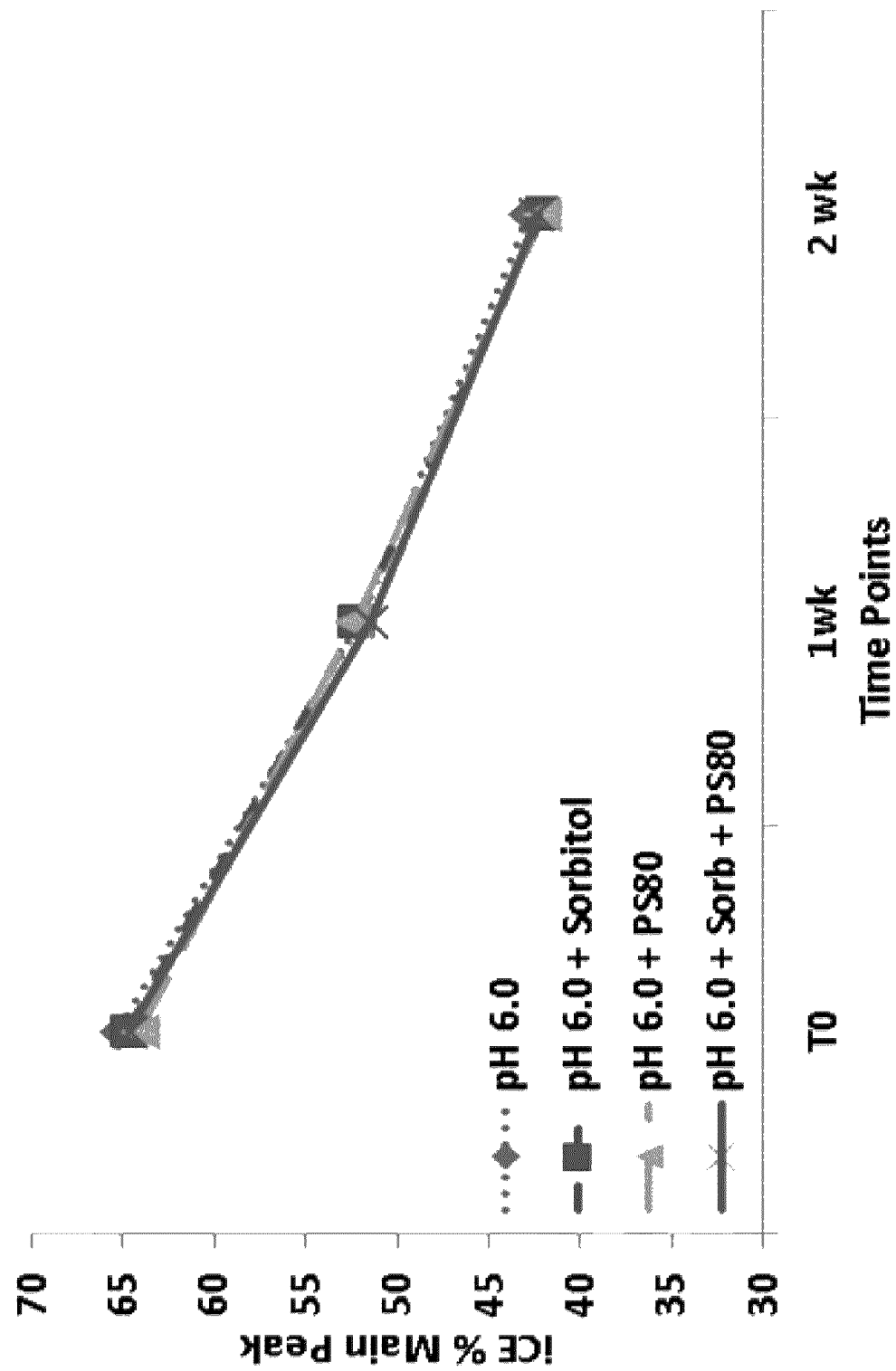
FIG. 5A shows the effect of sorbitol and PS80 (polysorbate 80) on percent charge main peak (by iCE) of HuMax TF ADC solutions prepared at pH 6.0 and stored at 40° C. for 2 weeks. See Example 5 for details.
Figure 5B:
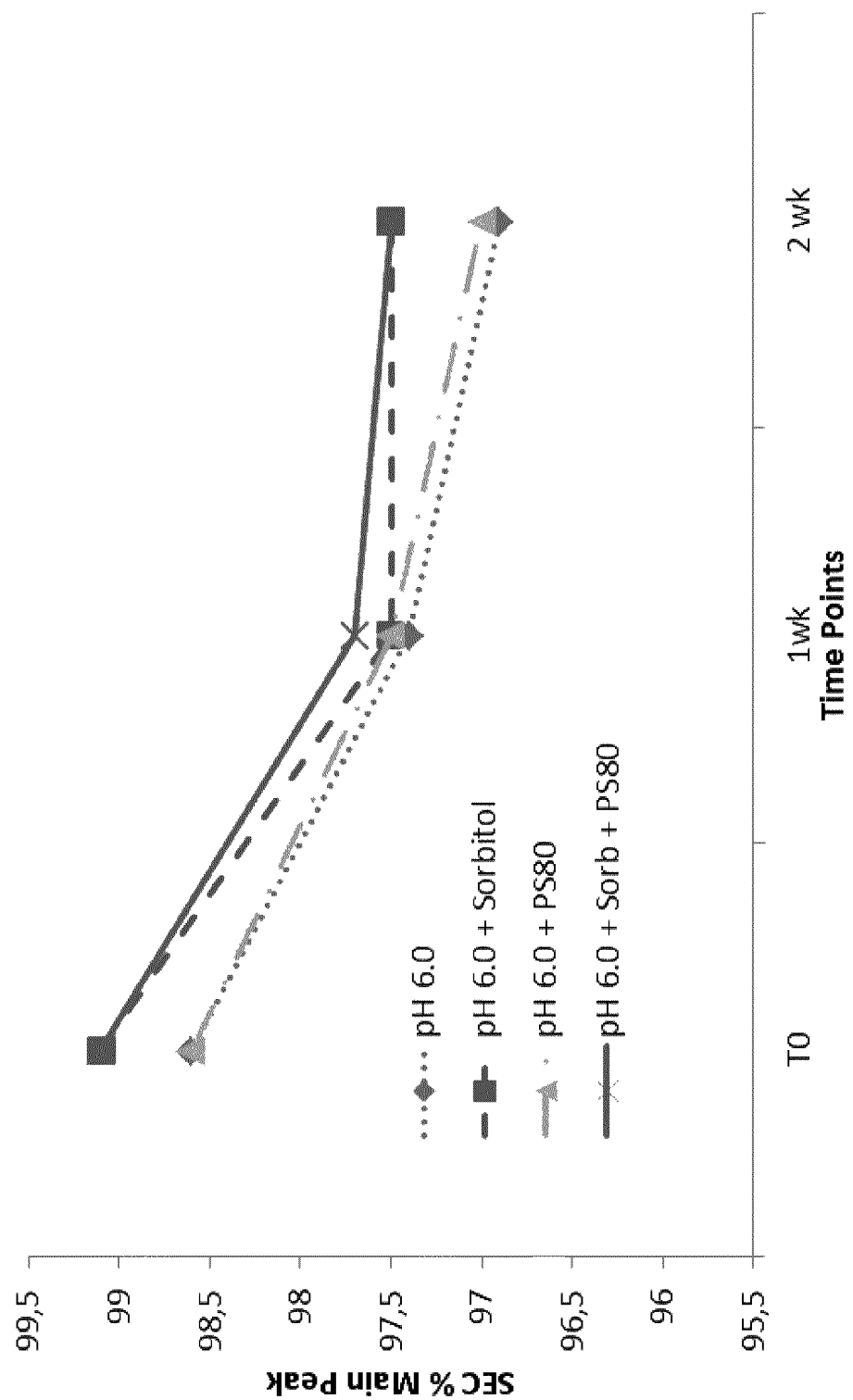
FIG. 5B shows the effect of sorbitol and PS80 (polysorbate 80) on main peak (by SEC) of HuMax TF ADC solutions prepared at pH 6.0 and stored at 40° C. for 2 weeks. See Example 5 for details.

The use of sorbitol or PS8 0 did not have any marked effect on the percent main charge peak by icI EF, as well as the main peak by SEC, in the HuMax-TF-ADC formulations stored at 40° C. for 2 weeks (FIGS. 5A and 5B). This shows that the formulation may be free of surfactants.

EXAMPLE 6

Figure 6:
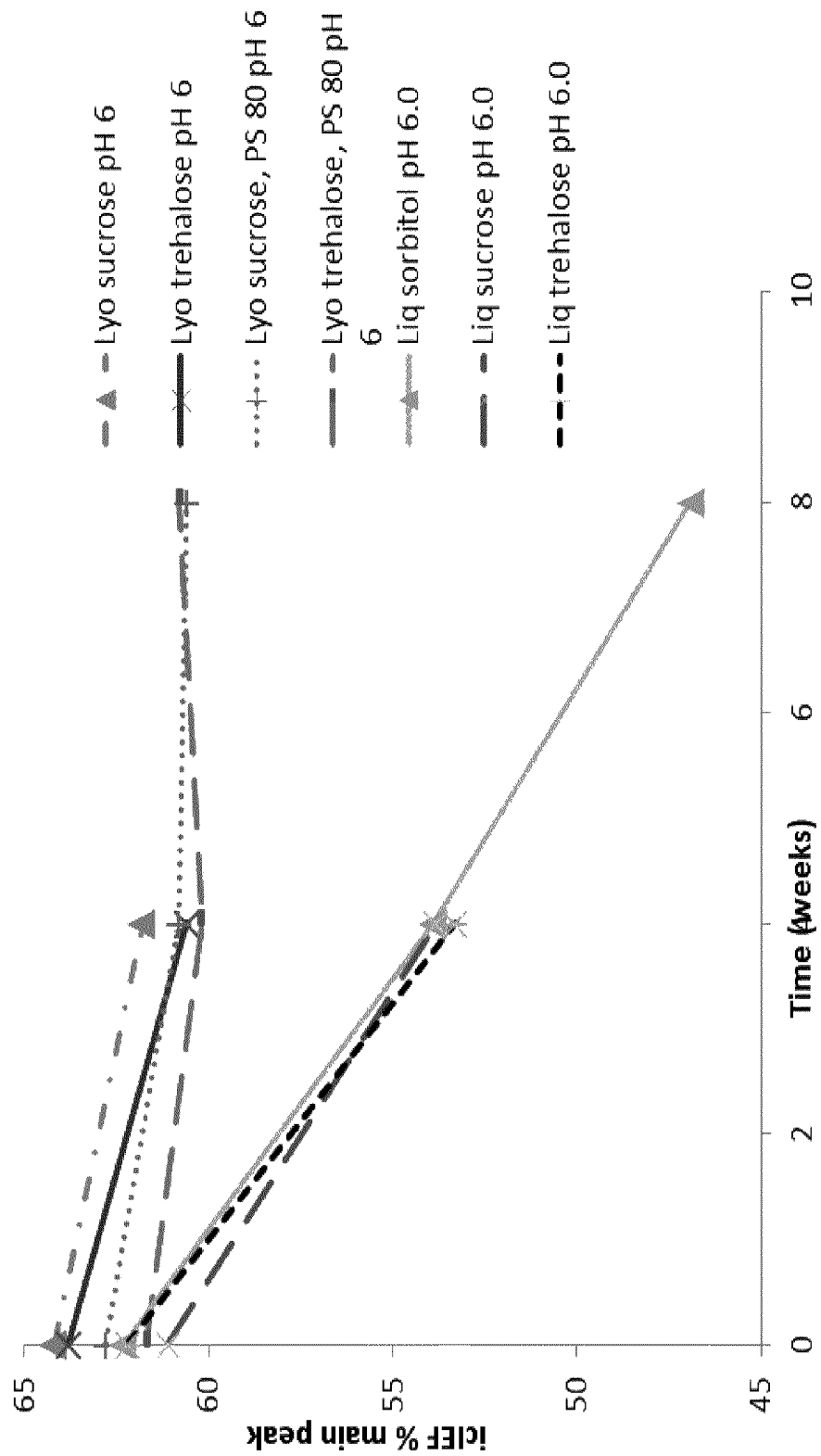
FIG. 6 shows a comparison between liquid and lyophilized formulations on main charge isoform percentage of HuMax-TF-ADC stored at 40° C. for 2 weeks. See Example 6 for details.

Formulation screening had shown that the main stability indicating parameters were aggregates measured by SEC and acidic isoforms (presumably deamidation) measured by icI EF. The deamidation rate in all tested liquid formulations measured under accelerated conditions was fast, thus the tested liquid formulations of HuMax-TF-ADC were clearly unstable. A comparison between some liquid formulations and preliminary lyophilized formulations are shown in FIG. 6.

EXAMPLE 7

A pilot lyophilization study was conducted with two formulations containing different concentrations of sucrose (150 mM and 250 mM), 10 mg/mL HuMax-TF-ADC in a 30 mM histidine buffer at pH 6.0 to investigate the possible influence of the fill volume and vial volume/shape on the lyophilized cake. For the histidine, sucrose formulation of HuMax-TF-ADC, the lyophilized cake appearances were different by different fill volumes and vial sizes:

A: The first group of samples of a formulation were filled into 0.25 mL per 2 mL glass vials and lyophilized. The samples appeared pharmaceutically elegant with no obvious signs of collapse.

B: The second group of samples with the same formulation were concurrently being lyophilized using a 4 mL fill volume in a 10 mL vial, using the same lyophilization cycle. The samples appeared with severe shrinkage.

Accordingly, the formulation could support a pharmaceutically elegant cake for a low fill volume 0.25 ml in a 2 mL glass vial, but is less suitable for a higher fill volume of 4 mL in a 10 mL vial.

EXAMPLE 8

The objective of this example was to test the effects of sucrose and mannitol concentrations on the stability of lyophilized formulations for HuMax-TF-ADC.

Initial tests showed that sucrose may be readily substituted with trehalose, maintaining the primary properties of the formulation. Testing continued using sucrose only.

Three different lyophilized formulations containing 10 mg/mL HuMax-TF-ADC, 30 mM histidine, at pH 6.0 were prepared with different concentrations of sucrose and mannitol. The details are shown in Table 4.

TABLE 4

| Formulation | HuMax-TF-ADC | Histidine | Sucrose | Mannitol |
|---|---|---|---|---|
| A | 10 mg/mL | 30 mM | 225 mM (7.7% w/v) | 274 mM (5% w/v) |
| B | 10 mg/mL | 30 mM | 88 mM (3% w/v) | 165 mM (3% w/v) |
| C | 10 mg/mL | 30 mM | 160 mM (5.5% w/v) | 274 mM (5% w/v) |

Figures 7A, 7B:
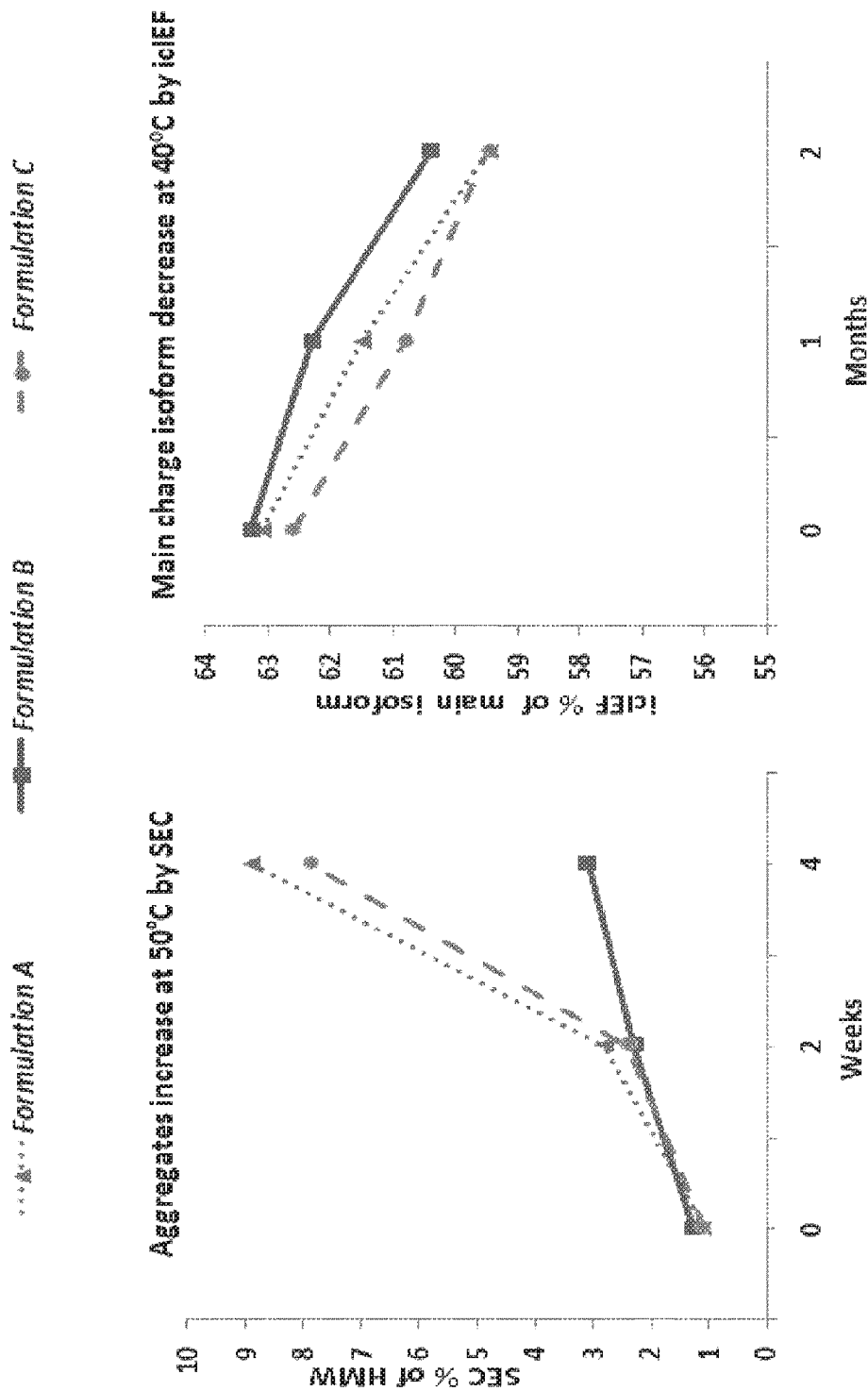
FIGS. 7A and 7B show exemplary results from accelerated stability data for different lyophilized formulations for HuMax-TF-ADC.

Lyophilized formulations with different concentrations of sucrose and mannitol were placed on accelerated stability tests at 25° C., 40° C., and 50° C. The stressed samples were analyzed by methods such as SEC (Size Exclusion Chromatography), icI EF (Imaged Capillary Isoelectric Focusing), FTIR (Fourier transform infrared spectroscopy), DLS (Dynamic Light Scattering. The accelerated stability data for the 3 formulations showed that formulation B had an advantage over the other formulations regarding the aggregates and main charge isoform, especially when comparing the stability data at 50° C. and 40° C. Exemplary results are shown in FIG. 7.

Figure 8:
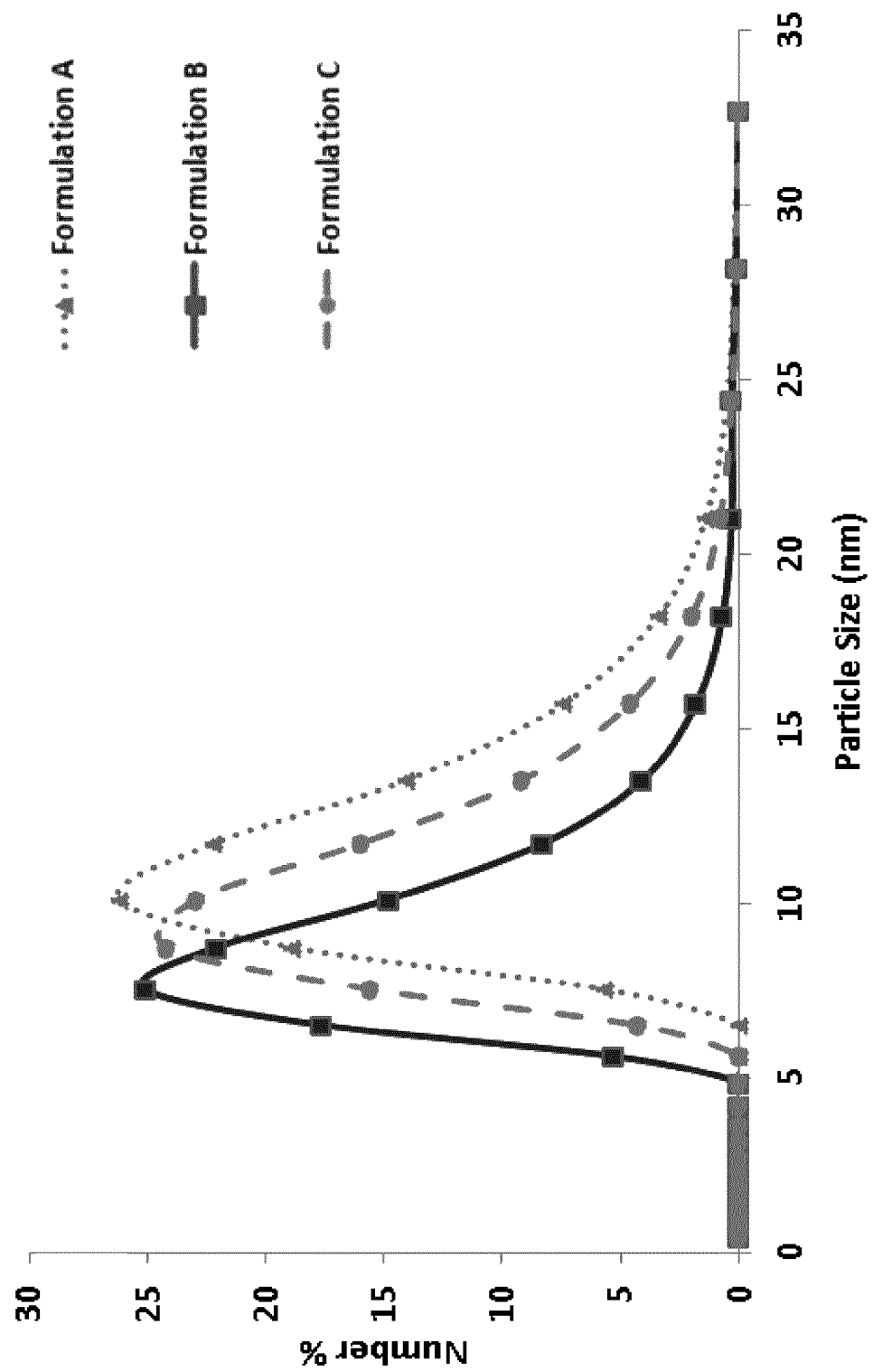
FIG. 8 shows DLS particle size distributions for lyophilized formulations A, B and C after storage at 40° C. for 2 months. See Example 8 for details.

Furthermore, formulation B exhibited the least growth in more particles after storage at 40° C. for 2 months, when compared to formulations A and C (FIG. 8).

No apparent changes in the amide I region of second derivative FTIR spectra for formulations A, B, and C were observed after storage at 50° C. for 2 weeks (FIG. 9). The data suggested that the secondary structure for the molecule remained the same in each formulation when stored under stressed temperature conditions.

EXAMPLE 11

This example verified the suitability of mannitol as a crystalline bulking agent in the HuMax-TF-ADC formulation, especially, the annealing temperature and time for the crystallization of mannitol in the lyophilized formulation for HuMax-TF-ADC. Differential scanning calorimetry (DSC) is a thermo analytical technique which measures energy directly and allows precise measurements of heat capacity of samples. When the sample undergoes a physical transformation such as phase transitions, the difference in heat flow between the sample and reference can be detected by DSC.

In the current example, DSC was used to determine the time required for the onset of the crystallization of mannitol in the formulation. Two different annealing temperatures (−15° C. and −20° C.) were tested. After the solutions were cooled to −40° C. at 1° C./min, the temperature were ramped to either −15° C. or −20° C. at 1° C./min, and held isothermally for 120 minutes. The onset time for the crystallization of mannitol for Formulation B was approximately 10 minutes when annealed at −15° C. or −20° C., as shown in FIG. 10. The data demonstrated that mannitol readily crystallized during annealing, thus function well as the crystalline bulking agent in the formulation.

EXAMPLE 10

Lyophilized HuMax TF-ADC formulation samples were evaluated on long-term and accelerated stability programs. The composition of HuMax-TF-ADC formulation after reconstitution is 10 mg/mL formulated in 30 mM histidine (corresponding to 4.65 mg/mL), 88 mM sucrose (corresponding to around 30 mg/mL), 165 mM mannitol (corresponding to around 30 mg/mL), pH 6.0. The long term stability samples were analysed at time zero, 1 month, 2 month, 3 months, 6 months, 9 months, 12 months and 18 months, etc. The lyophilized formulation was, at the different time points, reconstituted with water for injection (WFI) and tested by analytical methods including SEC, HIC, CE-SDS and icI EF.

After at least 6 months storage at 5±3° C. and 25±2° C., all samples remained stable by all test methods. The samples stored at 5±3° C. and 25±2° C. showed no significant changes by any test methods at at least 6 month time point compared to the study start. Expected minor changes in the purity profile during accelerated stability testing at 25° C. were observed by icI EF, reduced CE-SDS, and SEC testing.

In particular, with respect to aggregation, SEC analysis showed that the percentage of aggregates remained at around 2.2% for samples both at 5±3° C. and at 25±2° C. over at least 6 months. IcI EF was used to determine changes to the charge profile of HuMax-TF-ADC. For samples stored at 5±3° C., the changes of main charge isoform are within 0.4% and for samples stored at 25° C., the change is only 1.7%, over at least 6 months compared to time zero.

Furthermore, the average DAR (moles auristatins/moles mAb), drug load and free drug remains almost constant over at least 6 month at both 5° C. and 25 C. There are no sign of degradation over at least 6 month both at 5° C. and 25° C., as shown by CE-SDS (non-reduced) and CE-SDS (reduced), as well as LMW by SEC. Last but not least, the bioassay by Cytotoxcity proved the biological functional of HuMaxTF-ADC could be preserved for at least 6 month at both 5° C. and 25° C. Therefore HuMax-TF-ADC in such a formulation is acceptably stable for pharmaceutical use.

TABLE 5A

Example data from stability program of HuMax-TF-ADC drug product at 5 ± 3° C.

| Assay | Time point (months) | | | | |
|---|---|---|---|---|---|
| | 0 | 1 | 2 | 3 | 6 |
| SEC % main | 97.6 | 97.7 | 97.8 | 97.7 | 97.6 |
| SEC % HMW | 2.3 | 2.2 | 2.1 | 2.2 | 2.2 |
| SEC % LMW | 0.1 | 0.1 | 0.1 | 0.1 | 0.2 |
| Average DAR by HIC (moles auristatins/moles mAb) | 4.1 | 4.1 | 4.1 | 4.1 | 4.1 |
| Drug load or unconjugated antibody by HIC (area %) | 1.9 | 1.8 | 1.9 | 1.8 | 1.8 |
| CE-SDS (non-reduced) | CR | CR | CR | CR | CR |
| CE-SDS (reduced) | CR | CR | CR | CR | CR |
| CE-SDS (reduced) % LC0 + LC1 | 31.8 | 31.9 | 32.8 | 32.0 | 30.5 |
| CE-SDS (reduced) % HC | 66.2 | 65.9 | 65.3 | 65.9 | 67.2 |
| CE-SDS (reduced) LC0 + LC1 + HC | 98.0 | 97.8 | 98.1 | 97.9 | 97.7 |
| Free Drug (w/w % free drug/mAb) | <0.01 | <0.01 | <0.01 | <0.01 | <0.01 |
| icI EF % Main | 70.3 | 70.7 | NA | 69.6 | 69.9 |
| icI EF % Acidic | 25.2 | 24.2 | NA | 24.7 | 25.2 |

TABLE 5A-continued

Example data from stability program of HuMax-TF-ADC drug product at 5 ± 3° C.

| Assay | Time point (months) | | | | |
|---|---|---|---|---|---|
| | 0 | 1 | 2 | 3 | 6 |
| icl EF % Basic | 4.5 | 5.2 | NA | 5.7 | 4.9 |
| Cytotoxcity (based on reference standard) | 106 | 102 | 111 | 122 | 100 |
| Visible Particulates | Practically free from visible particles | Practically free from visible particles | Practically free from visible particles | Practically free from visible particles | Practically free from visible particles |

CR = Comparable to reference standard;
HC = Heavy chain;
LC = Light chain;
TQI = Total quantifiable impurities;
NT = Not tested;
NA = Not analyzed

TABLE 5B

Example data from stability program of HuMax-TF-ADC drug product at 25 ± 3° C.

| Assay | Time point (months) | | | | |
|---|---|---|---|---|---|
| | 0 | 1 | 2 | 3 | 6 |
| SEC % main | 97.6 | 97.6 | 97.7 | 97.7 | 97.6 |
| SEC % HMW | 2.3 | 2.3 | 2.2 | 2.2 | 2.2 |
| SEC % LMW | 0.1 | 0.1 | 0.1 | 0.1 | 0.2 |
| Average DAR by HIC (moles auristatins/moles mAb) | 4.1 | 4.1 | 4.1 | 4.1 | 4.1 |
| Drug load by HIC (area %) | 1.9 | 1.8 | 1.9 | 1.8 | 1.8 |
| CE-SDS (non-reduced) | CR | CR | CR | CR | CR |
| CE-SDS (reduced) | CR | CR | CR | CR | CR |
| CE-SDS (reduced) % LC0 + LC1 | 31.8 | 32.0 | 32.8 | 32.0 | 30.8 |
| CE-SDS (reduced) % HC | 66.2 | 66.1 | 65.3 | 65.8 | 66.8 |
| CE-SDS (reduced) LC0 + LC1 + HC | 98.0 | 98.1 | 98.1 | 97.8 | 97.6 |
| Free Drug (w/w % free drug/mAb) | <0.01 | <0.01 | <0.01 | <0.01 | <0.01 |
| icl EF % Main | 70.3 | 69.8 | NA | 68.6 | 68.6 |
| icl EF % Acidic | 25.2 | 24.7 | NA | 25.1 | 25.6 |
| icl EF % Basic | 4.5 | 5.4 | NA | 6.3 | 5.9 |
| Cytotoxcity (based on reference standard) | 106 | 109 | 104 | 111 | 98 |
| Visible Particulates | Practically free from visible particles | Practically free from visible particles | Practically free from visible particles | Practically free from visible particles | Practically free from visible particles |

CR = Comparable to reference standard;
HC = Heavy chain;
LC = Light chain;
TQI = Total quantifiable impurities;
NT = Not tested;
NA = Not analyzed

EXAMPLE 11

This study was to examine the effect of higher or lower excipient concentrations on the stability of HuMax-TF-ADC, in order to verify the acceptable range for excipient concentrations. Three formulations of HuMax-TF-ADC were prepared according to Table 6. The solutions were filled into 10 mL glass vials at 4 mL per vial and lyophilized. Samples of each formulation were placed on accelerated stability at 50° C. for 4 weeks and sampled after 2, 3, and 4 weeks. The samples were tested for concentration, pH, reconstitution time, appearance, iCE, CE-SDS, SEC, DAR-HIC, Free drugDLS, and MFI, in order to obtain data to evaluate the impact of higher or lower concentration of excipients on the stability of HuMax-TF-ADC. The data showed that the formulations behaved similarly in stressed stability testing.

TABLE 6

| Description | Concentration of excipients | | |
|---|---|---|---|
| | Histidine | Sucrose | Mannitol |
| Lower Excipient Concentration | 29.5 mM/4.58 g/L | 84 mM/28.75 g/L | 158 mM/28.78 g/L |
| Target Formulation | 30 mM/4.65 g/L | 88 mM/30.12 g/L | 165 mM/30.06 g/L |
| Higher Excipient Concentration | 30.5 mM/4.73 g/L | 92 mM/31.49 g/L | 172 mM/31.33 g/L |

EXAMPLE 12

The effect of the HuMax-TF-ADC concentrations on the stability of lyophilized HuMax-TF-ADC formulations was examined, in order to verify the acceptable range for HuMax-TF-ADC concentrations in the formulation.

The formulations prepared by 30 mM histidine, 88 mM sucrose, 165 mM mannitol, and 5 mg/mL or 30 mg/mL HuMax-TF-ADC were lyophilized and stored at 40° C. for 2 months or at 50° C. for 2 weeks. The main peak by SEC after 2 months storage at 40° C. stayed above 97% (FIG. 12), only slight increases in the average percent high molecular weight species were observed for both concentrations after storage at 40° C. (FIG. 13). The trends of charge profile change under stressed conditions, as shown by ICE data, are similar for both concentrations (FIGS. 14, 15 and 16).

This shows that the HuMax-TF-ADC may be formulated at least at concentrations in the range of 5 mg/mL and 30 mg/mL.

EXAMPLE 13

The in-use stability of HuMax-TF-ADC were studied in different concentrations (up to 48 mg/ml) and different diluents, i.e. water for injection (WFI), 0.9% NaCl(saline) and dextrose 5% (D5W) solution, for at least 48 hours at room temperature.

Figure 18:
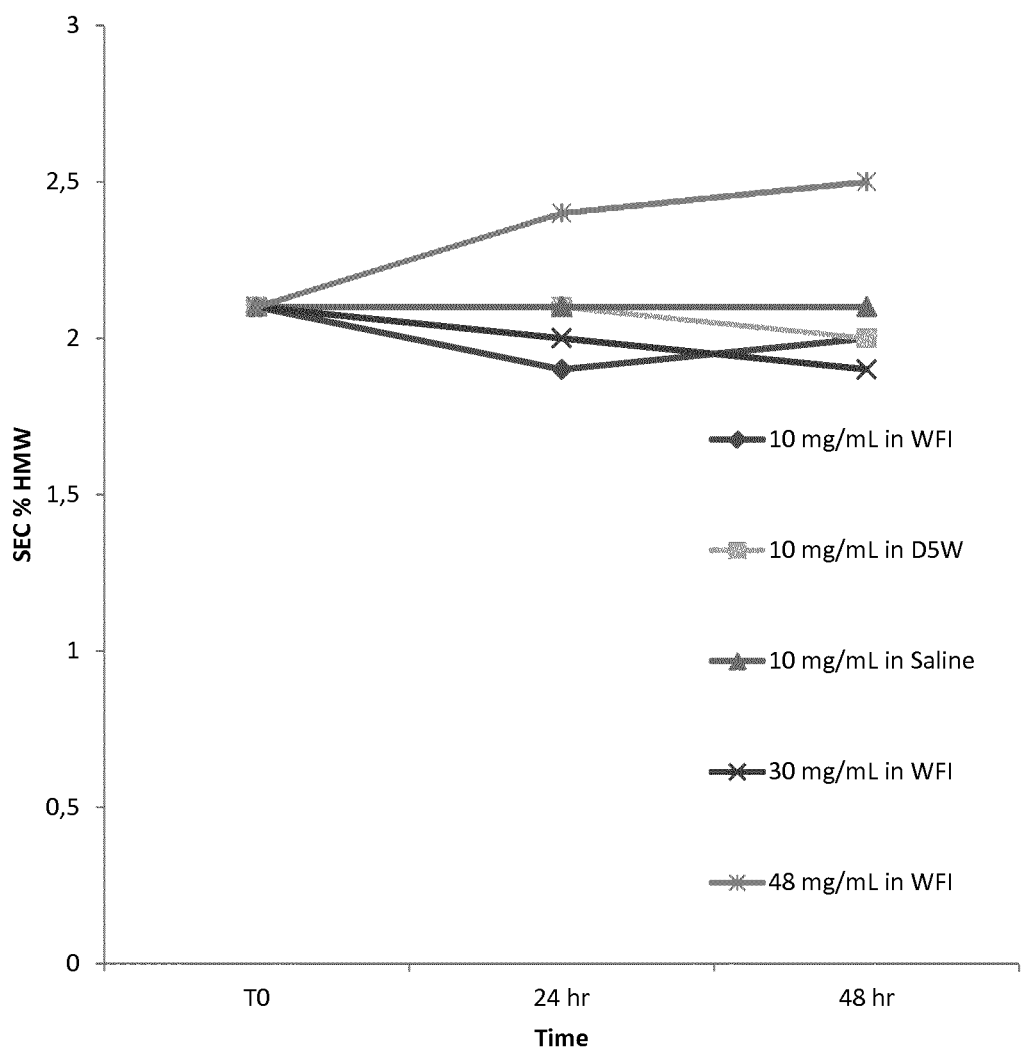

SEC data showed that the average percent main peak remained greater than 97% for the samples stored at 25° C. for 48 hours (FIG. 17). The 48 mg/mL samples contained approximately 0.5% more high molecular weight species than the other samples (FIG. 18). Different diluents did not influence the aggregation propensity.

The in-use solution samples stored at 25° C. were also examined using iCE. The sample reconstituted with 5% dextrose had the lowest percent main peak (FIG. 19) after 48 hours, and the highest percent acidic species (FIG. 20) when compared to the other samples. This indicates that WFI and saline are potentially better dilute to preserve the charge profile of the HuMax-TF-ADC.

EXAMPLE 14

The effect of buffer type and crystallizing excipient type on the stability of HuMax-TF-ADC formulations are demonstrated in this example.

When replacing histidine by citrate as a buffer in the lyophilized formulation, or when replacing mannitol by glycine as a crystallizing excipient, their stability was analysed by SEC and iCE, after storage at 40° C. for 2 months.

In FIG. 22 to FIG. 26, the legend "Glycine" refers to the formulation containing 10 mg/mL HuMax-TF-ADC, 30 mM histidine, 88 mM sucrose, 165 mM glycine, pH 6.0; whereas the legend "Citrate" refers the formulation containing 10 mg/mL HuMax-TF-ADC, 30 mM citrate, 88 mM sucrose, 165 mM mannitol, pH 6.0.

No marked changes in the SEC average percent main peak (FIG. 22) or high molecular peak (FIG. 23) were observed in the citrate or glycine formulations after storage at 40° C. for 2 months. No low molecular peaks were observed in any of the samples.

The decreasing rate of iCE percent main peak at 40° C. for 2 months in the formulations containing glycine and citrate were (FIG. 24) comparable to the formulation containing 30 mM Histindine, 88 mM (3%) Sucrose and 165 mM (3%) Mannitol (FIG. 7). It is observed that under heat stressed conditions, the citrate formulation was associated with more acidic species compared to formulation with Histidine (FIG. 25) and the glycine formulation was associated with more basic species compared to formulation with mannitol (FIG. 26).

EXAMPLE 15

The effects of pH and buffer concentrations on the stability of HuMax-TF-ADC were demonstrated in this example. HuMax-TF-ADC was prepared at 10 mg/mL concentration with 3% mannitol and 3% sucrose but with either 20 mM or 50 mM histidine with the pH of the samples adjusted to 5, 6, or 7. The lyophilized samples were stored at 40° C. for up to 2 months. The formulations prepared with 20 mM histidine or 50 mM histidine at pH 5, 6 or 7 exhibited similar SEC results at 40° C. regardless of buffer concentration and pH, except that the formulation with 50 mM histidine at pH 5 showed a slight increase in aggregation (FIGS. 30 and 31).

As shown in FIG. 27-29 by iCE, it is observed that pH play a more important role than the buffer concentration regarding the charge profile change under stressed testing. The formulations prepared at pH 6 displayed the least decrease in main peak during 2 month at 40° C. storage. An apparent decrease in the main peak is observed, which is potentially larger than the analytical method variation. The formulation prepared at pH 5 exhibited the largest decrease in percent main peak (FIG. 27). The formulation prepared at pH 7 had the highest percentage of acidic species (FIG. 28) and the formulation prepared at pH 5 had the highest percentage of basic species (FIG. 29).

EXAMPLE 16

The lyophilization cycle for the lyophilized formulation of HuMax-TF-ADC of the invention may be performed as described below.

Firstly, the vials may be cooled at 0.5° C./min to 1° C./min to −40° C. or less and held isothermally for at least 120 min (cooling step). Subsequently the vials are warmed to between −20° C. and −15° C. at a rate of 0.5° C./min to 3° C./min and held isothermally for at least 180 min (annealing step). Afterwards Vacuum is initiated using a pressure between 50 mTorr and 200 mTorr with a temperature between −30° C. and −10° C. (primary drying). Lastly, the temperature is increased to between 35° C. and 50° C. at between 0.5° C./min and 1° C./min and held isothermally for at least 10 hours (secondary drying). The residual moisture should not be more than 2% by weight.

LIST OF REFERENCES

WO2011157741, WO9704801, WO9856418, WO02011753, WO02096457, WO03009817, WO03039485, U.S. Pat. No. 8,372,396, WO2004004639, WO2004016286, WO2004055164, WO 2004071439, WO2006014965, WO2006044908 and WO2007019232.
Physicochemical Stability of the Antibody—Drug Conjugate Trastuzumab-DM1: Changes due to Modification and Conjugation Processes. Aditya A. Wakankar, et al., Bioconjugate Chemistry 2010: 21 (9), 1588-1595
Challenges in developing bioanalytical assays for characterization of antibody-drug conjugates. Stephan J P, etc, Bioanalysis. 2011 March; 3(6):677-700
Analytical methods for physicochemical characterization of antibody drug conjugates. Wakankar A, et al., MAbs. 2011 March-April; 3(2):161-72.
Analytical and bioanalytical technologies for characterizing antibody—drug conjugates, Stephen C Alley, Kevin E Anderson, Current Opinion in Chemical Biology, June 2013, 17 (3), 406-411
Effect of Polysorbate 80 Quality on Photostability of a Monoclonal Antibody, Singh et al., AAPS PharmSciTech, Vol. 13, No. 2, 2012.
Polysorbates 20 and 80 Used in the Formulation of Protein Biotherapeutics: Structure and Degradation Pathways. BRUCE A. KERWIN, JOURNAL OF PHARMACEUTICAL SCIENCES, VOL. 97, NO. 8, AUGUST 2008, 2924-2935.
Aggregates in monoclonal antibody manufacturing processes, Vásquez-Rey and Lang, 2011, Biotech, Bioeng. 108(7) p. 1494-1508.

The invention claimed is:

1. A lyophilized formulation of an anti-tissue factor (TF) antibody-drug conjugate (ADC), the lyophilized formulation obtainable or obtained by lyophilizing an aqueous formulation comprising said anti-TF ADC and pharmaceutically acceptable excipients, wherein:
  (a) the lyophilized formulation is free of surfactant,
  (b) the anti-TF antibody portion of the ADC comprises a variable heavy (VH) region comprising a CDR1 region having the amino acid sequence set forth in SEQ ID NO: 6, a CDR2 region having the amino acid sequence set forth in SEQ ID NO: 7, and a CDR3 region having the amino acid sequence set forth in SEQ ID NO: 8, and a variable light (VL) region comprising a CDR1 region having the amino acid sequence set forth in SEQ ID NO:46, a CDR2 region having the amino acid sequence set forth in SEQ ID NO: 47, and a CDR3 region having the amino acid sequence set forth in SEQ ID NO: 48, and
  (c) the drug portion of the ADC comprises vcMMAE.

2. The lyophilized formulation of claim 1, wherein the pharmaceutically acceptable excipients comprise:
  a) a buffer which limits pH shifts during the lyophilizing step so that pH is kept between about 5 and about 7,
  b) at least one non-reducing sugar which forms an amorphous phase with the anti-TF ADC in solid state; and
  c) at least one bulking agent.

3. The lyophilized formulation of claim 1, wherein the aqueous formulation comprises a buffer selected from the group consisting of histidine, citrate, phosphate, carbonic acid, succinate, glycolate and a combination of any thereof.

4. The lyophilized formulation of claim 2, wherein the aqueous formulation comprises the buffer at a concentration of about 20 to about 50 mM.

5. The lyophilized formulation of claim 2, wherein the non-reducing sugar is selected from sucrose, trehalose and a combination thereof.

6. The lyophilized formulation of claim 2, wherein the aqueous formulation comprises the non-reducing sugar at a concentration of about 10 to about 250 mM.

7. The lyophilized formulation of claim 2, wherein the bulking agent is selected from mannitol and glycine.

8. The lyophilized formulation of claim 2, wherein the aqueous formulation comprises the bulking agent at a concentration of about 50 mM to about 300 mM.

9. The lyophilized formulation of claim 1, wherein the aqueous formulation comprises from about 5 g/L to about 30 g/L anti-TF ADC.

10. The lyophilized formulation of claim 1, wherein the pH of the aqueous formulation is in a range from about 5.5 to 6.5.

11. The lyophilized formulation of claim 1, comprising mannitol and sucrose, wherein the weight by weight ratio of mannitol to sucrose is between about 1:1 and about 30:1.

12. The lyophilized formulation of claim 1, comprising mannitol and sucrose, wherein the weight by weight ratio of mannitol to anti-TF ADC is about 3:1 and the weight by weight ratio of mannitol to sucrose is about 1:1.

13. The lyophilized formulation of claim 1, which is obtainable or obtained by lyophilizing an aqueous formulation comprising about 5 g/L to about 30 g/L anti-TF ADC and pharmaceutically acceptable excipients comprising:
  a. about 20 to about 50 mM histidine or citrate buffer having a pH of about 5 to about 7;
  b. about 10 to about 250 mM sucrose or trehalose; and
  c. about 50 mM to about 300 mM mannitol or glycine.

14. The lyophilized formulation of claim 1, wherein the aqueous formulation comprises from about 9 to about 11 g/L anti-TF ADC.

15. The lyophilized formulation of claim 1, wherein the antibody comprises
a VH region comprising an amino acid sequence of SEQ ID NO: 5 and a VL region comprising an amino acid sequence of SEQ ID NO: 45.

16. The lyophilized formulation of claim 1, wherein the average absolute number of drug moieties per antibody molecule is 1, 2, 3, 4, 5, 6, 7, or 8.

17. The lyophilized formulation of claim 1, wherein the anti-TF antibody is a full-length antibody.

18. The lyophilized formulation of claim 1, which is obtainable or obtained by lyophilizing an aqueous formulation comprising about 9 g/L to about 11 g/L anti-TF ADC and pharmaceutically acceptable excipients comprising: about 30 mM histidine buffer having a pH of about 5 to about 7; about 88 mM sucrose; and about 165 mM mannitol; wherein the antibody comprises a VH region comprising an amino acid sequence of SEQ ID NO: 5 and a VL region comprising an amino acid sequence of SEQ ID NO: 45.

19. The lyophilized formulation of claim 1, wherein the anti-TF ADC is stable at 2-8° C. for pharmaceutical use for at least 6 months.

20. The lyophilized formulation of claim 19, wherein the formulation is stable when it has less than 3.0% aggregates when stored at 5° C. for at least 6 months.

21. The lyophilized formulation of claim 19 wherein the stability is determined by SEC analysis according to Example 10.

22. The lyophilized formulation of claim 1, which lyophilized formulation contains less than 3.0 wt. % moisture.

23. The lyophilized formulation of claim 1, wherein the formulation is free of any inorganic salts.

24. An aqueous solution suitable for preparing a lyophilized formulation of an anti-TF ADC, comprising:

a. from about 7 to about 20 g/L anti-TF ADC of claim 1;
b. about 28 to 34 mM histidine;
c. about 84 to about 146 mM sucrose;
d. about 158 to about 274 mannitol.

25. A pharmaceutically acceptable liquid formulation obtained by reconstituting the lyophilized formulation of claim 1 in a sterile aqueous diluent.

26. The liquid formulation of claim 25, comprising about 5 g/L to about 30 g/L anti-TF ADC, about 20 to about 50 mM histidine having a pH of about 5 to about 7; about 10 to about 250 mM sucrose or trehalose; and about 50 mM to about 300 mM mannitol or glycine.

27. A method for preparing a lyophilized formulation of claim 1 comprising the steps of:

a. cooling the aqueous solution at a rate of from 0.5° C./min to 1° C./min to a temperature of −40° C. or less;
b. holding isothermally for at least 120 min;
c. warming to between −20° C. and −15° C. at a rate of from 0.5° C./min to 3° C./min;
d. holding isothermally for at least 180 min;
e. applying vacuum using a pressure between 50 mTorr and 200 mTorr at a temperature between −30° C. and −10° C.;
f. increasing the temperature to between 35° C. and 50° C. at a rate of from 0.5° C./min and 1° C./min and
g. holding isothermally for at least 10 hours.

28. A method of preparing an injectable solution of an anti-TF ADC, comprising the step of reconstituting the lyophilized formulation of claim 1 in a sterile aqueous diluent.

* * * * *

UNITED STATES PATENT AND TRADEMARK OFFICE
CERTIFICATE OF CORRECTION

PATENT NO. : 10,617,764 B2
APPLICATION NO. : 15/038235
DATED : April 14, 2020
INVENTOR(S) : Jesper Valbjørn et al.

It is certified that error appears in the above-identified patent and that said Letters Patent is hereby corrected as shown below:

In the Specification

At Column 3, Line number 53, delete "See Example 11 for details" and insert --See Example 9 for details--.

At Column 39, Line number 16, delete "EXAMPLE 11" and insert --EXAMPLE 9--.

Signed and Sealed this
Twenty-first Day of July, 2020

Andrei Iancu
*Director of the United States Patent and Trademark Office*

SEQUENCE LISTING

```
<160> NUMBER OF SEQ ID NOS: 80

<210> SEQ ID NO 1
<211> LENGTH: 119
<212> TYPE: PRT
<213> ORGANISM: homo sapiens

<400> SEQUENCE: 1

Gln Val Gln Leu Val Glu Ser Gly Gly Val Val Gln Pro Gly Arg
1               5                   10                  15

Ser Leu Arg Leu Ser Cys Val Ala Ser Gly Phe Thr Val Ser Asn Asp
            20                  25                  30

Gly Met His Trp Val Arg Gln Ala Pro Gly Lys Gly Leu Glu Trp Val
        35                  40                  45

Ala Leu Ile Trp Tyr Asp Gly Val Asn Lys Asn Tyr Ala Asp Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Pro Gly Thr Phe Tyr Gly Leu Asp Val Trp Gly Gln Gly
            100                 105                 110

Thr Thr Val Thr Val Ser Ser
        115

<210> SEQ ID NO 2
<211> LENGTH: 8
<212> TYPE: PRT
<213> ORGANISM: homo sapiens

<400> SEQUENCE: 2

Gly Phe Thr Val Ser Asn Asp Gly
1               5

<210> SEQ ID NO 3
<211> LENGTH: 8
<212> TYPE: PRT
<213> ORGANISM: homo sapiens
```

-continued

```
<400> SEQUENCE: 3

Ile Trp Tyr Asp Gly Val Asn Lys
1               5

<210> SEQ ID NO 4
<211> LENGTH: 12
<212> TYPE: PRT
<213> ORGANISM: homo sapiens

<400> SEQUENCE: 4

Ala Arg Arg Pro Gly Thr Phe Tyr Gly Leu Asp Val
1               5                   10

<210> SEQ ID NO 5
<211> LENGTH: 118
<212> TYPE: PRT
<213> ORGANISM: homo sapiens

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

<210> SEQ ID NO 6
<211> LENGTH: 8
<212> TYPE: PRT
<213> ORGANISM: homo sapiens

<400> SEQUENCE: 6

Gly Phe Thr Phe Ser Asn Tyr Ala
1               5

<210> SEQ ID NO 7
<211> LENGTH: 8
<212> TYPE: PRT
<213> ORGANISM: homo sapiens

<400> SEQUENCE: 7

Ile Ser Gly Ser Gly Asp Tyr Thr
1               5

<210> SEQ ID NO 8
<211> LENGTH: 11
<212> TYPE: PRT
<213> ORGANISM: homo sapiens

<400> SEQUENCE: 8
```

Ala Arg Ser Pro Trp Gly Tyr Tyr Leu Asp Ser
1               5                   10

<210> SEQ ID NO 9
<211> LENGTH: 120
<212> TYPE: PRT
<213> ORGANISM: homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Phe Leu Leu Trp Tyr Phe Asp Leu Trp Gly Arg
            100                 105                 110

Gly Thr Leu Val Thr Val Ser Ser
            115                 120

<210> SEQ ID NO 10
<211> LENGTH: 8
<212> TYPE: PRT
<213> ORGANISM: homo sapiens

<400> SEQUENCE: 10

Gly Phe Thr Phe Ser Ser Tyr Ala
1               5

<210> SEQ ID NO 11
<211> LENGTH: 8
<212> TYPE: PRT
<213> ORGANISM: homo sapiens

<400> SEQUENCE: 11

Ile Ser Gly Ser Gly Asp Ser Thr
1               5

<210> SEQ ID NO 12
<211> LENGTH: 13
<212> TYPE: PRT
<213> ORGANISM: homo sapiens

<400> SEQUENCE: 12

Ala Lys Asp Gly Tyr Phe Leu Leu Trp Tyr Phe Asp Leu
1               5                   10

<210> SEQ ID NO 13
<211> LENGTH: 118
<212> TYPE: PRT
<213> ORGANISM: homo sapiens

<400> SEQUENCE: 13

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Gly Leu Glu Trp Val
            35                  40                  45

Ser Val Ile Ser Gly Ser Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ala Pro Trp Thr Tyr Tyr Phe Asp Tyr Trp Gly Gln Gly Thr
            100                 105                 110

Leu Val Thr Val Ser Ser
            115
```

<210> SEQ ID NO 14
<211> LENGTH: 8
<212> TYPE: PRT
<213> ORGANISM: homo sapiens

<400> SEQUENCE: 14

```
Gly Phe Thr Phe Ser Ser Tyr Gly
 1               5
```

<210> SEQ ID NO 15
<211> LENGTH: 8
<212> TYPE: PRT
<213> ORGANISM: homo sapiens

<400> SEQUENCE: 15

```
Ile Ser Gly Ser Gly Gly Thr Thr
 1               5
```

<210> SEQ ID NO 16
<211> LENGTH: 11
<212> TYPE: PRT
<213> ORGANISM: homo sapiens

<400> SEQUENCE: 16

```
Ala Lys Ala Pro Trp Thr Tyr Tyr Phe Asp Tyr
 1               5                   10
```

<210> SEQ ID NO 17
<211> LENGTH: 118
<212> TYPE: PRT
<213> ORGANISM: homo sapiens

<400> SEQUENCE: 17

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
                20                  25                  30

Ala Met Ser Trp Val Arg Gln Ala Pro Gly Lys Gly Leu Glu Trp Val
            35                  40                  45

Ser Ser Ile Ser Gly Ser Gly Gly Arg Thr Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                85                  90                  95
```

```
Ala Lys Thr Pro Trp Gly Tyr Tyr Phe Asp Tyr Trp Gly Gln Gly Thr
            100                 105                 110
Leu Val Thr Val Ser Ser
        115
```

<210> SEQ ID NO 18
<211> LENGTH: 8
<212> TYPE: PRT
<213> ORGANISM: homo sapiens

<400> SEQUENCE: 18

```
Gly Phe Thr Phe Asn Asn Tyr Ala
1               5
```

<210> SEQ ID NO 19
<211> LENGTH: 8
<212> TYPE: PRT
<213> ORGANISM: homo sapiens

<400> SEQUENCE: 19

```
Ile Ser Gly Ser Gly Gly Arg Thr
1               5
```

<210> SEQ ID NO 20
<211> LENGTH: 11
<212> TYPE: PRT
<213> ORGANISM: homo sapiens

<400> SEQUENCE: 20

```
Ala Lys Thr Pro Trp Gly Tyr Tyr Phe Asp Tyr
1               5                   10
```

<210> SEQ ID NO 21
<211> LENGTH: 118
<212> TYPE: PRT
<213> ORGANISM: homo sapiens

<400> SEQUENCE: 21

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Ala Lys Gly Leu Asp Trp Val
        35                  40                  45
Ser Gly Ile Ser Gly Ser Gly Val Thr Thr Tyr Tyr Ala Asp Ser Val
    50                  55                  60
Lys Gly Arg Phe Thr Ile Ser Arg Asp Asn Ser Lys Asp Thr Leu Tyr
65                  70                  75                  80
Leu Gln Met Asn Ser Leu Arg Ala Glu Asp Thr Ala Val Tyr Phe Cys
                85                  90                  95
Ala Lys Thr Pro Trp Gly Tyr Tyr Phe Asp Tyr Trp Gly Gln Gly Ile
            100                 105                 110
Leu Val Ala Val Ser Ser
        115
```

<210> SEQ ID NO 22
<211> LENGTH: 8
<212> TYPE: PRT
<213> ORGANISM: homo sapiens

<400> SEQUENCE: 22

Gly Phe Thr Phe Ser Asn Tyr Ala
1               5

<210> SEQ ID NO 23
<211> LENGTH: 8
<212> TYPE: PRT
<213> ORGANISM: homo sapiens

<400> SEQUENCE: 23

Ile Ser Gly Ser Gly Val Thr Thr
1               5

<210> SEQ ID NO 24
<211> LENGTH: 11
<212> TYPE: PRT
<213> ORGANISM: homo sapiens

<400> SEQUENCE: 24

Ala Lys Thr Pro Trp Gly Tyr Tyr Phe Asp Tyr
1               5                   10

<210> SEQ ID NO 25
<211> LENGTH: 120
<212> TYPE: PRT
<213> ORGANISM: homo sapiens

<400> SEQUENCE: 25

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Met His Trp Val Arg Gln Ala Pro Gly Lys Gly Leu Glu Trp Val
        35                  40                  45

Ala Val Ile Ser Asn Asp Gly Tyr Asn Asp Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Leu Gly Arg Gly Tyr Phe Asp Tyr Trp Gly Gln
            100                 105                 110

Gly Thr Leu Val Thr Val Ser Ser
        115                 120

<210> SEQ ID NO 26
<211> LENGTH: 8
<212> TYPE: PRT
<213> ORGANISM: homo sapiens

<400> SEQUENCE: 26

Gly Phe Thr Phe Ser Arg Tyr Ala
1               5

<210> SEQ ID NO 27
<211> LENGTH: 8
<212> TYPE: PRT
<213> ORGANISM: homo sapiens

<400> SEQUENCE: 27

Ile Ser Asn Asp Gly Tyr Asn Asp
1               5

```
<210> SEQ ID NO 28
<211> LENGTH: 13
<212> TYPE: PRT
<213> ORGANISM: homo sapiens

<400> SEQUENCE: 28

Ala Arg Asp Gly Gln Leu Gly Arg Gly Tyr Phe Asp Tyr
1               5                   10

<210> SEQ ID NO 29
<211> LENGTH: 120
<212> TYPE: PRT
<213> ORGANISM: homo sapiens

<400> SEQUENCE: 29

Gln Val Gln Leu Val Glu Ser Gly Gly Val Val Gln Pro Gly Arg
1               5                   10                  15

Ser Leu Arg Leu Ser Cys Pro Ala Ser Gly Phe Thr Phe Ser Ile Tyr
            20                  25                  30

Ala Met His Trp Val Arg Gln Ala Pro Gly Lys Gly Leu Glu Trp Val
        35                  40                  45

Ala Val Val Ser Asn Asp Gly Tyr Asn Lys Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Leu Gly Arg Gly Tyr Phe Asp Tyr Trp Gly Gln
            100                 105                 110

Gly Thr Leu Val Thr Val Ser Ser
        115                 120

<210> SEQ ID NO 30
<211> LENGTH: 8
<212> TYPE: PRT
<213> ORGANISM: homo sapiens

<400> SEQUENCE: 30

Gly Phe Thr Phe Ser Ile Tyr Ala
1               5

<210> SEQ ID NO 31
<211> LENGTH: 8
<212> TYPE: PRT
<213> ORGANISM: homo sapiens

<400> SEQUENCE: 31

Val Ser Asn Asp Gly Tyr Asn Lys
1               5

<210> SEQ ID NO 32
<211> LENGTH: 13
<212> TYPE: PRT
<213> ORGANISM: homo sapiens

<400> SEQUENCE: 32

Ala Arg Asp Gly Gln Leu Gly Arg Gly Tyr Phe Asp Tyr
1               5                   10

<210> SEQ ID NO 33
```

```
<211> LENGTH: 118
<212> TYPE: PRT
<213> ORGANISM: homo sapiens

<400> SEQUENCE: 33

Gln Val Gln Leu Val Gln Ser Gly Ala Glu Val Arg Lys Pro Gly Ser
1               5                   10                  15

Ser Val Lys Val Ser Cys Lys Ala Ser Gly Gly Ser Phe Asn Asn Tyr
            20                  25                  30

Pro Ile Phe Trp Val Arg Gln Ala Pro Gly Gln Gly Phe Glu Trp Met
        35                  40                  45

Gly Arg Ile Ile Pro Ile Leu Gly Ile Thr Ala Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Gly Gly Asp Asp Leu Asp Ala Phe Asp Ile Trp Gly Gln Gly Thr
            100                 105                 110

Met Val Ser Val Ser Ser
        115

<210> SEQ ID NO 34
<211> LENGTH: 8
<212> TYPE: PRT
<213> ORGANISM: homo sapiens

<400> SEQUENCE: 34

Gly Gly Ser Phe Asn Asn Tyr Pro
1               5

<210> SEQ ID NO 35
<211> LENGTH: 8
<212> TYPE: PRT
<213> ORGANISM: homo sapiens

<400> SEQUENCE: 35

Ile Ile Pro Ile Leu Gly Ile Thr
1               5

<210> SEQ ID NO 36
<211> LENGTH: 11
<212> TYPE: PRT
<213> ORGANISM: homo sapiens

<400> SEQUENCE: 36

Ala Gly Gly Asp Asp Leu Asp Ala Phe Asp Ile
1               5                   10

<210> SEQ ID NO 37
<211> LENGTH: 120
<212> TYPE: PRT
<213> ORGANISM: homo sapiens

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Gly Ser Gly Phe Thr Phe Asn Arg Tyr
            20                  25                  30

Ala Met Tyr Trp Val Arg Gln Ala Pro Gly Lys Gly Leu Asp Trp Val
        35                  40                  45
```

```
Ala Val Ile Ser Asn Asp Gly Ile Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Thr Met Val Arg Gly Ala Phe Asp Tyr Trp Gly Gln
                100                 105                 110

Gly Thr Leu Val Thr Val Ser Ser
            115                 120
```

<210> SEQ ID NO 38
<211> LENGTH: 8
<212> TYPE: PRT
<213> ORGANISM: homo sapiens

<400> SEQUENCE: 38

```
Gly Phe Thr Phe Asn Arg Tyr Ala
1               5
```

<210> SEQ ID NO 39
<211> LENGTH: 8
<212> TYPE: PRT
<213> ORGANISM: homo sapiens

<400> SEQUENCE: 39

```
Ile Ser Asn Asp Gly Ile Asn Lys
1               5
```

<210> SEQ ID NO 40
<211> LENGTH: 13
<212> TYPE: PRT
<213> ORGANISM: homo sapiens

<400> SEQUENCE: 40

```
Ala Arg Asp His Thr Met Val Arg Gly Ala Phe Asp Tyr
1               5                   10
```

<210> SEQ ID NO 41
<211> LENGTH: 107
<212> TYPE: PRT
<213> ORGANISM: homo sapiens

<400> SEQUENCE: 41

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
                100                 105
```

<210> SEQ ID NO 42
<211> LENGTH: 7
<212> TYPE: PRT
<213> ORGANISM: homo sapiens

<400> SEQUENCE: 42

Gln Ser Val Ser Ser Ser Tyr
1               5

<210> SEQ ID NO 43
<211> LENGTH: 3
<212> TYPE: PRT
<213> ORGANISM: homo sapiens

<400> SEQUENCE: 43

Gly Ala Ser
1

<210> SEQ ID NO 44
<211> LENGTH: 8
<212> TYPE: PRT
<213> ORGANISM: homo sapiens

<400> SEQUENCE: 44

Gln Gln Tyr Gly Ser Ser Leu Thr
1               5

<210> SEQ ID NO 45
<211> LENGTH: 107
<212> TYPE: PRT
<213> ORGANISM: homo sapiens

<400> SEQUENCE: 45

Asp Ile Gln Met Thr Gln Ser Pro Ser Leu Ser Ala Ser Ala Gly
1               5                   10                  15

Asp Arg Val Thr Ile Thr Cys Arg Ala Ser Gln Gly Ile Ser Ser Arg
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 46
<211> LENGTH: 6
<212> TYPE: PRT
<213> ORGANISM: homo sapiens

<400> SEQUENCE: 46

Gln Gly Ile Ser Ser Arg
1               5

<210> SEQ ID NO 47
<211> LENGTH: 3
<212> TYPE: PRT
<213> ORGANISM: homo sapiens

<400> SEQUENCE: 47

```
Ala Ala Ser
1

<210> SEQ ID NO 48
<211> LENGTH: 9
<212> TYPE: PRT
<213> ORGANISM: homo sapiens

<400> SEQUENCE: 48

Gln Gln Tyr Asn Ser Tyr Pro Tyr Thr
1               5

<210> SEQ ID NO 49
<211> LENGTH: 108
<212> TYPE: PRT
<213> ORGANISM: homo sapiens

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 50
<211> LENGTH: 7
<212> TYPE: PRT
<213> ORGANISM: homo sapiens

<400> SEQUENCE: 50

Gln Ser Val Arg Ser Ser Tyr
1               5

<210> SEQ ID NO 51
<211> LENGTH: 3
<212> TYPE: PRT
<213> ORGANISM: homo sapiens

<400> SEQUENCE: 51

Gly Ala Ser
1

<210> SEQ ID NO 52
<211> LENGTH: 9
<212> TYPE: PRT
<213> ORGANISM: homo sapiens

<400> SEQUENCE: 52

Gln Gln Tyr Gly Ser Ser Pro Arg Thr
1               5

<210> SEQ ID NO 53
```

```
<211> LENGTH: 108
<212> TYPE: PRT
<213> ORGANISM: homo sapiens

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 54
<211> LENGTH: 7
<212> TYPE: PRT
<213> ORGANISM: homo sapiens

<400> SEQUENCE: 54

Gln Ser Val Gly Ser Ser Ser
1               5

<210> SEQ ID NO 55
<211> LENGTH: 3
<212> TYPE: PRT
<213> ORGANISM: homo sapiens

<400> SEQUENCE: 55

Gly Ala Ser
1

<210> SEQ ID NO 56
<211> LENGTH: 9
<212> TYPE: PRT
<213> ORGANISM: homo sapiens

<400> SEQUENCE: 56

Gln Gln Tyr Gly Ser Ser Pro Arg Thr
1               5

<210> SEQ ID NO 57
<211> LENGTH: 107
<212> TYPE: PRT
<213> ORGANISM: homo sapiens

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 58
<211> LENGTH: 6
<212> TYPE: PRT
<213> ORGANISM: homo sapiens

<400> SEQUENCE: 58

Gln Gly Ile Ser Ser Arg
1               5

<210> SEQ ID NO 59
<211> LENGTH: 3
<212> TYPE: PRT
<213> ORGANISM: homo sapiens

<400> SEQUENCE: 59

Ala Ala Ser
1

<210> SEQ ID NO 60
<211> LENGTH: 9
<212> TYPE: PRT
<213> ORGANISM: homo sapiens

<400> SEQUENCE: 60

Gln Gln Tyr Asn Ser Tyr Pro Tyr Thr
1               5

<210> SEQ ID NO 61
<211> LENGTH: 108
<212> TYPE: PRT
<213> ORGANISM: homo sapiens

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Tyr Thr Phe Gly Gln Gly Thr Lys Leu Glu Ile Lys
            100                 105

<210> SEQ ID NO 62
<211> LENGTH: 6
<212> TYPE: PRT
<213> ORGANISM: homo sapiens

<400> SEQUENCE: 62

```
Gln Gly Ile Ser Ser Trp
1               5
```

<210> SEQ ID NO 63
<211> LENGTH: 3
<212> TYPE: PRT
<213> ORGANISM: homo sapiens

<400> SEQUENCE: 63

```
Ala Ala Ser
1
```

<210> SEQ ID NO 64
<211> LENGTH: 10
<212> TYPE: PRT
<213> ORGANISM: homo sapiens

<400> SEQUENCE: 64

```
Gln Gln Tyr Asn Ser Tyr Pro Leu Tyr Thr
1               5                   10
```

<210> SEQ ID NO 65
<211> LENGTH: 107
<212> TYPE: PRT
<213> ORGANISM: homo sapiens

<400> SEQUENCE: 65

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 66
<211> LENGTH: 6
<212> TYPE: PRT
<213> ORGANISM: homo sapiens

<400> SEQUENCE: 66

```
Gln Ser Val Ser Ser Tyr
1               5
```

<210> SEQ ID NO 67
<211> LENGTH: 3
<212> TYPE: PRT
<213> ORGANISM: homo sapiens

<400> SEQUENCE: 67

```
Asp Ala Ser
1
```

<210> SEQ ID NO 68

```
<211> LENGTH: 9
<212> TYPE: PRT
<213> ORGANISM: homo sapiens

<400> SEQUENCE: 68

Gln Gln Arg Ser Asn Trp Pro Leu Thr
1               5

<210> SEQ ID NO 69
<211> LENGTH: 107
<212> TYPE: PRT
<213> ORGANISM: homo sapiens

<400> SEQUENCE: 69

Glu Ile Val Leu Thr Gln Ser Pro Ala Thr Leu Ser Leu Ser Pro Gly
1               5                   10                  15

Glu Arg Ala Ile Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 70
<211> LENGTH: 6
<212> TYPE: PRT
<213> ORGANISM: homo sapiens

<400> SEQUENCE: 70

Gln Ser Val Ser Ser Tyr
1               5

<210> SEQ ID NO 71
<211> LENGTH: 3
<212> TYPE: PRT
<213> ORGANISM: homo sapiens

<400> SEQUENCE: 71

Asp Ala Ser
1

<210> SEQ ID NO 72
<211> LENGTH: 9
<212> TYPE: PRT
<213> ORGANISM: homo sapiens

<400> SEQUENCE: 72

Gln Gln Arg Ser Asn Trp Pro Leu Thr
1               5

<210> SEQ ID NO 73
<211> LENGTH: 107
<212> TYPE: PRT
<213> ORGANISM: homo sapiens

<400> SEQUENCE: 73
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 74
<211> LENGTH: 6
<212> TYPE: PRT
<213> ORGANISM: homo sapiens

<400> SEQUENCE: 74

Gln Gly Ile Ser Ser Trp
1               5

<210> SEQ ID NO 75
<211> LENGTH: 3
<212> TYPE: PRT
<213> ORGANISM: homo sapiens

<400> SEQUENCE: 75

Ala Ala Ser
1

<210> SEQ ID NO 76
<211> LENGTH: 9
<212> TYPE: PRT
<213> ORGANISM: homo sapiens

<400> SEQUENCE: 76

Gln Gln Tyr Asn Ser Tyr Pro Tyr Thr
1               5

<210> SEQ ID NO 77
<211> LENGTH: 107
<212> TYPE: PRT
<213> ORGANISM: homo sapiens

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

```
Thr Phe Gly Gly Gly Thr Lys Val Glu Ile Lys
            100                 105

<210> SEQ ID NO 78
<211> LENGTH: 6
<212> TYPE: PRT
<213> ORGANISM: homo sapiens

<400> SEQUENCE: 78

Gln Ser Val Ser Ser Tyr
1               5

<210> SEQ ID NO 79
<211> LENGTH: 3
<212> TYPE: PRT
<213> ORGANISM: homo sapiens

<400> SEQUENCE: 79

Asp Ala Ser
1

<210> SEQ ID NO 80
<211> LENGTH: 9
<212> TYPE: PRT
<213> ORGANISM: homo sapiens

<400> SEQUENCE: 80

Gln Gln Arg Ser Asn Trp Pro Leu Thr
1               5
```